United States Patent
Chou et al.

(10) Patent No.: US 10,501,503 B2
(45) Date of Patent: Dec. 10, 2019

(54) MODIFIED MEMBRANE PERMEABILITY

(71) Applicants: Cathay Biotech Inc., Shanghai (CN); CIBT America Inc., Newark, DE (US)

(72) Inventors: Howard Chou, Shanghai (CN); Lijun Yu, Shanghai (CN); Xiucai Liu, Shanghai (CN)

(73) Assignees: Cathay Biotech Inc., Shanghai (CN); CIBT America Inc., Newark, DE (US)

( * ) Notice: Subject to any disclaimer, the term of this patent is extended or adjusted under 35 U.S.C. 154(b) by 0 days.

(21) Appl. No.: 15/774,820

(22) PCT Filed: Nov. 9, 2015

(86) PCT No.: PCT/CN2015/094121
§ 371 (c)(1),
(2) Date: May 9, 2018

(87) PCT Pub. No.: WO2017/079872
PCT Pub. Date: May 18, 2017

(65) Prior Publication Data
US 2019/0031726 A1  Jan. 31, 2019

(51) Int. Cl.
| | |
|---|---|
| *C12N 9/88* | (2006.01) |
| *C12N 15/70* | (2006.01) |
| *C07K 14/245* | (2006.01) |
| *C12P 13/08* | (2006.01) |
| *C12P 13/00* | (2006.01) |

(52) U.S. Cl.
CPC .............. *C07K 14/245* (2013.01); *C12N 9/88* (2013.01); *C12N 15/70* (2013.01); *C12P 13/001* (2013.01); *C12P 13/08* (2013.01); *C12Y 401/01018* (2013.01)

(58) Field of Classification Search
None
See application file for complete search history.

(56) References Cited

U.S. PATENT DOCUMENTS

| | | |
|---|---|---|
| 2009/0068711 A1 | 3/2009 | Rieping |
| 2015/0218605 A1 | 8/2015 | Hoshino et al. |

FOREIGN PATENT DOCUMENTS

| | | |
|---|---|---|
| CN | 1993461 A | 7/2007 |
| EP | 2163613 A2 | 3/2010 |
| EP | 2405005 A2 | 1/2012 |
| WO | 03008600 A2 | 1/2003 |
| WO | 03008607 A2 | 1/2003 |

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340 ).*
Witkowski et al (Biochemistry 38:11643-11650, 1999).*
Seffernick et al., (J. Bacteriol. 183(8): 2405-2410, 2001).*
Broun et al (Science 282:1315-1317, 1998).*
Koebnik et al., "Structure and function of bacterial outer membrane proteins: barrels in a nutshell," Molecular Microbiology (2000); 37(2):239-253.
Galdiero et al., "Microbe-Host INteractions: Structure and Role of Gram-Negative Bacterial Porins," Current Protein and Peptide Science (2012); 13:843-854.
Zhang et al., "Construction, Expression and Purification of Gene Encloding omp2b Protein of *Brucella melitensis* in Prokaryotic Cell," Science Technology & Engineering (2011); Abstract Only.
Zhang et al., "Construction, Expression and Purification of Gene Encloding omp2b Protein of *Brucella melitensis* in Prokaryotic Cell," Science Technology & Engineering (2011); 10(25):6146-6149.
Wang et al., "Progress of Studies on Molecular Immunology of Outer Membrane Protein(OMP)of *Salmonella lignieres*," Chinese Journal of Zoonoses (2011); 19(4):106-108, 114.
Qian et al., "Metabolic Engineering of *Escherichia coli* for the Production of Cadaverine: A Five Carbon Diamine," Biotechnology & Bioengineering (2011); 108(1): 93-103.

* cited by examiner

*Primary Examiner* — Padmavathi Baskar
(74) *Attorney, Agent, or Firm* — Fox Rothschild LLP

(57) ABSTRACT

Provided are microorganisms genetically modified to over-express porin polypeptides to enhance the production of lysine and lysine derivatives by the microorganism. Also provided are methods of generating such microorganism, and methods of producing lysine and lysine derivatives using the genetically modified microorganisms.

6 Claims, No Drawings
Specification includes a Sequence Listing.

SEQUENCE LISTING

<160> NUMBER OF SEQ ID NOS: 102

<210> SEQ ID NO 1
<211> LENGTH: 2148
<212> TYPE: DNA
<213> ORGANISM: Escherichia coli

<400> SEQUENCE: 1
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac     120
gacttattaa aactgatcga aaacaatgcg cgtctgtgcg gcgttatttt tgactgggat     180
aaatataatc tcgagctgtg cgaagaaatt agcaaaatga cgagaaacct gccgttgtac     240
gcgttcgcta atacgtattc cactctcgat gtaagcctga atgacctgcg tttacagatt     300
agcttctttg aatatgcgct gggtgctgct gaagatattg ctaataagat caagcagacc     360
actgacgaat atatcaacac tattctgcct ccgctgacta agcactgtt taaatatgtt       420 cgtgaaggta aatatacttt ctgtactcct ggtcacatgg gcggtactgc attccagaaa     480
agcccggtag gtagcctgtt ctatgatttc tttggtccga ataccatgaa atctgatatt     540
tccatttcag tatctgaact gggttctctg ctggatcaca gtggtccaca caaagaagca     600

```
gaacagtata tcgctcgcgt ctttaacgca gaccgcagct acatggtgac caacggtact      660
tccactgcga acaaaattgt tggtatgtac tctgctccag caggcagcac cattctgatt      720
gaccgtaact gccacaaatc gctgacccac ctgatgatga tgagcgatgt tacgccaatc     780
tatttccgcc cgaccgtaa cgcttacggt attcttggtg gtatcccaca gagtgaattc      840
cagcacgcta ccattgctaa gcgcgtgaaa gaaacaccaa acgcaacctg gccggtacat     900
gctgtaatta ccaactctac ctatgatggt ctgctgtaca caccgactt catcaagaaa      960
acactggatg tgaaatccat ccactttgac tccgcgtggg tgccttacac caacttctca    1020
ccgatttacg aaggtaaatg cggtatgagc ggtggccgtg tagaagggaa agtgatttac    1080
gaaacccagt ccactcacaa actgctggcg gcgttctctc aggcttccat gatccacgtt    1140
aaaggtgaca taaacgaaga aacctttaac gaagcctaca tgatgcacac caccacttct    1200
ccgcactacg gtatcgtggc gtccactgaa accgctgcgg cgatgatgaa aggcaatgca    1260
ggtaagcgtc tgatcaacgg ttctattgaa cgtgcgatca aattccgtaa agagatcaaa    1320
cgtctgagaa cggaatctga tggctggttc tttgatgtat ggcagccgga tcatatcgat    1380
acgactgaat gctggccgct gcgttctgac agcacctggc acggcttcaa aaacatcgat    1440
aacgagcaca tgtatcttga cccgatcaaa gtcaccctgc tgactccggg gatggaaaaa    1500
gacggcacca tgagcgactt tggtattccg ccagcatcg tggcgaaata cctcgacgaa    1560
catggcatcg ttgttgagaa accggtccg tataacctgc tgttcctgtt cagcatcggt    1620
atcgataaga ccaaagcact gagcctgctg cgtgctctga ctgactttaa acgtgcgttc    1680
gacctgaacc tgcgtgtgaa aaacatgctg ccgtctctgt atcgtgaaga tcctgaattc    1740
tatgaaaaca tgcgtattca ggaactggct cagaatatcc acaaactgat tgttcaccac    1800
aatctgccgg atctgatgta tcgcgcattt gaagtgctgc cgacgatggt aatgactccg    1860
tatgctgcat tccagaaaga gctgcacggt atgaccgaag aagtttacct cgacgaaatg    1920
gtaggtcgta ttaacgccaa tatgatcctt ccgtacccgc cgggagttcc tctggtaatg    1980
ccgggtgaaa tgatcaccga agaaagccgt ccggttctgg agttcctgca gatgctgtgt    2040
gaaatcggcg ctcactatcc gggctttgaa accgatattc acggtgcata ccgtcaggct    2100
gatggccgct ataccgttaa ggtattgaaa gaagaaagca aaaaataa              2148
```

<210> SEQ ID NO 2
<211> LENGTH: 715
<212> TYPE: PRT
<213> ORGANISM: Escherichia coli

<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Leu Leu Lys Leu Ile Glu Asn
            35                  40                  45

Asn Ala Arg Leu Cys Gly Val Ile Phe Asp Trp Asp Lys Tyr Asn Leu
        50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95
```

```
Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
            115                 120                 125

Leu Pro Pro Leu Thr Lys Ala Leu Phe Lys Tyr Val Arg Glu Gly Lys
        130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
```

```
                515                 520                 525
Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
            610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
            690                 695                 700

Thr Val Lys Val Leu Lys Glu Glu Ser Lys Lys
705                 710                 715

<210> SEQ ID NO 3
<211> LENGTH: 1041
<212> TYPE: DNA
<213> ORGANISM: Escherichia coli

<400> SEQUENCE: 3
atgaaaaaga cagctatcgc gattgcagtg gcactggctg gtttcgctac cgtagcgcag    60
gccgctccga agataacac ctggtacact ggtgctaaac tgggctggtc ccagtaccat    120
gacactggtt tcatcaacaa caatggcccg acccatgaaa accaactggg cgctggtgct    180
tttggtggtt accaggttaa cccgtatgtt ggctttgaaa tgggttacga ctggttaggt    240
cgtatgccgt acaaaggcag cgttgaaaac ggtgcataca agctcagggg cgttcaactg    300
accgctaaac tgggttaccc aatcactgac gacctggaca tctacactcg tctgggtggc    360
atggtatggc gtgcagacac taaatccaac gtttatggta aaaaccacga caccggcgtt    420
tctccggtct cgctggcggt gttgagtac gcgatcactc tgaaaatcgc tacccgtctg    480
gaataccagt ggaccaacaa catcggtgac gcacacacca tcggcactcg tccggacaac    540
ggcatgctga gcctgggtgt ttcctaccgt ttcggtcagg gcgaagcagc tccagtagtt    600
gctccggctc cagctccggc accggaagta cagaccaagc acttcactct gaagtctgac    660
gttctgttca acttcaacaa agcaaccctg aaaccggaag gtcaggctgc tctggatcag    720
ctgtacagcc agctgagcaa cctggatccg aaagacggtt ccgtagttgt tctgggttac    780
accgaccgca tcggttctga cgcttacaac cagggtctgt ccgagcgccg tgctcagtct    840
gttgttgatt acctgatctc caaaggtatc ccggcagaca agatctccgc acgtggtatg    900
ggcgaatcca accggttac tggcaacacc tgtgacaacg tgaaacagcg tgctgcactg    960
atcgactgcc tggctccgga tcgtcgcgta gagatcgaag ttaaaggtat caaagacgtt    1020
```
gtaactcagc cgcaggctta a                                                        1041

<210> SEQ ID NO 4
<211> LENGTH: 346
<212> TYPE: PRT
<213> ORGANISM: Escherichia coli

<400> SEQUENCE: 4

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Thr Gly Ala
            20                  25                  30

Lys Leu Gly Trp Ser Gln Tyr His Asp Thr Gly Phe Ile Asn Asn Asn
        35                  40                  45

Gly Pro Thr His Glu Asn Gln Leu Gly Ala Gly Ala Phe Gly Gly Tyr
    50                  55                  60

Gln Val Asn Pro Tyr Val Gly Phe Glu Met Gly Tyr Asp Trp Leu Gly
65                  70                  75                  80

Arg Met Pro Tyr Lys Gly Ser Val Glu Asn Gly Ala Tyr Lys Ala Gln
                85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
        115                 120                 125

Ser Asn Val Tyr Gly Lys Asn His Asp Thr Gly Val Ser Pro Val Phe
    130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175

Arg Pro Asp Asn Gly Met Leu Ser Leu Gly Val Ser Tyr Arg Phe Gly
            180                 185                 190

Gln Gly Glu Ala Ala Pro Val Val Ala Pro Ala Pro Ala Pro Ala Pro
        195                 200                 205

Glu Val Gln Thr Lys His Phe Thr Leu Lys Ser Asp Val Leu Phe Asn
    210                 215                 220

Phe Asn Lys Ala Thr Leu Lys Pro Glu Gly Gln Ala Ala Leu Asp Gln
225                 230                 235                 240

Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
        275                 280                 285

Gly Ile Pro Ala Asp Lys Ile Ser Ala Arg Gly Met Gly Glu Ser Asn
    290                 295                 300

Pro Val Thr Gly Asn Thr Cys Asp Asn Val Lys Gln Arg Ala Ala Leu
305                 310                 315                 320

Ile Asp Cys Leu Ala Pro Asp Arg Arg Val Glu Ile Glu Val Lys Gly
                325                 330                 335

Ile Lys Asp Val Val Thr Gln Pro Gln Ala
            340                 345

<210> SEQ ID NO 5

```
<211> LENGTH: 1104
<212> TYPE: DNA
<213> ORGANISM: Escherichia coli

<400> SEQUENCE: 5
atgaaagtta aagtactgtc cctcctggtc ccagctctgc tggtagcagg cgcagcaaac      60
gctgctgaag tttacaacaa agacggcaac aaattagatc tgtacggtaa agtagacggc     120
ctgcactatt tctctgacaa caaagatgta gatggcgacc agacctacat gcgtcttggc     180
ttcaaaggtg aaactcaggt tactgaccag ctgaccggtt acggccagtg ggaatatcag     240
atccagggca cagcgctga aaacgaaaac aactcctgga cccgtgtggc attcgcaggt     300
ctgaaattcc aggatgtggg ttctttcgac tacggtcgta actacggcgt tgtttatgac     360
gtaacttcct ggaccgacgt actgccagaa ttcggtggtg acacctacgg ttctgacaac     420
ttcatgcagc agcgtggtaa cggcttcgcg acctaccgta acactgactt cttcggtctg     480
gttgacggcc tgaactttgc tgttcagtac cagggtaaaa acggcaaccc atctggtgaa     540
ggctttacta gtggcgtaac taacaacggt cgtgacgcac tgcgtcaaaa cggcgacggc     600
gtcggcggtt ctatcactta tgattacgaa ggtttcggta cggtggtgc gatctccagc     660
tccaaacgta ctgatgctca gaacaccgct gcttacatcg gtaacggcga ccgtgctgaa     720
acctacactg gtggtctgaa atacgacgct aacaacatct acctggctgc tcagtacacc     780
cagacctaca cgcaactcg cgtaggttcc ctgggttggg cgaacaaagc acagaacttc     840
gaagctgttg ctcagtacca gttcgacttc ggtctgcgtc cgtccctggc ttacctgcag     900
tctaaaggta aaaacctggg tcgtggctac gacgacgaag atatcctgaa atatgttgat     960
gttggtgcta cctactactt caacaaaaac atgtccacct acgttgacta caaaatcaac    1020
ctgctggacg acaaccagtt cactcgtgac gctggcatca acactgataa catcgtagct    1080
ctgggtctgg tttaccagtt ctaa                                          1104

<210> SEQ ID NO 6
<211> LENGTH: 367
<212> TYPE: PRT
<213> ORGANISM: Escherichia coli

<400> SEQUENCE: 6

Met Lys Val Lys Val Leu Ser Leu Leu Val Pro Ala Leu Leu Val Ala
1               5                   10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Asp Val Asp Gly Asp Gln Thr Tyr Met Arg Leu Gly Phe Lys Gly Glu
    50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
    130                 135                 140
```

Arg Gly Asn Gly Phe Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
            165                 170                 175

Pro Ser Gly Glu Gly Phe Thr Ser Gly Val Thr Asn Asn Gly Arg Asp
        180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
            245                 250                 255

Ala Gln Tyr Thr Gln Thr Tyr Asn Ala Thr Arg Val Gly Ser Leu Gly
        260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
290                 295                 300

Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
            325                 330                 335

Tyr Lys Ile Asn Leu Leu Asp Asp Asn Gln Phe Thr Arg Asp Ala Gly
        340                 345                 350

Ile Asn Thr Asp Asn Ile Val Ala Leu Gly Leu Val Tyr Gln Phe
        355                 360                 365

<210> SEQ ID NO 7
<211> LENGTH: 1086
<212> TYPE: DNA
<213> ORGANISM: Escherichia coli

<400> SEQUENCE: 7
atgaagcgca atattctggc agtgatcgtc cctgctctgt tagtagcagg tactgcaaac      60
gctgcagaaa tctataacaa agatggcaac aaagtagatc tgtacggtaa agctgttggt     120
ctgcattatt tttccaaggg taacggtgaa acagttacg gtggcaatgg cgacatgacc      180
tatgcccgtc ttggttttaa aggggaaact caaatcaatt ccgatctgac cggttatggt     240
cagtgggaat ataacttcca gggtaacaac tctgaaggcg ctgacgctca aactggtaac     300
aaaacgcgtc tggcattcgc gggtcttaaa tacgctgacg ttggttcttt cgattacggc     360
cgtaactacg gtgtggttta tgatgcactg ggttacaccg atatgctgcc agaatttggt     420
ggtgatactg catacagcga tgacttcttc gttggtcgtg ttggcggcgt tgctacctat     480
cgtaactcca acttctttgg tctggttgat ggcctgaact cgctgttca gtacctgggt     540 aaaaacgagc gtgacactgc acgccgttct aacggcgacg tgttggcgg ttctatcagc     600 tacgaatacg aaggctttgg tatcgttggt gcttatggtg cagctgaccg taccaacctg     660
caagaagctc aacctcttgg caacggtaaa aaagctgaac agtgggctac tggtctgaag     720
tacgacgcga caacatcta cctggcagcg aactacggtg aaacccgtaa cgctacgccg     780
atcactaata aatttacaaa caccagcggc ttcgccaaca aaacgcaaga cgttctgtta     840
gttgcgcaat accagttcga tttcggtctg cgtccgtcca tcgcttacac caaatctaaa     900

```
gcgaaagacg tagaaggtat cggtgatgtt gatctggtga actactttga agtgggcgca        960
acctactact tcaacaaaaa catgtccacc tatgttgact acatcatcaa ccagatcgat       1020
tctgacaaca aactgggcgt aggttcagac gacaccgttg ctgtgggtat cgtttaccag       1080
ttctaa                                                                  1086
```

<210> SEQ ID NO 8
<211> LENGTH: 361
<212> TYPE: PRT
<213> ORGANISM: Escherichia coli

<400> SEQUENCE: 8

```
Met Lys Arg Asn Ile Leu Ala Val Ile Val Pro Ala Leu Leu Val Ala
1               5                   10                  15

Gly Thr Ala Asn Ala Ala Glu Ile Tyr Asn Lys Asp Gly Asn Lys Val
            20                  25                  30

Asp Leu Tyr Gly Lys Ala Val Gly Leu His Tyr Phe Ser Lys Gly Asn
        35                  40                  45

Gly Glu Asn Ser Tyr Gly Gly Asn Gly Asp Met Thr Tyr Ala Arg Leu
    50                  55                  60

Gly Phe Lys Gly Glu Thr Gln Ile Asn Ser Asp Leu Thr Gly Tyr Gly
65                  70                  75                  80

Gln Trp Glu Tyr Asn Phe Gln Gly Asn Asn Ser Glu Gly Ala Asp Ala
                85                  90                  95

Gln Thr Gly Asn Lys Thr Arg Leu Ala Phe Ala Gly Leu Lys Tyr Ala
            100                 105                 110

Asp Val Gly Ser Phe Asp Tyr Gly Arg Asn Tyr Gly Val Val Tyr Asp
        115                 120                 125

Ala Leu Gly Tyr Thr Asp Met Leu Pro Glu Phe Gly Gly Asp Thr Ala
    130                 135                 140

Tyr Ser Asp Asp Phe Phe Val Gly Arg Val Gly Gly Val Ala Thr Tyr
145                 150                 155                 160

Arg Asn Ser Asn Phe Phe Gly Leu Val Asp Gly Leu Asn Phe Ala Val
                165                 170                 175

Gln Tyr Leu Gly Lys Asn Glu Arg Asp Thr Ala Arg Arg Ser Asn Gly
            180                 185                 190

Asp Gly Val Gly Gly Ser Ile Ser Tyr Glu Tyr Glu Gly Phe Gly Ile
        195                 200                 205

Val Gly Ala Tyr Gly Ala Ala Asp Arg Thr Asn Leu Gln Glu Ala Gln
    210                 215                 220

Pro Leu Gly Asn Gly Lys Lys Ala Glu Gln Trp Ala Thr Gly Leu Lys
225                 230                 235                 240

Tyr Asp Ala Asn Asn Ile Tyr Leu Ala Ala Asn Tyr Gly Glu Thr Arg
                245                 250                 255

Asn Ala Thr Pro Ile Thr Asn Lys Phe Thr Asn Thr Ser Gly Phe Ala
            260                 265                 270

Asn Lys Thr Gln Asp Val Leu Leu Val Ala Gln Tyr Gln Phe Asp Phe
        275                 280                 285

Gly Leu Arg Pro Ser Ile Ala Tyr Thr Lys Ser Lys Ala Lys Asp Val
    290                 295                 300

Glu Gly Ile Gly Asp Val Asp Leu Val Asn Tyr Phe Glu Val Gly Ala
305                 310                 315                 320

Thr Tyr Tyr Phe Asn Lys Asn Met Ser Thr Tyr Val Asp Tyr Ile Ile
                325                 330                 335
```

```
Asn Gln Ile Asp Ser Asp Asn Lys Leu Gly Val Gly Ser Asp Asp Thr
            340                 345                 350

Val Ala Val Gly Ile Val Tyr Gln Phe
            355                 360
```

<210> SEQ ID NO 9
<211> LENGTH: 516
<212> TYPE: DNA
<213> ORGANISM: Escherichia coli

<400> SEQUENCE: 9

```
atgaaaaaaa ttgcatgtct ttcagcactg gccgcagttc tggctttcac cgcaggtact    60
tccgtagctg cgacttctac tgtaactggc ggttacgcac agagcgacgc tcagggccaa   120
atgaacaaaa tgggcggttt caacctgaaa taccgctatg aagaagacaa cagcccgctg   180
ggtgtgatcg gttctttcac ttacaccgag aaaagccgta ctgcaagctc tggtgactac   240
aacaaaaacc agtactacgg catcactgct ggtccggctt accgcattaa cgactgggca   300
agcatctacg gtgtagtggg tgtgggttat ggtaaattcc agaccactga atacccgacc   360
tacaaacacg acaccagcga ctacggtttc tcctacggtg cgggtctgca gttcaacccg   420
atggaaaacg ttgctctgga cttctcttac gagcagagcc gtattcgtag cgttgacgta   480
ggcacctgga ttgccggtgt tggttaccgc ttctaa                             516
```

<210> SEQ ID NO 10
<211> LENGTH: 171
<212> TYPE: PRT
<213> ORGANISM: Escherichia coli

<400> SEQUENCE: 10

```
Met Lys Lys Ile Ala Cys Leu Ser Ala Leu Ala Ala Val Leu Ala Phe
1               5                   10                  15

Thr Ala Gly Thr Ser Val Ala Ala Thr Ser Thr Val Thr Gly Gly Tyr
            20                  25                  30

Ala Gln Ser Asp Ala Gln Gly Gln Met Asn Lys Met Gly Gly Phe Asn
        35                  40                  45

Leu Lys Tyr Arg Tyr Glu Glu Asp Asn Ser Pro Leu Gly Val Ile Gly
    50                  55                  60

Ser Phe Thr Tyr Thr Glu Lys Ser Arg Thr Ala Ser Ser Gly Asp Tyr
65                  70                  75                  80

Asn Lys Asn Gln Tyr Tyr Gly Ile Thr Ala Gly Pro Ala Tyr Arg Ile
                85                  90                  95

Asn Asp Trp Ala Ser Ile Tyr Gly Val Val Gly Val Gly Tyr Gly Lys
            100                 105                 110

Phe Gln Thr Thr Glu Tyr Pro Thr Tyr Lys His Asp Thr Ser Asp Tyr
        115                 120                 125

Gly Phe Ser Tyr Gly Ala Gly Leu Gln Phe Asn Pro Met Glu Asn Val
    130                 135                 140

Ala Leu Asp Phe Ser Tyr Glu Gln Ser Arg Ile Arg Ser Val Asp Val
145                 150                 155                 160

Gly Thr Trp Ile Ala Gly Val Gly Tyr Arg Phe
                165                 170
```

<210> SEQ ID NO 11
<211> LENGTH: 1056
<212> TYPE: DNA
<213> ORGANISM: Escherichia coli

<400> SEQUENCE: 11

```
atgaaaaaga gcactctggc attagtggtg atgggcattg tggcatctgc atctgtacag    60
gctgcagaaa tatataataa agacggtaat aaactggatg tctatggcaa agttaaagcc   120
atgcattata tgagtgataa cgccagtaaa gatggcgacc agagttatat ccgttttggt   180
ttcaaaggcg aaacacaaat taacgatcaa ctgactggtt atggtcgttg ggaagcagag   240
tttgccggta taaagcaga gagtgatact gcacagcaaa aaacgcgtct cgcttttgcc   300
gggttgaaat ataagagattt gggttctttc gattatggtc gtaacctggg ggcgttgtat   360
gacgtggaag cctggaccga tatgttcccg gaatttggtg gcgattcctc ggcgcagacc   420
gacaacttta tgaccaaacg cgccagcggt ctggcgacgt atcggaacac cgacttcttc   480
ggcgttatcg atggcctgaa cttaaccctg caatatcaag ggaaaaacga aaccgcgac   540
gttaaaaagc aaaacggcga tggcttcggc acgtcattga catatgactt tggcggcagc   600
gatttcgcca ttagtgggc ctataccaac tcagatcgca ccaacgagca gaacctgcaa    660
agccgtggca caggcaagcg tgcagaagca tgggcaacag gtctgaaata cgatgccaat   720
aatatttatc tggcaacttt ctattctgaa acacgcaaaa tgacgccaat aactggcggc   780
tttgccaata agacacagaa cttggaagcg tcgctcaat accagtttga ctttggtctg    840
cgtccatcgc tgggttatgt cttatcgaaa gggaaagata ttgaaggtat cggtgatgaa   900
gatctggtca attatatcga cgtcggtgct acgtattatt tcaacaaaaa tatgtcagcg   960
tttgttgatt ataaaatcaa ccaactggat agcgataaca aattgaatat taataatgat  1020
gatattgtcg cggttggcat gacgtatcag ttttaa                            1056
```

```
<210> SEQ ID NO 12
<211> LENGTH: 351
<212> TYPE: PRT
<213> ORGANISM: Escherichia coli

<400> SEQUENCE: 12
```

Met Lys Lys Ser Thr Leu Ala Leu Val Val Met Gly Ile Val Ala Ser
1               5                   10                  15

Ala Ser Val Gln Ala Ala Glu Ile Tyr Asn Lys Asp Gly Asn Lys Leu
                20                  25                  30

Asp Val Tyr Gly Lys Val Lys Ala Met His Tyr Met Ser Asp Asn Ala
            35                  40                  45

Ser Lys Asp Gly Asp Gln Ser Tyr Ile Arg Phe Gly Phe Lys Gly Glu
        50                  55                  60

Thr Gln Ile Asn Asp Gln Leu Thr Gly Tyr Gly Arg Trp Glu Ala Glu
65                  70                  75                  80

Phe Ala Gly Asn Lys Ala Glu Ser Asp Thr Ala Gln Gln Lys Thr Arg
                85                  90                  95

Leu Ala Phe Ala Gly Leu Lys Tyr Lys Asp Leu Gly Ser Phe Asp Tyr
            100                 105                 110

Gly Arg Asn Leu Gly Ala Leu Tyr Asp Val Glu Ala Trp Thr Asp Met
        115                 120                 125

Phe Pro Glu Phe Gly Gly Asp Ser Ser Ala Gln Thr Asp Asn Phe Met
    130                 135                 140

Thr Lys Arg Ala Ser Gly Leu Ala Thr Tyr Arg Asn Thr Asp Phe Phe
145                 150                 155                 160

Gly Val Ile Asp Gly Leu Asn Leu Thr Leu Gln Tyr Gln Gly Lys Asn
                165                 170                 175

```
Glu Asn Arg Asp Val Lys Lys Gln Asn Gly Asp Gly Phe Gly Thr Ser
            180                 185                 190

Leu Thr Tyr Asp Phe Gly Gly Ser Asp Phe Ala Ile Ser Gly Ala Tyr
        195                 200                 205

Thr Asn Ser Asp Arg Thr Asn Glu Gln Asn Leu Gln Ser Arg Gly Thr
    210                 215                 220

Gly Lys Arg Ala Glu Ala Trp Ala Thr Gly Leu Lys Tyr Asp Ala Asn
225                 230                 235                 240

Asn Ile Tyr Leu Ala Thr Phe Tyr Ser Glu Thr Arg Lys Met Thr Pro
                245                 250                 255

Ile Thr Gly Gly Phe Ala Asn Lys Thr Gln Asn Phe Glu Ala Val Ala
            260                 265                 270

Gln Tyr Gln Phe Asp Phe Gly Leu Arg Pro Ser Leu Gly Tyr Val Leu
        275                 280                 285

Ser Lys Gly Lys Asp Ile Glu Gly Ile Gly Asp Glu Asp Leu Val Asn
    290                 295                 300

Tyr Ile Asp Val Gly Ala Thr Tyr Tyr Phe Asn Lys Asn Met Ser Ala
305                 310                 315                 320

Phe Val Asp Tyr Lys Ile Asn Gln Leu Asp Ser Asp Asn Lys Leu Asn
                325                 330                 335

Ile Asn Asn Asp Asp Ile Val Ala Val Gly Met Thr Tyr Gln Phe
            340                 345                 350

<210> SEQ ID NO 13
<211> LENGTH: 906
<212> TYPE: DNA
<213> ORGANISM: Escherichia coli

<400> SEQUENCE: 13
atgaaaaagt tattccctg taccgcactg gtgatgtgtg cgggaatggc ctgcgcacag      60
gccgaggaaa ggaacgactg gcactttaat atcggcgcga tgtacgaaat agaaaacgtc     120
gagggttatg cgaagatat ggatgggctg cggagcctt cagtctattt taatgccgcc      180
aacgggccgt ggagaattgc tctggcctat tatcaggaag gccggtagaa ttatagcgcg     240
ggtaaacgtg aacgtggtt tgatcgcccg gagctggagg tgcattatca gttcctcgaa     300
aacgatgatt tcagtttcgg cctgaccggc ggtttccgta attatggtta tcactacgtt     360
gatgaaccgg gtaaagacac ggcgaatatg cagcgctgga aaatcgcgcc agactgggat     420
gtgaaactga ctgacgattt acgtttcaac ggttggttgt cgatgtataa atttgccaac     480
gatctgaaca ctaccggtta cgctgatacc cgtgtcgaaa cggaaacagg tctgcaatat     540
accttcaacg aaacggttgc cttgcgagtg aactattatc tcgagcgcgg cttcaatatg     600
gacgacagcc gcaataacgg tgagttttcc acgcaagaaa ttcgcgccta tttgccgctg     660
acgctcggca accactcggt gacgccgtat acgcgcattg gctggatcg ctggagtaac     720 tgggactggc aggatgatat tgaacgtgaa ggccatgatt ttaaccgtgt aggtttattt     780
tacggttatg atttccagaa cggactttcc gtttcgctgg aatacgcgtt tgagtggcag     840
gatcacgacg aaggcgacag tgataaattc cattatgcag gtgtcggcgt aaattactcg     900
ttctga                                                               906

<210> SEQ ID NO 14
<211> LENGTH: 301
<212> TYPE: PRT
<213> ORGANISM: Escherichia coli
```

<400> SEQUENCE: 14

Met Lys Lys Leu Leu Pro Cys Thr Ala Leu Val Cys Ala Gly Met
1               5                   10                  15

Ala Cys Ala Gln Ala Glu Glu Arg Asn Asp Trp His Phe Asn Ile Gly
            20                  25                  30

Ala Met Tyr Glu Ile Glu Asn Val Glu Gly Tyr Gly Glu Asp Met Asp
        35                  40                  45

Gly Leu Ala Glu Pro Ser Val Tyr Phe Asn Ala Ala Asn Gly Pro Trp
    50                  55                  60

Arg Ile Ala Leu Ala Tyr Tyr Gln Glu Gly Pro Val Asp Tyr Ser Ala
65              70                  75                  80

Gly Lys Arg Gly Thr Trp Phe Asp Arg Pro Glu Leu Glu Val His Tyr
            85                  90                  95

Gln Phe Leu Glu Asn Asp Asp Phe Ser Phe Gly Leu Thr Gly Gly Phe
        100                 105                 110

Arg Asn Tyr Gly Tyr His Tyr Val Asp Glu Pro Gly Lys Asp Thr Ala
    115                 120                 125

Asn Met Gln Arg Trp Lys Ile Ala Pro Asp Trp Asp Val Lys Leu Thr
130                 135                 140

Asp Asp Leu Arg Phe Asn Gly Trp Leu Ser Met Tyr Lys Phe Ala Asn
145                 150                 155                 160

Asp Leu Asn Thr Thr Gly Tyr Ala Asp Thr Arg Val Glu Thr Glu Thr
                165                 170                 175

Gly Leu Gln Tyr Thr Phe Asn Glu Thr Val Ala Leu Arg Val Asn Tyr
            180                 185                 190

Tyr Leu Glu Arg Gly Phe Asn Met Asp Asp Ser Arg Asn Asn Gly Glu
        195                 200                 205

Phe Ser Thr Gln Glu Ile Arg Ala Tyr Leu Pro Leu Thr Leu Gly Asn
    210                 215                 220

His Ser Val Thr Pro Tyr Thr Arg Ile Gly Leu Asp Arg Trp Ser Asn
225                 230                 235                 240

Trp Asp Trp Gln Asp Asp Ile Glu Arg Glu Gly His Asp Phe Asn Arg
                245                 250                 255

Val Gly Leu Phe Tyr Gly Tyr Asp Phe Gln Asn Gly Leu Ser Val Ser
            260                 265                 270

Leu Glu Tyr Ala Phe Glu Trp Gln Asp His Asp Glu Gly Asp Ser Asp
        275                 280                 285

Lys Phe His Tyr Ala Gly Val Gly Val Asn Tyr Ser Phe
    290                 295                 300

<210> SEQ ID NO 15
<211> LENGTH: 639
<212> TYPE: DNA
<213> ORGANISM: Escherichia coli

<400> SEQUENCE: 15
atgaaaaagt taacagtggc ggctttggca gtaacaactc ttctctctgg cagtgccttt     60
gcgcatgaag caggcgaatt ttttatgcgt gcaggttctg caaccgtacg tccaacagaa    120
ggtgctggtg gtacgttagg aagtctgggt ggattcagcg tgaccaataa cacgcaactg    180
ggccttacgt ttacttatat ggcgaccgac aacattggtg tggaattact ggcagcgacg    240
ccgttccgcc ataaaatcgg cacccggggcg accggcgata ttgcaaccgt tcatcatctg    300
ccaccaacac tgatggcgca gtggtatttt ggtgatgcca gcagcaaatt ccgtccttac    360

-continued

```
gttggggcag gtattaacta caccaccttc tttgataatg gatttaacga tcatggcaaa    420
gaggcagggc tttccgatct cagtctgaaa gattcctggg gagctgccgg gcaggtgggg    480
gttgattatc tgattaaccg tgactggttg gttaacatgt cagtgtggta catggatatc    540
gataccaccg ccaattataa gctgggcggt gcacagcaac acgatagcgt acgcctcgat    600
ccgtgggtgt ttatgttctc agcaggatat cgttttttaa                         639
```

```
<210> SEQ ID NO 16
<211> LENGTH: 212
<212> TYPE: PRT
<213> ORGANISM: Escherichia coli

<400> SEQUENCE: 16
```

Met Lys Lys Leu Thr Val Ala Ala Leu Ala Val Thr Thr Leu Leu Ser
1               5                   10                  15

Gly Ser Ala Phe Ala His Glu Ala Gly Glu Phe Met Arg Ala Gly
        20                  25                  30

Ser Ala Thr Val Arg Pro Thr Glu Gly Ala Gly Gly Thr Leu Gly Ser
    35                  40                  45

Leu Gly Gly Phe Ser Val Thr Asn Asn Thr Gln Leu Gly Leu Thr Phe
50                  55                  60

Thr Tyr Met Ala Thr Asp Asn Ile Gly Val Glu Leu Leu Ala Ala Thr
65                  70                  75                  80

Pro Phe Arg His Lys Ile Gly Thr Arg Ala Thr Gly Asp Ile Ala Thr
                85                  90                  95

Val His His Leu Pro Pro Thr Leu Met Ala Gln Trp Tyr Phe Gly Asp
            100                 105                 110

Ala Ser Ser Lys Phe Arg Pro Tyr Val Gly Ala Gly Ile Asn Tyr Thr
        115                 120                 125

Thr Phe Phe Asp Asn Gly Phe Asn Asp His Gly Lys Glu Ala Gly Leu
    130                 135                 140

Ser Asp Leu Ser Leu Lys Asp Ser Trp Gly Ala Ala Gly Gln Val Gly
145                 150                 155                 160

Val Asp Tyr Leu Ile Asn Arg Asp Trp Leu Val Asn Met Ser Val Trp
                165                 170                 175

Tyr Met Asp Ile Asp Thr Thr Ala Asn Tyr Lys Leu Gly Gly Ala Gln
            180                 185                 190

Gln His Asp Ser Val Arg Leu Asp Pro Trp Val Phe Met Phe Ser Ala
        195                 200                 205

Gly Tyr Arg Phe
    210

```
<210> SEQ ID NO 17
<211> LENGTH: 38
<212> TYPE: DNA
<213> ORGANISM: Artificial
<220> FEATURE:
<223> OTHER INFORMATION: synthetic promoter nucleic acid sequence

<400> SEQUENCE: 17
agtttattct tgacatgtag tgaggggct ggtataat                              38
```

```
<210> SEQ ID NO 18
<211> LENGTH: 1191
<212> TYPE: DNA
<213> ORGANISM: Escherichia coli
```

<400> SEQUENCE: 18

```
atgaaatcta acaatgcgct catcgtcatc ctcggcaccg tcaccctgga tgctgtaggc      60
ataggcttgg ttatgccggt actgccgggc ctcttgcggg atatcgtcca ttccgacagc     120
atcgccagtc actatggcgt gctgctagcg ctatatgcgt tgatgcaatt tctatgcgca     180
cccgttctcg gagcactgtc cgaccgcttt ggccgccgcc cagtcctgct cgcttcgcta     240
cttggagcca ctatcgacta cgcgatcatg gcgaccacac ccgtcctgtg gatcctctac     300
gccggacgca tcgtggccgg catcaccggc gccacaggtg cggttgctgg cgcctatatc     360
gccgacatca ccgatgggga agatcgggct cgccacttcg ggctcatgag cgcttgtttc     420
ggcgtgggta tggtggcagg ccccgtggcc ggggactgt gggcgccat ctccttgcat     480
gcaccattcc ttgcggcggc ggtgctcaac ggcctcaacc tactactggg ctgcttccta     540
atgcaggagt cgcataaggg agagcgtcga ccgatgccct tgagagcctt caacccagtc     600
agctccttcc ggtgggcgcg gggcatgact atcgtcgccg cacttatgac tgtcttcttt     660
atcatgcaac tcgtaggaca ggtgccggca cgctctgggt cattttcgg cgaggaccgc     720
tttcgctgga gcgcgacgat gatcggcctg tcgcttgcgg tattcggaat cttgcacgcc     780
ctcgctcaag ccttcgtcac tggtcccgcc accaaacgtt tcggcgagaa gcaggccatt     840
atcgccggca tggcggccga cgcgctgggc tacgtcttgc tggcgttcgc gacgcgaggc     900
tggatggcct tccccattat gattcttctc gcttccggcg catcgggat gcccgcgttg     960
caggccatgc tgtccaggca ggtagatgac gaccatcagg gacagcttca aggatcgctc    1020
gcggctctta ccagcctaac ttcgatcatt ggaccgctga tcgtcacggc gatttatgcc    1080
gcctcggcga gcacatggaa cgggttggca tggattgtag gcgccgccct ataccttgtc    1140
tgcctccccg cgttgcgtcg cggtgcatgg agccgggcca cctcgacctg a             1191
```

<210> SEQ ID NO 19
<211> LENGTH: 396
<212> TYPE: PRT
<213> ORGANISM: Escherichia coli

<400> SEQUENCE: 19

```
Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
    130                 135                 140

Val Ala Gly Pro Val Ala Gly Gly Leu Leu Gly Ala Ile Ser Leu His
145                 150                 155                 160
```

Ala Pro Phe Leu Ala Ala Val Leu Asn Gly Leu Asn Leu Leu Leu
                165                 170                 175

Gly Cys Phe Leu Met Gln Glu Ser His Lys Gly Glu Arg Arg Pro Met
            180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
    210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
            260                 265                 270

Arg Phe Gly Glu Lys Gln Ala Ile Ile Ala Gly Met Ala Ala Asp Ala
        275                 280                 285

Leu Gly Tyr Val Leu Leu Ala Phe Ala Thr Arg Gly Trp Met Ala Phe
    290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp Asp His Gln Gly Gln Leu
                325                 330                 335

Gln Gly Ser Leu Ala Ala Leu Thr Ser Leu Thr Ser Ile Ile Gly Pro
            340                 345                 350

Leu Ile Val Thr Ala Ile Tyr Ala Ala Ser Ala Ser Thr Trp Asn Gly
        355                 360                 365

Leu Ala Trp Ile Val Gly Ala Ala Leu Tyr Leu Val Cys Leu Pro Ala
    370                 375                 380

Leu Arg Arg Gly Ala Trp Ser Arg Ala Thr Ser Thr
385                 390                 395

<210> SEQ ID NO 20
<211> LENGTH: 1350
<212> TYPE: DNA
<213> ORGANISM: Escherichia coli

<400> SEQUENCE: 20
atgtctgaaa ttgttgtctc caaatttggc ggtaccagcg tagctgattt tgacgccatg     60
aaccgcagcg ctgatattgt gctttctgat gccaacgtgc gtttagttgt cctctcggct    120
tctgctggta tcactaatct gctggtcgct ttagctgaag gactggaacc tggcgagcga    180
ttcgaaaaac tcgacgctat ccgcaacatc cagtttgcca ttctggaacg tctgcgttac    240
ccgaacgtta tccgtgaaga gattgaacgt ctgctggaga cattactgt ctctggcagaa    300 gcggcggcgc tggcaacgtc tccggcgctg acagatgagc tggtcagcca cggcgagctg    360
atgtcgaccc tgctgtttgt tgagatcctg cgcgaacgcg atgttcaggc acagtggttt    420
gatgtacgta aagtgatgcg taccaacgac cgatttggtc gtgcagagcc agatatagcc    480
gcgctggcgg aactggccgc gctgcagctg ctcccacgtc tcaatgaagg cttagtgatc    540
acccagggat ttatcggtag cgaaaataaa ggtcgtacaa cgacgcttgg ccgtggaggc    600
agcgattata cggcagcctt gctggcggag gctttacacg catctcgtgt tgatatctgg    660
accgacgtcc cggcatcta caccaccgat ccacgcgtag tttccgcagc aaaacgcatt    720
gatgaaatcg cgtttgccga agcggcagag atggcaactt ttggtgcaaa agtactgcat    780

```
ccggcaacgt tgctacccgc agtacgcagc gatatcccgg tctttgtcgg ctccagcaaa    840
gacccacgcg caggtggtac gctggtgtgc aataaaactg aaaatccgcc gctgttccgc    900
gctctggcgc ttcgtcgcaa tcagactctg ctcactttgc acagcctgaa tatgctgcat    960
tctcgcggtt cctcgcgga agttttcggc atcctcgcgc ggcataatat tcggtagac    1020 ttaatcacca cgtcagaagt gagcgtggca ttaacccttg ataccaccgg ttcaacctcc   1080
actggcgata cgttgctgac gcaatctctg ctgatggagc tttccgcact gtgtcgggtg   1140
gaggtggaag aaggtctggc gctggtcgcg ttgattggca atgacctgtc aaaagcctgc   1200
ggcgttggca agaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                     1350
```

<210> SEQ ID NO 21
<211> LENGTH: 449
<212> TYPE: PRT
<213> ORGANISM: Escherichia coli

<400> SEQUENCE: 21

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
    65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270
```

```
Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
        290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
        435                 440                 445

Glu

<210> SEQ ID NO 22
<211> LENGTH: 879
<212> TYPE: DNA
<213> ORGANISM: Escherichia coli

<400> SEQUENCE: 22
atgttcacgg gaagtattgt cgcgattgtt actccgatgg atgaaaaagg taatgtctgt      60
cgggctagct tgaaaaaact gattgattat catgtcgcca gcggtacttc ggcgatcgtt     120
tctgttggca ccactggcga gtccgctacc ttaaatcatg acgaacatgc tgatgtggtg     180
atgatgacgc tggatctggc tgatgggcgc attccggtaa ttgccgggac cggcgctaac     240
gctactgcgg aagccattag cctgacgcag cgcttcaatg acagtggtat cgtcggctgc     300
ctgacggtaa cccttacta caatcgtccg tcgcaagaag gtttgtatca gcatttcaaa      360
gccatcgctg agcatactga cctgccgcaa attctgtata atgtgccgtc ccgtactggc     420
tgcgatctgc tcccggaaac ggtgggccgt ctggcgaaag taaaaaatat tatcggaatc     480
aaagaggcaa cagggaactt aacgcgtgta aaccagatca aagagctggt ttcagatgat     540
tttgttctgc tgagcggcga tgatgcgagc gcgctggact tcatgcaatt gggcggtcat     600
ggggttattt ccgttacggc taacgtcgca gcgcgtgata tggcccagat gtgcaaactg     660
gcagcagaag ggcattttgc cgaggcacgc gttattaatc agcgtctgat gccattacac     720
aacaaactat ttgtcgaacc caatccaatc ccggtgaaat gggcatgtaa ggaactgggt     780
cttgtggcga ccgatacgct gcgcctgcca atgacaccaa tcaccgacag tggtcgtgag     840
acggtcagag cggcgcttaa gcatgccggt ttgctgtaa                            879

<210> SEQ ID NO 23
<211> LENGTH: 292
<212> TYPE: PRT
<213> ORGANISM: Escherichia coli
```

<400> SEQUENCE: 23

| | | | | | | | | | | | | | | |
|---|---|---|---|---|---|---|---|---|---|---|---|---|---|---|
|Met|Phe|Thr|Gly|Ser|Ile|Val|Ala|Ile|Val|Thr|Pro|Met|Asp|Glu|Lys|
|1| | | |5| | | | |10| | | | |15|
|Gly|Asn|Val|Cys|Arg|Ala|Ser|Leu|Lys|Lys|Leu|Ile|Asp|Tyr|His|Val|
| | | |20| | | | |25| | | | |30| | |
|Ala|Ser|Gly|Thr|Ser|Ala|Ile|Val|Ser|Val|Gly|Thr|Thr|Gly|Glu|Ser|
| | |35| | | | |40| | | | |45| | | |
|Ala|Thr|Leu|Asn|His|Asp|Glu|His|Ala|Asp|Val|Val|Met|Met|Thr|Leu|
| |50| | | | |55| | | | |60| | | | |
|Asp|Leu|Ala|Asp|Gly|Arg|Ile|Pro|Val|Ile|Ala|Gly|Thr|Gly|Ala|Asn|
|65| | | | |70| | | | |75| | | | |80|
|Ala|Thr|Ala|Glu|Ala|Ile|Ser|Leu|Thr|Gln|Arg|Phe|Asn|Asp|Ser|Gly|
| | | | |85| | | | |90| | | | |95| |
|Ile|Val|Gly|Cys|Leu|Thr|Val|Thr|Pro|Tyr|Tyr|Asn|Arg|Pro|Ser|Gln|
| | | |100| | | | |105| | | | |110| | |
|Glu|Gly|Leu|Tyr|Gln|His|Phe|Lys|Ala|Ile|Ala|Glu|His|Thr|Asp|Leu|
| | |115| | | | |120| | | | |125| | | |
|Pro|Gln|Ile|Leu|Tyr|Asn|Val|Pro|Ser|Arg|Thr|Gly|Cys|Asp|Leu|Leu|
| |130| | | | |135| | | | |140| | | | |
|Pro|Glu|Thr|Val|Gly|Arg|Leu|Ala|Lys|Val|Lys|Asn|Ile|Ile|Gly|Ile|
|145| | | | |150| | | | |155| | | | |160|
|Lys|Glu|Ala|Thr|Gly|Asn|Leu|Thr|Arg|Val|Asn|Gln|Ile|Lys|Glu|Leu|
| | | | |165| | | | |170| | | | |175| |
|Val|Ser|Asp|Asp|Phe|Val|Leu|Leu|Ser|Gly|Asp|Asp|Ala|Ser|Ala|Leu|
| | | |180| | | | |185| | | | |190| | |
|Asp|Phe|Met|Gln|Leu|Gly|Gly|His|Gly|Val|Ile|Ser|Val|Thr|Ala|Asn|
| | |195| | | | |200| | | | |205| | | |
|Val|Ala|Ala|Arg|Asp|Met|Ala|Gln|Met|Cys|Lys|Leu|Ala|Ala|Glu|Gly|
| |210| | | | |215| | | | |220| | | | |
|His|Phe|Ala|Glu|Ala|Arg|Val|Ile|Asn|Gln|Arg|Leu|Met|Pro|Leu|His|
|225| | | | |230| | | | |235| | | | |240|
|Asn|Lys|Leu|Phe|Val|Glu|Pro|Asn|Pro|Ile|Pro|Val|Lys|Trp|Ala|Cys|
| | | | |245| | | | |250| | | | |255| |
|Lys|Glu|Leu|Gly|Leu|Val|Ala|Thr|Asp|Thr|Leu|Arg|Leu|Pro|Met|Thr|
| | | |260| | | | |265| | | | |270| | |
|Pro|Ile|Thr|Asp|Ser|Gly|Arg|Glu|Thr|Val|Arg|Ala|Ala|Leu|Lys|His|
| | |275| | | | |280| | | | |285| | | |
|Ala|Gly|Leu|Leu| | | | | | | | | | | | |
| |290| | | | | | | | | | | | | | |

<210> SEQ ID NO 24
<211> LENGTH: 1263
<212> TYPE: DNA
<213> ORGANISM: Escherichia coli

<400> SEQUENCE: 24

| | | | | | |
|---|---|---|---|---|---|
|atgccacatt|cactgttcag|caccgatacc|gatctcaccg|ccgaaaatct|gctgcgtttg|60|
|cccgctgaat|ttggctgccc|ggtgtgggtc|tacgatgcgc|aaattattcg|tcggcagatt|120|
|gcagcgctga|aacagtttga|tgtggtgcgc|tttgcacaga|agcctgttc|caatattcat|180|
|attttgcgct|taatgcgtga|gcagggcgtg|aaagtggatt|ccgtctcgtt|aggcgaaata|240|
|gagcgtgcgt|tggcggcggg|ttacaatccg|caaacgcacc|ccgatgatat|tgttttacg|300|
|gcagatgtta|tcgatcaggc|gacgcttgaa|cgcgtcagtg|aattgcaaat|tccggtgaat|360|

```
gcgggttctg ttgatatgct cgaccaactg ggccaggttt cgccagggca tcgggtatgg    420
ctgcgcgtta atccggggtt tggtcacgga catagccaaa aaaccaatac cggtggcgaa    480
aacagcaagc acggtatctg gtacaccgat ctgcccgccg cactggacgt gataacgt     540 catcatctgc agctggtcgg cattcacatg cacattggtt ctggcgttga ttatgcccat    600
ctggaacagg tgtgtggtgc tatggtgcgt caggtcatcg aattcggtca ggatttacag    660
gctatttctg cgggcggtgg gctttctgtt ccttatcaac agggtgaaga ggcggttgat    720
accgaacatt attatggtct gtggaatgcc gcgcgtgagc aaatcgcccg ccatttgggc    780
caccctgtga aactggaaat tgaaccgggt cgcttcctgg tagcgcagtc tggcgtatta    840
attactcagg tgcggagcgt caaacaaatg gggagccgcc actttgtgct ggttgatgcc    900
gggttcaacg atctgatgcg cccggcaatg tacggtagtt accaccatat cagtgccctg    960
gcagctgatg gtcgttctct ggaacacgcg ccaacggtgg aaaccgtcgt cgccggaccg   1020
ttatgtgaat cgggcgatgt ctttacccag caggaagggg gaaatgttga aaccccgcgcc   1080 ttgccggaag tgaaggcagg tgattatctg gtactgcatg atacaggggc atatggcgca   1140
tcaatgtcat ccaactacaa tagccgtccg ctgttaccag aagttctgtt tgataatggt   1200
caggcgcggt tgattcgccg tcgccagacc atcgaagaat tactggcgct ggaattgctt   1260
taa                                                                 1263
```

<210> SEQ ID NO 25
<211> LENGTH: 420
<212> TYPE: PRT
<213> ORGANISM: Escherichia coli

<400> SEQUENCE: 25

```
Met Pro His Ser Leu Phe Ser Thr Asp Thr Asp Leu Thr Ala Glu Asn
 1               5                  10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
            180                 185                 190

Gly Ser Gly Val Asp Tyr Ala His Leu Glu Gln Val Cys Gly Ala Met
        195                 200                 205
```

Val Arg Gln Val Ile Glu Phe Gly Gln Asp Leu Gln Ala Ile Ser Ala
    210                 215                 220

Gly Gly Gly Leu Ser Val Pro Tyr Gln Gln Gly Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
    290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
    370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 26
<211> LENGTH: 1350
<212> TYPE: DNA
<213> ORGANISM: Artificial
<220> FEATURE:
<223> OTHER INFORMATION: lysC-1 nucleic acid sequence

<400> SEQUENCE: 26
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag actggaacc tggcgagcga     180 ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca cggcgagctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540
acccagggat ttatcggtag cgaaaataaa ggtcgtacaa cgacgcttgg ccgtggaggc     600
agcgattata cggcagcctt gctggcggag gctttacacg catctcgtgt tgatatctgg     660
accgacgtcc cggcatcta caccaccgat ccacgcgtag tttccgcagc aaaacgcatt     720
gatgaaatcg cgtttgccga agcggcagag atggcaactt tggtgcaaaa gtactgcat      780

-continued

```
ccggcaacgt tgctacccgc agtacgcagc gatatcccgg tctttgtcgg ctccagcaaa    840
gacccacgcg caggtggtac gctgatgtgc aataaaactg aaaatccgcc gctgttccgc    900
gctctggcgc ttcgtcgcaa tcagactctg ctcactttgc acagcctgaa tatactgcat    960
tctcgcgatt tcctcgcgga agttttcggc atcctcgcgc ggcataatat ttcggtagac   1020
ttaatcacca cgtcagaagt gagcgtggca ttaacccttg ataccaccgg ttcaacctcc   1080
actggcgata cgttgctgac gcaatctctg ctgatggagc tttccgcact gtgtcgggtg   1140
gaggtggaag aaggtctggc gctggtcgcg ttgattggca atgacctgcc aaaagcctgc   1200
ggcgttggca agaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                     1350
```

<210> SEQ ID NO 27  
<211> LENGTH: 449  
<212> TYPE: PRT  
<213> ORGANISM: Artificial  
<220> FEATURE:  
<223> OTHER INFORMATION: LysC-1 polypeptide sequence

<400> SEQUENCE: 27

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
```

|  | 260 |  |  | 265 |  |  | 270 |  |  |  |
|--|--|--|--|--|--|--|--|--|--|--|

Pro Val Phe Val Gly Ser Ser Lys Asp Pro Arg Ala Gly Gly Thr Leu
        275           280          285

Val Cys Asn Lys Thr Glu Asn Pro Pro Leu Phe Arg Ala Leu Ala Leu
290               295            300

Arg Arg Asn Gln Thr Leu Leu Thr Leu His Ser Leu Asn Ile Leu His
305          310           315         320

Ser Arg Asp Phe Leu Ala Glu Val Phe Gly Ile Leu Ala Arg His Asn
        325           330          335

Ile Ser Val Asp Leu Ile Thr Thr Ser Glu Val Ser Val Ala Leu Thr
          340          345         350

Leu Asp Thr Thr Gly Ser Thr Ser Thr Gly Asp Thr Leu Leu Thr Gln
        355           360          365

Ser Leu Leu Met Glu Leu Ser Ala Leu Cys Arg Val Glu Val Glu Glu
          370          375         380

Gly Leu Ala Leu Val Ala Leu Ile Gly Asn Asp Leu Ser Lys Ala Cys
385          390           395         400

Gly Val Gly Lys Glu Val Phe Gly Val Leu Glu Pro Phe Asn Ile Arg
        405           410          415

Met Ile Cys Tyr Gly Ala Ser Ser His Asn Leu Cys Phe Leu Val Pro
          420          425         430

Gly Glu Asp Ala Glu Gln Val Val Gln Lys Leu His Ser Asn Leu Phe
        435           440          445

Glu

<210> SEQ ID NO 28
<211> LENGTH: 1272
<212> TYPE: DNA
<213> ORGANISM: Artificial
<220> FEATURE:
<223> OTHER INFORMATION: S-lysC nucleic acid sequence

<400> SEQUENCE: 28

| atgggcttag ttgtgcagaa atacggcggt agtagcgtgg ccgatgccga aggcatcaaa | 60 |
|---|---|
| cgtgttgcca acgcattgt tgaagccaaa aagaatggta tcaggttgt ggttgtcgtt | 120 |
| tcagcaatgg gcgataccac agatgaactt attgatctgg cccaggaagt tagccccgatt | 180 |
| ccgagcggtc gtgaatttga tatgttactt acagccggtg aacgtattag catggcctta | 240 |
| ctggccatgg caatcaaaaa tctgggtcac gaagcccaga gcttcacagg ttcacaggcc | 300 |
| ggtgttatta cagatagcgt tcataataaa gcgcgcatta tcgatgttac cccgggtcgt | 360 |
| attaaagcaa gcctggatga aggcaacatc gccattgtgg caggctttca gggtgttagc | 420 |
| caggataaaa aggatattac cacactgggt cgcggtggca gcgatacaac ggcagtggcc | 480 |
| ctggcagccg cattaaatgc agatgtttgt gaaatctata ccgatgttga tggtgttttt | 540 |
| accgcagatc cgcgcgtggt taagaaagcc cgtaaaattg aatggatctc attcgaagat | 600 |
| atgctggaat tagccagcag cggtagcaaa gttctgctgc atcgttgtgt tgaatatgca | 660 |
| cgccgttaca atattcctat tcatgttcgt tcaagttttt caggtttaca gggcacatgg | 720 |
| gttagcaatg aaccgcaggg tgatcgtccg atggaacagg caatcattag cggtgttgca | 780 |
| catgataccct cagaagcaaa agttaccgtt gttggtgttc cggataaacc gggcgaagca | 840 |
| gcacgtatct ttcgggccat tgccgattca gaagtgaata tcgacatggt ggttcagaat | 900 |
| gttagcgcag caagcaccgg tctgaccgat attagcttta ccctgccgaa agcagaaggt | 960 |

```
cgtaaagcag ttgcagcact ggagaaaacc cgtgcagccg tgggctttga tagtttacgg      1020
tatgatgatc agattgcaaa aattagcctg gttggtgcag gtatgaaaac caatccgggt      1080
gtgaccgcaa cctttttga agcattaagc aatgcaggcg ttaatattga actgattagc      1140
accagtgaaa ttcgtatcag cgttgtgacc cgcgcagatg atgttaatga agccgttcag      1200
gcagttcata gcgcatttgg tctggatagc gaaaccgatg aagcagtggt ttatggcggc      1260
acaggtcgtt aa                                                          1272
```

<210> SEQ ID NO 29
<211> LENGTH: 425
<212> TYPE: PRT
<213> ORGANISM: Streptomyces

<400> SEQUENCE: 29

```
Met Gly Leu Val Val Gln Lys Tyr Gly Gly Ser Ser Val Ala Asp Ala
1               5                   10                  15

Glu Gly Ile Lys Arg Val Ala Lys Arg Ile Val Glu Ala Lys Lys Asn
            20                  25                  30

Gly Asn Gln Val Val Ala Val Ser Ala Met Gly Asp Thr Thr Asp
        35                  40                  45

Glu Leu Ile Asp Leu Ala Glu Gln Val Ser Pro Ile Pro Ala Gly Arg
50                  55                  60

Glu Leu Asp Met Leu Leu Thr Ala Gly Glu Arg Ile Ser Met Ala Leu
65                  70                  75                  80

Leu Ala Met Ala Ile Lys Asn Leu Gly His Glu Ala Gln Ser Phe Thr
                85                  90                  95

Gly Ser Gln Ala Gly Val Ile Thr Asp Ser Val His Asn Lys Ala Arg
            100                 105                 110

Ile Ile Asp Val Thr Pro Gly Arg Ile Arg Thr Ser Val Asp Glu Gly
        115                 120                 125

Asn Val Ala Ile Val Ala Gly Phe Gln Gly Val Ser Gln Asp Ser Lys
    130                 135                 140

Asp Ile Thr Thr Leu Gly Arg Gly Gly Ser Asp Thr Thr Ala Val Ala
145                 150                 155                 160

Leu Ala Ala Ala Leu Asp Ala Asp Val Cys Glu Ile Tyr Thr Asp Val
                165                 170                 175

Asp Gly Val Phe Thr Ala Asp Pro Arg Val Pro Lys Ala Lys Lys
            180                 185                 190

Ile Asp Trp Ile Ser Phe Glu Asp Met Leu Glu Leu Ala Ala Ser Gly
        195                 200                 205

Ser Lys Val Leu Leu His Arg Cys Val Glu Tyr Ala Arg Arg Tyr Asn
    210                 215                 220

Ile Pro Ile His Val Arg Ser Ser Phe Ser Gly Leu Gln Gly Thr Trp
225                 230                 235                 240

Val Ser Ser Glu Pro Ile Lys Gln Gly Glu Lys His Val Glu Gln Ala
                245                 250                 255

Leu Ile Ser Gly Val Ala His Asp Thr Ser Glu Ala Lys Val Thr Val
            260                 265                 270

Val Gly Val Pro Asp Lys Pro Gly Glu Ala Ala Ile Phe Arg Ala
        275                 280                 285

Ile Ala Asp Ala Gln Val Asn Ile Asp Met Val Val Gln Asn Val Ser
    290                 295                 300

Ala Ala Ser Thr Gly Leu Thr Asp Ile Ser Phe Thr Leu Pro Lys Ser
305                 310                 315                 320
```

```
Glu Gly Arg Lys Ala Ile Asp Ala Leu Glu Lys Asn Arg Pro Gly Ile
                325                 330                 335

Gly Phe Asp Ser Leu Arg Tyr Asp Asp Gln Ile Gly Lys Ile Ser Leu
            340                 345                 350

Val Gly Ala Gly Met Lys Ser Asn Pro Gly Val Thr Ala Asp Phe Phe
        355                 360                 365

Thr Ala Leu Ser Asp Ala Gly Val Asn Ile Glu Leu Ile Ser Thr Ser
    370                 375                 380

Glu Ile Arg Ile Ser Val Val Thr Arg Lys Asp Asp Val Asn Glu Ala
385                 390                 395                 400

Val Arg Ala Val His Thr Ala Phe Gly Leu Asp Ser Asp Ser Asp Glu
                405                 410                 415

Ala Val Val Tyr Gly Gly Thr Gly Arg
            420                 425
```

<210> SEQ ID NO 30
<211> LENGTH: 1104
<212> TYPE: DNA
<213> ORGANISM: Escherichia coli

<400> SEQUENCE: 30

```
atgaaaaatg ttggttttat cggctggcgc ggtatggtcg gctccgttct catgcaacgc     60
atggttgaag agcgcgactt cgacgccatt cgccctgtct tcttttctac ttctcagctt    120
ggccaggctg cgccgtcttt tggcggaacc actggcacac ttcaggatgc ctttgatctg    180
gaggcgctaa aggccctcga tatcattgtg acctgtcagg gcggcgatta taccaacgaa    240
atctatccaa agcttcgtga agcggatggc aaggttact ggattgacgc agcatcgtct    300
ctgcgcatga agatgacgc catcatcatt cttgaccccg tcaatcagga cgtcattacc    360
gacggattaa ataatggcat caggactttt gttggcggta actgtaccgt aagcctgatg    420
ttgatgtcgt tggtggtttt attcgccaat gatcttgttg attgggtgtc cgttgcaacc    480
taccaggccg cttccggcgg tggtgcgcga catatgcgtg agttattaac ccagatgggc    540
catctgtatg ccatgtggc agatgaactc gcgaccccgt cctctgctat tctcgatatc    600
gaacgcaaag tcacaacctt aacccgtagc ggtgagctgc cggtggataa ctttggcgtg    660
ccgctggcgg gtagcctgat tccgtggatc gacaaacagc tcgataacgg tcagagccgc    720
gaagagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac ccagctgcc    960
gttaccggca cgctgaccac gccggtaggc cgcctgcgta agctgaatat gggaccagag   1020
ttcctgtcag cctttaccgt gggcgaccag ctgctgtggg gggccgcgga gccgctgcgt   1080
cggatgcttc gtcaactggc gtaa                                          1104
```

<210> SEQ ID NO 31
<211> LENGTH: 350
<212> TYPE: PRT
<213> ORGANISM: Escherichia coli

<400> SEQUENCE: 31

```
Met Lys Asn Val Gly Phe Ile Gly Trp Arg Gly Met Val Gly Ser Val
1               5                   10                  15
```

```
Leu Met Gln Arg Met Val Glu Glu Arg Asp Phe Asp Ala Ile Arg Pro
         20                  25                  30

Val Phe Phe Ser Thr Ser Gln Leu Gly Gln Ala Ala Pro Ser Phe Gly
             35                  40                  45

Gly Thr Gly Thr Leu Gln Asp Ala Phe Asp Leu Glu Ala Leu Lys
 50                  55                  60

Ala Leu Asp Ile Ile Val Thr Cys Gln Gly Gly Asp Tyr Thr Asn Glu
 65                  70                  75                  80

Ile Tyr Pro Lys Leu Arg Glu Ser Gly Trp Gln Gly Tyr Trp Ile Asp
             85                  90                  95

Ala Ala Ser Ser Leu Arg Met Lys Asp Asp Ala Ile Ile Ile Leu Asp
                100                 105                 110

Pro Val Asn Gln Asp Val Ile Thr Asp Gly Leu Asn Asn Gly Ile Arg
                115                 120                 125

Thr Phe Val Gly Gly Asn Cys Thr Val Ser Leu Met Leu Met Ser Leu
130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
                180                 185                 190

Pro Ser Ser Ala Ile Leu Asp Ile Glu Arg Lys Val Thr Thr Leu Thr
            195                 200                 205

Arg Ser Gly Glu Leu Pro Val Asp Asn Phe Gly Val Pro Leu Ala Gly
210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
                260                 265                 270

Cys His Ser Gln Ala Phe Thr Ile Lys Leu Lys Asp Val Ser Ile
            275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln
            340                 345                 350

<210> SEQ ID NO 32
<211> LENGTH: 822
<212> TYPE: DNA
<213> ORGANISM: Escherichia coli

<400> SEQUENCE: 32
atgcatgatg caaacatccg cgttgccatc gcgggagccg ggggcgtat gggccgccag      60 ttgattcagg cggcgctggc attagagggc gtgcagttgg gcgctgcgct ggagcgtgaa    120
ggatcttctt tactgggcag cgacgccggt gagctggccg gagccgggaa aacaggcgtt    180
accgtgcaaa gcagcctcga tgcggtaaaa gatgattttg atgtgtttat cgattttacc    240
```

```
cgtccggaag gtacgctgaa ccatctcgct ttttgtcgcc agcatggcaa agggatggtg    300
atcggcacta cggggtttga cgaagccggt aaacaagcaa ttcgtgacgc cgctgccgat    360
attgcgattg tctttgctgc caattttagc gttggcgtta acgtcatgct taagctgctg    420
gagaaagcag ccaaagtgat gggtgactac accgatatcg aaattattga agcacatcat    480
agacataaag ttgatgcgcc gtcaggcacc gcactggcaa tgggagaggc gatcgcccac    540
gcccttgata agatctgaa agattgcgcg gtctacagtc gtgaaggcca caccggtgaa    600
cgtgtgcctg gcaccattgg ttttgccacc gtgcgtgcag gtgacatcgt tggtgaacat    660
accgcgatgt ttgccgatat tggcgagcgt ctggagatca cccataaggc gtccagccgt    720
atgacatttg ctaacggcgc ggtaagatcg gctttgtggt tgagtggtaa ggaaagcggt    780
cttttttgata tgcgagatgt acttgatctc aataatttgt aa                     822
```

```
<210> SEQ ID NO 33
<211> LENGTH: 273
<212> TYPE: PRT
<213> ORGANISM: Escherichia coli

<400> SEQUENCE: 33

Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
            20                  25                  30

Leu Gly Ala Ala Leu Glu Arg Glu Gly Ser Ser Leu Leu Gly Ser Asp
        35                  40                  45

Ala Gly Glu Leu Ala Gly Ala Gly Lys Thr Gly Val Thr Val Gln Ser
    50                  55                  60

Ser Leu Asp Ala Val Lys Asp Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
            100                 105                 110

Ala Ile Arg Asp Ala Ala Ala Asp Ile Ala Ile Val Phe Ala Ala Asn
        115                 120                 125

Phe Ser Val Gly Val Asn Val Met Leu Lys Leu Leu Glu Lys Ala Ala
    130                 135                 140

Lys Val Met Gly Asp Tyr Thr Asp Ile Glu Ile Ile Glu Ala His His
145                 150                 155                 160

Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
    210                 215                 220

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270
```

Leu

<210> SEQ ID NO 34
<211> LENGTH: 825
<212> TYPE: DNA
<213> ORGANISM: Escherichia coli

<400> SEQUENCE: 34

```
atgcagcagt tacagaacat tattgaaacc gcttttgaac gccgtgccga gatcacgcca      60
gccaatgcag acaccgttac ccgcgaagcg gtaaatcagg tgatcgccct gctggattcc     120
ggcgcactgc gtgtagcgga aaaaattgac ggtcagtggg tgacgcatca gtggttgaaa     180
aaagcggtgc tgctctcttt ccgtattaat gataatcagg tgatcgaagg ggcagaaagc     240
cgctacttcg acaaagtgcc gatgaaattc gccgactacg acgaagcacg tttccagaaa     300
gaaggcttcc gcgttgtgcc accagcggcg gtacgtcagg gtgcgtttat tgcccgtaac     360
accgtgctga tgccgtctta cgtcaacatc ggcgcatatg ttgatgaagg caccatggtt     420
gatacctggg cgaccgtcgg ttcttgtgcg cagattggta aaaacgtcca cctttccggt     480
ggcgtgggca tcggcggcgt gctggaaccg ctgcaggcta acccaaccat cattgaagat     540
aattgcttca tcggcgcgcg ctctgaagtg gttgaagggg tgattgtcga agaaggttcc     600
gtcatttcca tgggcgtata cattggtcag agcacccgta tttacgaccg tgaaaccggc     660
gaaatccact acggtcgcgt tccggcgggg tctgtggttg tttcaggtaa tctgccgtca     720
aaagatggca atacagcct ctactgtgcg gttatcgtta agaaagttga cgcgaaaact     780
cgcggcaaag tcggcattaa cgaactgctg cgtaccatcg actaa                      825
```

<210> SEQ ID NO 35
<211> LENGTH: 274
<212> TYPE: PRT
<213> ORGANISM: Escherichia coli

<400> SEQUENCE: 35

```
Met Gln Gln Leu Gln Asn Ile Ile Glu Thr Ala Phe Glu Arg Arg Ala
1               5                   10                  15

Glu Ile Thr Pro Ala Asn Ala Asp Thr Val Thr Arg Glu Ala Val Asn
            20                  25                  30

Gln Val Ile Ala Leu Leu Asp Ser Gly Ala Leu Arg Val Ala Glu Lys
        35                  40                  45

Ile Asp Gly Gln Trp Val Thr His Gln Trp Leu Lys Lys Ala Val Leu
    50                  55                  60

Leu Ser Phe Arg Ile Asn Asp Asn Gln Val Ile Glu Gly Ala Glu Ser
65                  70                  75                  80

Arg Tyr Phe Asp Lys Val Pro Met Lys Phe Ala Asp Tyr Asp Glu Ala
                85                  90                  95

Arg Phe Gln Lys Glu Gly Phe Arg Val Val Pro Ala Ala Val Arg
            100                 105                 110

Gln Gly Ala Phe Ile Ala Arg Asn Thr Val Leu Met Pro Ser Tyr Val
        115                 120                 125

Asn Ile Gly Ala Tyr Val Asp Glu Gly Thr Met Val Asp Thr Trp Ala
    130                 135                 140

Thr Val Gly Ser Cys Ala Gln Ile Gly Lys Asn Val His Leu Ser Gly
145                 150                 155                 160

Gly Val Gly Ile Gly Gly Val Leu Glu Pro Leu Gln Ala Asn Pro Thr
                165                 170                 175
```

```
Ile Ile Glu Asp Asn Cys Phe Ile Gly Ala Arg Ser Glu Val Val Glu
            180                 185                 190

Gly Val Ile Val Glu Glu Gly Ser Val Ile Ser Met Gly Val Tyr Ile
        195                 200                 205

Gly Gln Ser Thr Arg Ile Tyr Asp Arg Glu Thr Gly Glu Ile His Tyr
    210                 215                 220

Gly Arg Val Pro Ala Gly Ser Val Val Ser Gly Asn Leu Pro Ser
225                 230                 235                 240

Lys Asp Gly Lys Tyr Ser Leu Tyr Cys Ala Val Ile Val Lys Lys Val
                245                 250                 255

Asp Ala Lys Thr Arg Gly Lys Val Gly Ile Asn Glu Leu Leu Arg Thr
            260                 265                 270

Ile Asp
```

<210> SEQ ID NO 36
<211> LENGTH: 1191
<212> TYPE: DNA
<213> ORGANISM: Escherichia coli

<400> SEQUENCE: 36

```
atgtttgaga acattaccgc cgctcctgcc gacccgattc tgggcctggc cgatctgttt      60
cgtgccgatg aacgtcccgg caaaattaac ctcgggattg gtgtctataa agatgagacg     120
ggcaaaaccc cggtactgac cagcgtgaaa aaggctgaac agtatctgct cgaaaatgaa     180
accaccaaaa attacctcgg cattgacggc atccctgaat ttggtcgctg cactcaggaa     240
ctgctgtttg gtaaaggtag cgccctgatc aatgacaaac gtgctcgcac ggcacagact     300
ccgggggggca ctggcgcact acgcgtggct gccgatttcc tggcaaaaaa taccagcgtt     360
aagcgtgtgt gggtgagcaa cccaagctgg ccgaaccata gagcgtcttt aactctgca      420
ggtctggaag ttcgtgaata cgcttattat gatgcggaaa tcacactct tgacttcgat      480
gcactgatta cagcctgaa tgaagctcag gctggcacg tagtgctgtt ccatggctgc      540
tgccataacc caaccggtat cgaccctacg ctggaacaat ggcaaacact ggcacaactc     600
tccgttgaga aaggctggtt accgctgttt gacttcgctt accagggttt tgcccgtggt     660
ctggaagaag atgctgaagg actgcgcgct ttcgcggcta tgcataaaga gctgattgtt     720
gccagttcct actctaaaaa cttttggcctg tacaacgagc gtgttggcgc ttgtactctg     780
gttgctgccg acagtgaaac cgttgatcgc gcattcagcc aaatgaaagc ggcgattcgc     840
gctaactact ctaacccacc agcacacggc gcttctgttg ttgccaccat cctgagcaac     900
gatgcgttac gtgcgatttg ggaacaagag ctgactgata tgcgccagcg tattcagcgt     960
atgcgtcagt tgttcgtcaa tacgctgcag gaaaaaggcg caaaccgcga cttcagcttt    1020
atcatcaaac agaacggcat gttctccttc agtggcctga caaagaaaca gtgctgcgt    1080
ctgcgcgaag agtttggcgt atatgcggtt gcttctggtc gcgtaaatgt ggccgggatg    1140
acaccagata acatggctcc gctgtgcgaa gcgattgtgg cagtgctgta a             1191
```

<210> SEQ ID NO 37
<211> LENGTH: 396
<212> TYPE: PRT
<213> ORGANISM: Escherichia coli

<400> SEQUENCE: 37

```
Met Phe Glu Asn Ile Thr Ala Ala Pro Ala Asp Pro Ile Leu Gly Leu
1               5                   10                  15
```

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45

Val Lys Lys Ala Glu Gln Tyr Leu Leu Glu Asn Glu Thr Thr Lys Asn
 50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
            100                 105                 110

Phe Leu Ala Lys Asn Thr Ser Val Lys Arg Val Trp Val Ser Asn Pro
        115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
    210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270

Ser Gln Met Lys Ala Ala Ile Arg Ala Asn Tyr Ser Asn Pro Pro Ala
        275                 280                 285

His Gly Ala Ser Val Val Ala Thr Ile Leu Ser Asn Asp Ala Leu Arg
    290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365

Ala Val Ala Ser Gly Arg Val Asn Val Ala Gly Met Thr Pro Asp Asn
    370                 375                 380

Met Ala Pro Leu Cys Glu Ala Ile Val Ala Val Leu
385                 390                 395

<210> SEQ ID NO 38
<211> LENGTH: 299
<212> TYPE: PRT
<213> ORGANISM: Escherichia coli

<400> SEQUENCE: 38

```
Met Phe Ser Gly Leu Leu Ile Ile Leu Val Pro Leu Ile Val Gly Tyr
1               5                   10                  15

Leu Ile Pro Leu Arg Gln Ala Ala Leu Lys Val Ile Asn Gln Leu
            20                  25                  30

Leu Ser Trp Met Val Tyr Leu Ile Leu Phe Phe Met Gly Ile Ser Leu
        35                  40                  45

Ala Phe Leu Asp Asn Leu Ala Ser Asn Leu Leu Ala Ile Leu His Tyr
50                      55                      60

Ser Ala Val Ser Ile Thr Val Ile Leu Leu Cys Asn Ile Ala Ala Leu
65                  70                  75                  80

Met Trp Leu Glu Arg Gly Leu Pro Trp Arg Asn His His Gln Gln Glu
                85                  90                  95

Lys Leu Pro Ser Arg Ile Ala Met Ala Leu Glu Ser Leu Lys Leu Cys
            100                 105                 110

Gly Val Val Ile Gly Phe Ala Ile Gly Leu Ser Gly Leu Ala Phe
        115                 120                 125

Leu Gln His Ala Thr Glu Ala Ser Glu Tyr Thr Leu Ile Leu Leu Leu
130                 135                 140

Phe Leu Val Gly Ile Gln Leu Arg Asn Asn Gly Met Thr Leu Lys Gln
145                 150                 155                 160

Ile Val Leu Asn Arg Arg Gly Met Ile Val Ala Val Val Val Val
                165                 170                 175

Ser Ser Leu Ile Gly Gly Leu Ile Asn Ala Phe Ile Leu Asp Leu Pro
            180                 185                 190

Ile Asn Thr Ala Leu Ala Met Ala Ser Gly Phe Gly Trp Tyr Ser Leu
            195                 200                 205

Ser Gly Ile Leu Leu Thr Glu Ser Phe Gly Pro Val Ile Gly Ser Ala
        210                 215                 220

Ala Phe Phe Asn Asp Leu Ala Arg Glu Leu Ile Ala Ile Met Leu Ile
225                 230                 235                 240

Pro Gly Leu Ile Arg Arg Ser Arg Ser Thr Ala Leu Gly Leu Cys Gly
            245                 250                 255

Ala Thr Ser Met Asp Phe Thr Leu Pro Val Leu Gln Arg Thr Gly Gly
            260                 265                 270

Leu Asp Met Val Pro Ala Ala Ile Val His Gly Phe Ile Leu Ser Leu
        275                 280                 285

Leu Val Pro Ile Leu Ile Ala Phe Phe Ser Ala
    290                 295

<210> SEQ ID NO 39
<211> LENGTH: 52
<212> TYPE: DNA
<213> ORGANISM: Artificial
<220> FEATURE:
<223> OTHER INFORMATION: primer

<400> SEQUENCE: 39
ggcgagctca cacaggaaac agaccatgaa cgttattgca atattgaatc ac        52

<210> SEQ ID NO 40
<211> LENGTH: 28
<212> TYPE: DNA
<213> ORGANISM: Artificial
<220> FEATURE:
<223> OTHER INFORMATION: primer

<400> SEQUENCE: 40
```
ggctctagac cacttccctt gtacgagc                                28

<210> SEQ ID NO 41
<211> LENGTH: 45
<212> TYPE: DNA
<213> ORGANISM: Artificial
<220> FEATURE:
<223> OTHER INFORMATION: primer

<400> SEQUENCE: 41
ggcgagctca cacaggaaac agaccatgaa aaagacagct atcgc              45

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42
ggctctagaa ccagacgaga acttaagcc                                29

<210> SEQ ID NO 43
<211> LENGTH: 49
<212> TYPE: DNA
<213> ORGANISM: Artificial
<220> FEATURE:
<223> OTHER INFORMATION: primer

<400> SEQUENCE: 43
ggcgagctca cacaggaaac agaccatgaa agttaaagta ctgtccctc          49

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
ggctctagat tagaactggt aaaccagacc                               30

<210> SEQ ID NO 45
<211> LENGTH: 46
<212> TYPE: DNA
<213> ORGANISM: Artificial
<220> FEATURE:
<223> OTHER INFORMATION: primer

<400> SEQUENCE: 45
ggcgagctca cacaggaaac agaccatgat gaagcgcaat attctg             46

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
ggctctagag catttaacaa agaggtgtgc                               30

<210> SEQ ID NO 47
<211> LENGTH: 50
<212> TYPE: DNA

<213> ORGANISM: Artificial
<220> FEATURE:
<223> OTHER INFORMATION: primer

<400> SEQUENCE: 47
ggcgagctca cacaggaaac agaccatgaa aaaaattgca tgtctttcag    50

<210> SEQ ID NO 48
<211> LENGTH: 29
<212> TYPE: DNA
<213> ORGANISM: Artificial
<220> FEATURE:
<223> OTHER INFORMATION: primer

<400> SEQUENCE: 48
ggctctagat tagaagcggt aaccaacac    29

<210> SEQ ID NO 49
<211> LENGTH: 45
<212> TYPE: DNA
<213> ORGANISM: Artificial
<220> FEATURE:
<223> OTHER INFORMATION: primer

<400> SEQUENCE: 49
ggcgagctca cacaggaaac agaccatgaa aaagagcact ctggc    45

<210> SEQ ID NO 50
<211> LENGTH: 33
<212> TYPE: DNA
<213> ORGANISM: Artificial
<220> FEATURE:
<223> OTHER INFORMATION: primer

<400> SEQUENCE: 50
ggctctagat taaaactgat acgtcatgcc aac    33

<210> SEQ ID NO 51
<211> LENGTH: 49
<212> TYPE: DNA
<213> ORGANISM: Artificial
<220> FEATURE:
<223> OTHER INFORMATION: primer

<400> SEQUENCE: 51
ggcgagctca cacaggaaac agaccatgaa aaagttatta ccctgtacc    49

<210> SEQ ID NO 52
<211> LENGTH: 29
<212> TYPE: DNA
<213> ORGANISM: Artificial
<220> FEATURE:
<223> OTHER INFORMATION: primer

<400> SEQUENCE: 52
ggctctagat cagaacgagt aatttacgc    29

<210> SEQ ID NO 53
<211> LENGTH: 46
<212> TYPE: DNA
<213> ORGANISM: Artificial
<220> FEATURE:
<223> OTHER INFORMATION: primer

<400> SEQUENCE: 53
ggcgagctca cacaggaaac agaccatgaa aaagttaaca gtggcg    46

-continued

```
<210> SEQ ID NO 54
<211> LENGTH: 31
<212> TYPE: DNA
<213> ORGANISM: Artificial
<220> FEATURE:
<223> OTHER INFORMATION: primer

<400> SEQUENCE: 54
ggctctagat taaaaacgat atcctgctga g                              31

<210> SEQ ID NO 55
<211> LENGTH: 66
<212> TYPE: DNA
<213> ORGANISM: Artificial
<220> FEATURE:
<223> OTHER INFORMATION: primer

<400> SEQUENCE: 55
ggcgaattca gtttattctt gacatgtagt gaggggggctg gtataatgag ctcggtaccc   60
gggggat                                                          66

<210> SEQ ID NO 56
<211> LENGTH: 34
<212> TYPE: DNA
<213> ORGANISM: Artificial
<220> FEATURE:
<223> OTHER INFORMATION: primer

<400> SEQUENCE: 56
ggcagtactc aaccaagtca ttctgagaat agtg                            34

<210> SEQ ID NO 57
<211> LENGTH: 49
<212> TYPE: DNA
<213> ORGANISM: Artificial
<220> FEATURE:
<223> OTHER INFORMATION: primer

<400> SEQUENCE: 57
ggcgagctca cacaggaaac agaccatgaa atctaacaat gcgctcatc             49

<210> SEQ ID NO 58
<211> LENGTH: 29
<212> TYPE: DNA
<213> ORGANISM: Artificial
<220> FEATURE:
<223> OTHER INFORMATION: primer

<400> SEQUENCE: 58
ggctctagat caacgacagg agcacgatc                                  29

<210> SEQ ID NO 59
<211> LENGTH: 46
<212> TYPE: DNA
<213> ORGANISM: Artificial
<220> FEATURE:
<223> OTHER INFORMATION: primer

<400> SEQUENCE: 59
ggcgagctca cacaggaaac agaccatgtc tgaaattgtt gtctcc                46

<210> SEQ ID NO 60
<211> LENGTH: 33
<212> TYPE: DNA
```

```
<213> ORGANISM: Artificial
<220> FEATURE:
<223> OTHER INFORMATION: primer

<400> SEQUENCE: 60
ggcggatcct tactcaaaca aattactatg cag                              33

<210> SEQ ID NO 61
<211> LENGTH: 46
<212> TYPE: DNA
<213> ORGANISM: Artificial
<220> FEATURE:
<223> OTHER INFORMATION: primer

<400> SEQUENCE: 61
ggcggatcca cacaggaaac agaccatgtt cacgggaagt attgtc                46

<210> SEQ ID NO 62
<211> LENGTH: 28
<212> TYPE: DNA
<213> ORGANISM: Artificial
<220> FEATURE:
<223> OTHER INFORMATION: primer

<400> SEQUENCE: 62
ggctctagat tacagcaaac cggcatgc                                    28

<210> SEQ ID NO 63
<211> LENGTH: 46
<212> TYPE: DNA
<213> ORGANISM: Artificial
<220> FEATURE:
<223> OTHER INFORMATION: primer

<400> SEQUENCE: 63
ggctctagaa cacaggaaac agaccatgcc acattcactg ttcagc                46

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
ggcgtcgact taaagcaatt ccagcgccag                                  30

<210> SEQ ID NO 65
<211> LENGTH: 34
<212> TYPE: DNA
<213> ORGANISM: Artificial
<220> FEATURE:
<223> OTHER INFORMATION: primer

<400> SEQUENCE: 65
ggcctcgaga gtttattctt gacatgtagt gagg                             34

<210> SEQ ID NO 66
<211> LENGTH: 29
<212> TYPE: DNA
<213> ORGANISM: Artificial
<220> FEATURE:
<223> OTHER INFORMATION: primer

<400> SEQUENCE: 66
ggcgcatgct caacgacagg agcacgatc                                   29
```

<210> SEQ ID NO 67
<211> LENGTH: 23
<212> TYPE: DNA
<213> ORGANISM: Artificial
<220> FEATURE:
<223> OTHER INFORMATION: primer

<400> SEQUENCE: 67
cagcctgaat atactgcatt ctc                                              23

<210> SEQ ID NO 68
<211> LENGTH: 23
<212> TYPE: DNA
<213> ORGANISM: Artificial
<220> FEATURE:
<223> OTHER INFORMATION: primer

<400> SEQUENCE: 68
gagaatgcag tatattcagg ctg                                              23

<210> SEQ ID NO 69
<211> LENGTH: 20
<212> TYPE: DNA
<213> ORGANISM: Artificial
<220> FEATURE:
<223> OTHER INFORMATION: primer

<400> SEQUENCE: 69
gcattctcgc gatttcctcg                                                  20

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
cgaggaaatc gcgagaatgc                                                  20

<210> SEQ ID NO 71
<211> LENGTH: 46
<212> TYPE: DNA
<213> ORGANISM: Artificial
<220> FEATURE:
<223> OTHER INFORMATION: primer

<400> SEQUENCE: 71
ggcgagctca cacaggaaac agaccatggg cttagttgtg cagaaa                     46

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
ggcggatcct taacgacctg tgccgccata                                       30

<210> SEQ ID NO 73
<211> LENGTH: 48
<212> TYPE: DNA
<213> ORGANISM: Artificial
<220> FEATURE:

<223> OTHER INFORMATION: primer

<400> SEQUENCE: 73
ggcgagctca cacaggaaac agaccatgaa aaatgttggt tttatcgg                    48

<210> SEQ ID NO 74
<211> LENGTH: 28
<212> TYPE: DNA
<213> ORGANISM: Artificial
<220> FEATURE:
<223> OTHER INFORMATION: primer

<400> SEQUENCE: 74
ggcggatcct tacgccagtt gacgaagc                                          28

<210> SEQ ID NO 75
<211> LENGTH: 39
<212> TYPE: DNA
<213> ORGANISM: Artificial
<220> FEATURE:
<223> OTHER INFORMATION: primer

<400> SEQUENCE: 75
ggcacacagg aaacagacca tgcatgatgc aaacatccg                              39

<210> SEQ ID NO 76
<211> LENGTH: 38
<212> TYPE: DNA
<213> ORGANISM: Artificial
<220> FEATURE:
<223> OTHER INFORMATION: primer

<400> SEQUENCE: 76
ggctctagat tacaaattat tgagatcaag tacatctc                               38

<210> SEQ ID NO 77
<211> LENGTH: 45
<212> TYPE: DNA
<213> ORGANISM: Artificial
<220> FEATURE:
<223> OTHER INFORMATION: primer

<400> SEQUENCE: 77
ggctctagaa cacaggaaac agaccatgca gcagttacag aacat                       45

<210> SEQ ID NO 78
<211> LENGTH: 29
<212> TYPE: DNA
<213> ORGANISM: Artificial
<220> FEATURE:
<223> OTHER INFORMATION: primer

<400> SEQUENCE: 78
ggcgcatgct tagtcgatgg tacgcagca                                         29

<210> SEQ ID NO 79
<211> LENGTH: 46
<212> TYPE: DNA
<213> ORGANISM: Artificial
<220> FEATURE:
<223> OTHER INFORMATION: primer

<400> SEQUENCE: 79
ggctctagaa cacaggaaac agaccatgtt tgagaacatt accgcc                      46

```
<210> SEQ ID NO 80
<211> LENGTH: 47
<212> TYPE: DNA
<213> ORGANISM: Artificial
<220> FEATURE:
<223> OTHER INFORMATION: primer

<400> SEQUENCE: 80
ggcgcatgcg acctcgaggt agtcgactta cagcactgcc acaatcg          47

<210> SEQ ID NO 81
<211> LENGTH: 34
<212> TYPE: DNA
<213> ORGANISM: Artificial
<220> FEATURE:
<223> OTHER INFORMATION: primer

<400> SEQUENCE: 81
ggcggtacca gtttattctt gacatgtagt gagg                        34

<210> SEQ ID NO 82
<211> LENGTH: 29
<212> TYPE: DNA
<213> ORGANISM: Artificial
<220> FEATURE:
<223> OTHER INFORMATION: primer

<400> SEQUENCE: 82
ggcgggccct taaagcaatt ccagcgcca                              29

<210> SEQ ID NO 83
<211> LENGTH: 29
<212> TYPE: DNA
<213> ORGANISM: Artificial
<220> FEATURE:
<223> OTHER INFORMATION: primer

<400> SEQUENCE: 83
ggcgggccct gctggccttt tgctcacat                              29

<210> SEQ ID NO 84
<211> LENGTH: 29
<212> TYPE: DNA
<213> ORGANISM: Artificial
<220> FEATURE:
<223> OTHER INFORMATION: primer

<400> SEQUENCE: 84
ggcggtacct caacgacagg agcacgatc                              29

<210> SEQ ID NO 85
<211> LENGTH: 34
<212> TYPE: DNA
<213> ORGANISM: Artificial
<220> FEATURE:
<223> OTHER INFORMATION: primer

<400> SEQUENCE: 85
ggcggtacca gtttattctt gacatgtagt gagg                        34

<210> SEQ ID NO 86
<211> LENGTH: 29
<212> TYPE: DNA
<213> ORGANISM: Artificial
<220> FEATURE:
<223> OTHER INFORMATION: primer
```

<400> SEQUENCE: 86
ggcgggccct taaagcaatt ccagcgcca                                                29

<210> SEQ ID NO 87
<211> LENGTH: 45
<212> TYPE: DNA
<213> ORGANISM: Artificial
<220> FEATURE:
<223> OTHER INFORMATION: primer

<400> SEQUENCE: 87
ggctctagaa cacaggaaac agaccatgaa aaagacagct atcgc                              45

<210> SEQ ID NO 88
<211> LENGTH: 29
<212> TYPE: DNA
<213> ORGANISM: Artificial
<220> FEATURE:
<223> OTHER INFORMATION: primer

<400> SEQUENCE: 88
ggcaagctta ccagacgaga acttaagcc                                                29

<210> SEQ ID NO 89
<211> LENGTH: 49
<212> TYPE: DNA
<213> ORGANISM: Artificial
<220> FEATURE:
<223> OTHER INFORMATION: primer

<400> SEQUENCE: 89
ggctctagaa cacaggaaac agaccatgaa agttaaagta ctgtccctc                          49

<210> SEQ ID NO 90
<211> LENGTH: 30
<212> TYPE: DNA
<213> ORGANISM: Artificial
<220> FEATURE:
<223> OTHER INFORMATION: primer

<400> SEQUENCE: 90
ggcaagcttt tagaactggt aaaccagacc                                               30

<210> SEQ ID NO 91
<211> LENGTH: 46
<212> TYPE: DNA
<213> ORGANISM: Artificial
<220> FEATURE:
<223> OTHER INFORMATION: primer

<400> SEQUENCE: 91
ggctctagaa cacaggaaac agaccatgat gaagcgcaat attctg                             46

<210> SEQ ID NO 92
<211> LENGTH: 30
<212> TYPE: DNA
<213> ORGANISM: Artificial
<220> FEATURE:
<223> OTHER INFORMATION: primer

<400> SEQUENCE: 92
ggcaagcttg catttaacaa agaggtgtgc                                               30

<210> SEQ ID NO 93
<211> LENGTH: 50

<212> TYPE: DNA
<213> ORGANISM: Artificial
<220> FEATURE:
<223> OTHER INFORMATION: primer

<400> SEQUENCE: 93
ggctctagaa cacaggaaac agaccatgaa aaaaattgca tgtctttcag        50

<210> SEQ ID NO 94
<211> LENGTH: 29
<212> TYPE: DNA
<213> ORGANISM: Artificial
<220> FEATURE:
<223> OTHER INFORMATION: primer

<400> SEQUENCE: 94
ggcaagcttt tagaagcggt aaccaacac        29

<210> SEQ ID NO 95
<211> LENGTH: 45
<212> TYPE: DNA
<213> ORGANISM: Artificial
<220> FEATURE:
<223> OTHER INFORMATION: primer

<400> SEQUENCE: 95
ggctctagaa cacaggaaac agaccatgaa aaagagcact ctggc        45

<210> SEQ ID NO 96
<211> LENGTH: 33
<212> TYPE: DNA
<213> ORGANISM: Artificial
<220> FEATURE:
<223> OTHER INFORMATION: primer

<400> SEQUENCE: 96
ggcaagcttt taaaactgat acgtcatgcc aac        33

<210> SEQ ID NO 97
<211> LENGTH: 49
<212> TYPE: DNA
<213> ORGANISM: Artificial
<220> FEATURE:
<223> OTHER INFORMATION: primer

<400> SEQUENCE: 97
ggctctagaa cacaggaaac agaccatgaa aaagttatta ccctgtacc        49

<210> SEQ ID NO 98
<211> LENGTH: 29
<212> TYPE: DNA
<213> ORGANISM: Artificial
<220> FEATURE:
<223> OTHER INFORMATION: primer

<400> SEQUENCE: 98
ggcaagcttt cagaacgagt aatttacgc        29

<210> SEQ ID NO 99
<211> LENGTH: 46
<212> TYPE: DNA
<213> ORGANISM: Artificial
<220> FEATURE:
<223> OTHER INFORMATION: primer

<400> SEQUENCE: 99

```
ggctctagaa cacaggaaac agaccatgaa aaagttaaca gtggcg                46
```

<210> SEQ ID NO 100
<211> LENGTH: 31
<212> TYPE: DNA
<213> ORGANISM: Artificial
<220> FEATURE:
<223> OTHER INFORMATION: primer

<400> SEQUENCE: 100

```
ggcaagcttt taaaaacgat atcctgctga g                                31
```

<210> SEQ ID NO 101
<211> LENGTH: 47
<212> TYPE: DNA
<213> ORGANISM: Artificial
<220> FEATURE:
<223> OTHER INFORMATION: primer

<400> SEQUENCE: 101

```
ggctctagaa cacaggaaac agaccatgtt ttctgggctg ttaatca               47
```

<210> SEQ ID NO 102
<211> LENGTH: 29
<212> TYPE: DNA
<213> ORGANISM: Artificial
<220> FEATURE:
<223> OTHER INFORMATION: primer

<400> SEQUENCE: 102

```
ggcaagcttg atctaccgcc agagaggta                                   29
```

MODIFIED MEMBRANE PERMEABILITY

BACKGROUND OF THE INVENTION

Transporters are important in the production of amino acid and amino acid derived products because they transport compounds into and out of the cell, thereby influencing the intracellular concentration of these molecules. A high concentration inside the cell leads to feedback inhibition, which negatively affects production. For example, although feedback inhibition has been observed in lysC during lysine biosynthesis, feedback-resistant mutants were able to function in the presence of high concentrations of lysine (Kikuchi et al., *FEMS Microbiology Letters* 173:211-215, 1999; Ogawa-Miyata et al., *Biosci. Biotechnol. Biochem.* 65:1149-1154, 2001). Such feedback resistant mutants are able to generate higher lysine titers. Transport of molecules out of the cells can also reduce the effects of feedback inhibition.

Previous studies of the production of amino acids, such as lysine, and amino acid-derived products, such as cadaverine, focus on the overexpression or attenuation of genes involved in cellular metabolism. These modifications increase fluxes that lead to the production of the desired product, and decrease fluxes that lead to the production of side products or other metabolites not necessary for the formation of the desired product. However, additional methods of increasing the production of amino acids and their derived productions are needed.

BRIEF SUMMARY OF ASPECTS OF THE INVENTION

This invention is based, in part, on the surprising discovery that outer membrane porin proteins that are not specific for amino acids, such as OmpA, OmpC, OmpF, OmpX, OmpE, OmpG, and OmpW proteins, affect the production of an amino acid, e.g., lysine, and its derived products, e.g., cadaverine. Thus, in one aspect, the invention provides a genetically modified microorganism in which an outer membrane porin polypeptide, e.g., OmpA, OmpC, OmpF, OmpX, OmpE, OmpG, and OmpW, is overexpressed relative to a counterpart microorganism of the same strain that does not comprise the genetic modification. In some embodiments, the microorganism is genetically modified by introducing an expression vector comprising a nucleic acid sequence that encodes the porin polypeptide into the microorganism. In some embodiments, the microorganism is genetically modified to overexpress an endogenous outermembrane porin polypeptide, e.g., by introducing multiple copies of a gene encoding the endogenous porin polypeptide into the genome and/or by increasing expression of an endogenous gene using a heterologous promoter.

In one aspect, the invention provides a genetically modified host cell comprising a heterologous nucleic acid encoding an OMP porin polypeptide, wherein the host cell overexpresses the OMP porin polypeptide and has increased production of an amino acid or its derivative relative to an unmodified counterpart host cell. In some embodiments, the OMP porin polypeptide is an OmpA, OmpC, OmpF, OmpX, OmpE, OmpG, or OmpW porin polypeptide. In some embodiments, the OMP porin polypeptide has at least 70% identity, or at least 75%, 80%, 85%, 90%, or 95% identity to the region of SEQ ID NO:4, 6, 8, 10, 12, 14, or 16 that encodes the mature OMP porin polypeptide. In some embodiments, the heterologous nucleic acid encoding the OMP porin polypeptide is encoded by an expression vector introduced into the cell, wherein the expression vector comprises the heterologous nucleic acid operably linked to a promoter. In some embodiments, the OMP porin polypeptide is endogenous to the host cell. In some embodiments, the heterologous nucleic acid is integrated into the host chromosome. In some embodiments, the genetically modified host cell host cell overexpresses a lysine decarboxylase and/or one or more lysine biosynthesis polypeptides. In some embodiments, the host cell overexpresses a TetA polypeptide. In some embodiments, the host cell is of the genus *Escherichia, Hafnia*, or *Corynebacterium*. In some embodiments, the host cell is *Escherichia coli, Hafnia alvei*, or *Corynebacterium glutamicum*. In some embodiments, the Omp porin polypeptide is an OmpA, OmpC, OmpF, or OmpW polypeptide. In some embodiments, the host cell overexpresses a LysC, DapA, LysA, Asd, DapB, AspC, and TetA polypeptide. In some embodiments, the amino acid is lysine and the amino acid derivative is cadaverine.

In a further aspect, the invention provides a method of producing an amino acid or its derivative, the method comprising culturing a genetically modified host cell as described herein, e.g., as described in the preceding paragraph under conditions in which the OMP porin polypeptide is overexpressed. In some embodiments, the amino acid is lysine and the amino acid derivative is cadaverine.

In another aspect, the invention provides a method of engineering a host cell to increase production of an amino acid or its derivative, the method comprising introduce a heterologous nucleic acid encoding an OMP porin polypeptide into the host cell, and culturing the host cell under conditions in which the heterologous OMP prion polypeptide is expressed, wherein expression of the OMP porin polypeptide increases the production of lysine or a lysine derivative relative to an unmodified counterpart control host cell. In some embodiments, the OMP porin polypeptide is an OmpA, OmpC, OmpF, OmpX, OmpE, OmpG, or OmpW porin polypeptide. In some embodiments, the OMP porin polypeptide has at least 70% identity, or at least 75%, 80%, 85%, 90%, or 95% identity to the region of SEQ ID NO:4, 6, 8, 10, 12, 14, or 16 that encodes the mature OMP porin polypeptide. In some embodiments, the heterologous nucleic acid encoding the OMP porin polypeptide is encoded by an expression vector introduced into the cell, wherein the expression vector comprises the heterologous nucleic acid operably linked to a promoter. In some embodiments, the OMP porin polypeptide is endogenous to the host cell. In some embodiments, the heterologous nucleic acid is integrated into the host chromosome. In some embodiments, the host cell overexpresses a lysine decarboxylase and/or one or more lysine biosynthesis polypeptides. In some embodiments, the host cell overexpresses a TetA polypeptide. In some embodiments, the host cell is of the genus *Escherichia, Hafnia*, or *Corynebacterium*. In some embodiments, the host cell is *Escherichia coli, Hafnia alvei*, or *Corynebacterium glutamicum*. In some embodiments, the Omp porin polypeptide is an OmpA, OmpC, OmpF, or OmpW polypeptide. In some embodiments, the host cell overexpresses a lysine decarboxylase polypeptide and a LysC, DapA, LysA, Asd, DapB, and/or AspC; and a TetA polypeptide. In some embodiments, the amino acid is lysine and the amino acid derivative is cadaverine.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Definitions

As used herein, the term "outer membrane porin" polypeptide or "OMP" polypeptide refers to an outer membrane transporter polypeptide that transports amino acids, e.g., lysine, or an amino acid derivative, e.g., cadaverine, into and out of the cell, but is not specific for the transport of the amino acid or its derivative. Outer membrane porin polypeptides are well known and have been extensively characterized (see, e.g., Galdiero et al, 2012 for a review). Structural features include the presence of an 8-, 14-, 16-, or 18-stranded antiparallel beta barrel. The β strands are, in general, linked together by beta turns on the cytoplasmic side and long loops of amino acids on the other. X-ray structure analyses of several bacterial porins show an 8-, 12-, 14-, 16-, or 18-stranded anti-parallel beta-barrel structure enclosing the transmembrane pore. The term "OMP polypeptide" encompasses biologically active variants, alleles, mutants, and interspecies homologs to the specific polypeptides described herein. A nucleic acid that encodes an OMP porin polypeptide refers to a gene, pre-mRNA, mRNA, and the like, including nucleic acids encoding variants, alleles, mutants, and interspecies homologs of the particular amino acid sequences described herein. In some embodiments, an Omp porin polypeptide of the invention is an OmpA, OmpC, OmpF, OmpE, OmpG, OmpX, or OmpW porin polypeptide.

An "OmpA porin" polypeptide refers to a biologically active variant, alleles, mutant, and interspecies homolog of an *Escherichia coli* OmpA polypeptide having the amino acid sequence of SEQ ID NO:4. Illustrative OmpA polypeptides from other species include *Enterobacteriaceae* sp. protein sequence accession number WP_000750416.1; *Shigella* sp. protein sequence accession number WP_005047463.1; *Citrobacter farmeri* protein sequence accession number GAL49133.1; *Salmonella enterica* protein sequence accession number EHB41176.1; and *Cronobacter muytjensli* protein sequence accession number WP_038863759.1 An "OmpA porin" polypeptide has at least 60% amino acid sequence identity, typically at least 65%, 70%, 75%, 80%, 85%, 90%, 91%, 92%, 93%, 94%, 95%, 96%, 97%, 98% or 99% or greater amino acid sequence identity, preferably over a region of at least about 100, 200, 250, or 300, or more, amino acids, or over the length of the mature OmpA polypeptide of SEQ ID NO:4. An "OmpA porin polynucleotide" as used herein refers to a polynucleotide that encodes an OmpA porin polypeptide.

An "OmpC porin" polypeptide refers to a biologically active variant, alleles, mutant, and interspecies homolog of an *Escherichia coli* OmpC polypeptide having the amino acid sequence of SEQ ID NO:8. Illustrative OmpC polypeptides from other species include *Enterobacteriaceae* sp. protein sequence accession number WP_000865568.1; *Shigella* sp. protein sequence accession number WP_00865596.1; *Citrobacter freundii* protein sequence accession number WP_032944041.1; and *Klebsiella* sp. protein sequence accession number WP_004103993.1. An "OmpC porin" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 100, 200, 250, 300, or more, amino acids, or over the length of the mature OmpC polypeptide of SEQ ID NO:6. An "OmpC porin polynucleotide" as used herein refers to a polynucleotide that encodes an OmpC porin polypeptide.

An "OmpF porin" polypeptide refers to a biologically active variant, alleles, mutant, and interspecies homolog of an *Escherichia coli* OmpF polypeptide having the amino acid sequence of SEQ ID NO:8. Illustrative OmpF polypeptides from other species include *Enterobacteriaceae* sp. protein sequence accession number WP_001340338.1; *Shigella* sp. protein sequence accession number WP_000977934.1; *Citrobacter koseri* protein sequence accession number WP_012132994.1; and *Cronobacter malonaticus* protein sequence accession number WP_032974332.1. An "OmpF porin" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 100, 200, 250, 300, or more, amino acids, or over the length of the mature OmpF polypeptide of SEQ ID NO:8. An "OmpF porin polynucleotide" as used herein refers to a polynucleotide that encodes an OmpF porin polypeptide.

An "OmpX porin" polypeptide refers to a biologically active variant, alleles, mutant, and interspecies homolog of an *Escherichia coli* OmpX polypeptide having the amino acid sequence of SEQ ID NO:10. Illustrative OmpX polypeptides from other species include *Enterobacteriaceae* sp. protein sequence accession number WP_001295296.1; *Shigella flexneri* protein sequence accession number WP_025757391.1; *Salmonella* sp. protein sequence accession number WP_000716762.1; *Citrobacter farmeri* protein sequence accession number GAL49278.1; and *Klebsiella* sp. protein sequence accession number WP_002895845.1. An "OmpX porin" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 100 or 150, or more, amino acids, or over the length of the mature OmpX polypeptide of SEQ ID NO:10. An "OmpX porin polynucleotide" as used herein refers to a polynucleotide that encodes an OmpX porin polypeptide.

An "OmpE porin" polypeptide refers to a biologically active variant, alleles, mutant, and interspecies homolog of an *Escherichia coli* OmpE (also referred to as PhoE) polypeptide having the amino acid sequence of SEQ ID NO:12. Illustrative OmpE polypeptides from other species include *Enterobacteriaceae* sp. protein sequence accession number WP_000749863.1; *Shigella* sp. protein sequence accession number WP_000749871.1; *Citrobacter* sp. protein sequence accession number WP_003830831.1; and *Salmonella enterica* protein sequence accession number WP_000749852.1. An "OmpE porin" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 100, 200, 250, 300, or more, amino acids, or over the length of the mature OmpE polypeptide of SEQ ID NO:12. An "OmpE porin polynucleotide" as used herein refers to a polynucleotide that encodes an OmpE porin polypeptide.

An "OmpG porin" polypeptide refers to a biologically active variant, alleles, mutant, and interspecies homolog of an *Escherichia coli* OmpG polypeptide having the amino acid sequence of SEQ ID NO:14. Illustrative OmpG porin polypeptides from other species include *Enterobacteriaceae* sp. protein sequence accession number WP_000735257.1; *Shigella* sp. protein sequence accession number WP_000735251.1; *Citrobacter youngae* protein sequence accession number WP_006684355.1; and *Salmonella enterica* protein sequence accession number WP_023176364.1. An "OmpG porin" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 100, 200, or 250, or more, amino acids, or over the length of the mature OmpG polypeptide of SEQ ID NO:14. An "OmpG porin polynucleotide" as used herein refers to a polynucleotide that encodes an OmpG porin polypeptide.

An "OmpW porin" polypeptide refers to a biologically active variant, alleles, mutant, and interspecies homolog of an *Escherichia coli* OmpW polypeptide having the amino acid sequence of SEQ ID NO:16. Illustrative OmpW porin polypeptides form other species include *Enterobacteriaceae* sp. protein sequence accession number WP_000737226.1; *Shigella flexneri* protein sequence accession number WP_000737239.1; *Citrobacter* sp. protein sequence accession number WP_016153263.1; *Salmonella enterica* protein sequence accession number WP_000714802.1; and *Klebsiella* sp. protein sequence accession number WP_004121296.1. An "OmpW porin" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 100 or 150, or more, amino acids, or over the length of the mature OmpW polypeptide of SEQ ID NO:16. An "OmpW porin polynucleotide" as used herein refers to a polynucleotide that encodes an OmpW porin polypeptide.

The terms "increased expression" and "overexpression" of an OMP polypeptide are used interchangeably herein to refer to an increase in the amount of OMP polypeptide in a genetically modified cell, e.g., a cell into which an expression construction encoding an OMP polypeptide has been introduced, compared to the amount of OMP polypeptide in a counterpart cell that does not have the genetic modification, i.e., a cell of the same strain without the modification. An increased level of expression for purposes of this application is at least 5%, or at least 10%, 20%, 30%, 40%, 50%, 60%, 70%, 80%, 90%, 100%, or greater, compared to the counterpart unmodified cell. The unmodified cell need not express the OMP polypeptide. Thus, the term "overexpression" also includes embodiments in which an OMP polypeptide is expressed in a host cell that does not natively express the OMP polypeptide. Increased expression of an OMP polypeptide can be assessed by any number of assays, including, but not limited to, measuring the level of RNA transcribed from the OMP polypeptide gene, the level of OMP polypeptide, and/or the level of OMP polypeptide activity.

The term "enhanced" in the context of the production of an amino acid, e.g., lysine, or a lysine derivative, e.g., cadaverine, as used herein refers to an increase in the production of lysine or the derivative in comparison to a control counterpart cell that does not have a genetic modification to increase the expression of an OMP polypeptide. Production of the amino acid or its derivative is enhanced by at least 5%, typically at least 0%, 20%, 30%, 40%, 50%, 60%, 70%, 80%, 90%, 100%, or greater compared to the control cell.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a residue in an OmpA polypeptide variant or homolog "corresponds to" an amino acid at a position in SEQ ID NO:4 when the residue aligns with the amino acid in a comparison of SEQ ID NO:4 and the homolog or variant in a maximal alignment.

An "OMP porin polynucleotide" as used herein refers to a nucleic acid that encodes an OMP porin polypeptide.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether a porin polypeptide has sequence identity to SEQ ID NO:4, 6, 8, 12, 14, or 16, or another polypeptide reference sequence, is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). For amino acid sequences, the BLASTP program uses as defaults a word size (W) of 3, an expectation (E) of 10, and the BLOSUM62 scoring matrix (see Henikoff & Henikoff, 1989, Proc. Natl. Acad. Sci. USA 89:10915). Other programs that may be used include the Needleman-Wunsch procedure, J. Mol. Biol. 48: 443-453 (1970), using BLOSUM62, a Gap start penalty of 7 and gap extend penalty of 1; and gapped BLAST 2.0 (see Altschul, et al. 1997, Nucleic Acids Res., 25:3389-3402) both A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, *Proteins* (1984)).

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety). Similarly, a polypeptide is "heterologous" to a host cell if the native wildtype host cell does not produce the polypeptide.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein or enzyme.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of a plasmid or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, refers to a polypeptide molecule that is free of other components of the cell, i.e., it is not associated with in vivo substances.

Introduction

The present invention is based, in part, on the discovery that increased expression of one or more OMP porin polypeptides in a microorganism, such as a gram negative bacteria, enhances amino acid, e.g., lysine, production and/or production of a amino acid derivative such as cadaverine. An OMP porin polypeptide that is overexpressed in accordance with the invention often is a beta-barrel polypeptide having 8, 14, or 16 strands.

A host cell that is engineered to overexpress an OMP porin polypeptide is also typically engineered to overexpress an enzyme to synthesize the amino acid derivative, such as a lysine decarboxylase polypeptide, and/or an additional polypeptide that is involved in amino acid biosynthesis. Lysine decarboxylase and lysine biosynthesis polypeptide and nucleic acid sequences are well known in the art.

Polynucleotides Encoding Porin Polypeptides

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2014).

OMP porin nucleic acid and polypeptide sequences suitable for use in the invention include porin nucleic acid sequences that encode a porin polypeptide as illustrated in any of SEQ NOs:4, 6, 8, 10, 12, 14, or 16, or substantially identical variants thereof. Such a variant typically has at least 70%, or at least 75%, 80%, 85%, or 90% identity to one of SEQ ID NOS:4, 6, 8, 10, 12, 14, or 16, or an alternative OMP porin polypeptide, e.g., a known homolog of SEQ ID NO:4, 6, 8, 10, 12, 14, or 16. As used herein, the term "variant" encompasses biologically active polypeptides having one or more substitutions, deletions, or insertions relative to an OMP porin polypeptide reference sequence, such as SEQ ID NO:4, 6, 8, 10, 12, 14, or 16. Thus, the term "variant" includes biologically active fragments as well as substitution variants.

OMP porin polypeptides are well known in the art and the structure of OMP porins have been extensively characterized. The pore structure of these proteins is formed almost entirely of a beta-barrel. The beta-barrel structures of OMP porins range from 8- to 18-stranded antiparallel beta barrels. The monomeric protein often, although not always, forms a trimeric structure integrated into the outer membrane. Additional common structural features shared by OMP porins include a signal sequence, often 21 amino acids in length, at the N-terminus of the protein, which is cleaved during export; the absence of long hydrophobic stretches; a lack of cysteine residues; and a C-terminal phenylalanine. Illustrative OMP porin polypeptide sequence are provided in SEQ ID NOs:4, 6, 8, 10, 12, 14, and 16. Structural characteristics of OMP porin polypeptides are additionally reviewed in Galdiero et al., Curr. Prot. Peptide Sci. 13:843-854, 2012, which is incorporated by reference.

One of skill can obtain an OMP porin polypeptide variant by using the sequence alignments and structural analyses available in the art to identify residues within conserved structures that would be expected to retain porin polypeptide transport function as well as that would be tolerant to substitution.

OMP porin polypeptide activity can be assessed using any number of assays, including assays that evaluate transport of the amino acid or an amino acid-derived compound. An exemplary assay measures cadaverine production in E. coli that are modified to co-express CadA with the OMP polypeptide. CadA and the OMP polypeptide are introduced into E. coli on the same plasmid with an antibiotic-resistance selectable marker. Antibiotic-resistant colonies are selected and cultured. Cultures are then grown at 37° C. for 2 hours in the presence of 0.1 mL of lysine-HCl and PLP to a final concentration of 40 g/L and 0.1 mM, respectively. Cadaverine production from each sample is quantified using NMR, and yield is calculated by dividing the molar amount of cadaverine produced by the molar amount of lysine added. An OMP porin polypeptide for use in the invention increases the yield of cadaverine. Alternatively, colonies are evaluated for increased lysine production or production of another lysine derivative.

Isolation or generation of OMP porin polynucleotide sequences can be accomplished by a number of techniques. Such techniques will be discussed in the context of OMP porin genes. However, one of skill understands that the same techniques can be used to isolate and express other desired genes. In some embodiments, oligonucleotide probes based on the sequences disclosed here can be used to identify the desired polynucleotide in a cDNA or genomic DNA library from a desired bacteria; species. Probes may be used to hybridize with genomic DNA or cDNA sequences to isolate homologous genes in the same or different plant species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying an OMP porin polynucleotide in bacteria can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Outer membrane porin nucleic acid sequences for use in the invention includes genes and gene products identified and characterized by techniques such as hybridization and/or sequence analysis using exemplary nucleic acid sequences, e.g., SEQ ID NO:3, SEQ ID NO:5, SEQ ID NO:7, SEQ ID NO:9, SEQ ID NO:11, SEQ ID NO:13, or SEQ ID NO:15.

In some embodiments, a host cell is genetically modified by introducing a nucleic acid sequence having at least 60% identity, or at least 70%, 75%, 80%, 85%, or 90% identity, or 100% identity, to a polynucleotide comprising SEQ ID NO:3, SEQ ID NO:5, SEQ ID NO:7, SEQ ID NO:9, SEQ ID NO:11, SEQ ID NO:13, or SEQ ID NO:15.

A polynucleotide encoding an OMP porin polypeptide comprises a region that encodes a signal peptide. The signal peptide may be a heterologous signal peptide, e.g., an OmpA porin polynucleotide may encodes a signal peptide from another OMP porin polypeptide or may encode another bacterial signal peptide.

Nucleic acid sequences encoding a porin polypeptide that confers increased production of an amino acid, e.g., lysine, or an amino acid-derived product, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See, e.g., See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292.)

Preparation of Recombinant Vectors

Recombinant vectors for expression of a porin polypeptide can be prepared using methods well known in the art. For example, a DNA sequence encoding an OMP porin polypeptide (described in further detail below), can be combined with transcriptional and other regulatory sequences which will direct the transcription of the sequence from the gene in the intended cells, e.g., bacterial cells such as *E. coli*. In some embodiments, an expression vector that comprises an expression cassette that comprises the gene encoding the OMP porin polypeptide further comprises a promoter operably linked to the porin gene. In other embodiments, a promoter and/or other regulatory elements that direct transcription of the OMP porin gene are endogenous to the host cell and an expression cassette comprising the porin gene is introduced, e.g., by homologous recombination, such that the exogenous gene is operably linked to an endogenous promoter and is expression driven by the endogenous promoter.

As noted above, expression of the gene encoding porin polypeptide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra.

Additional promoters include promoters described by Jensen & Hammer, *Appl. Environ. Microbiol.* 64:82, 1998; Shimada, et al., *J. Bacteriol.* 186:7112, 2004; and Miksch et al., *Appl. Microbiol. Biotechnol.* 69:312, 2005.

In some embodiments, a promoter that influences expression of a native OMP porin polypeptide may be modified to increase expression. For example, an endogenous OmpA, OmpF, OmpC, OmpE, OmpG, OmpX, or OmpW promoter may be replaced by a promoter that provides for increased expression compared to the native promoter.

An expression vector may also comprise additional sequences that influence expression of a gene encoding the OMP porin polypeptide. Such sequences include enhancer sequences, a ribosome binding site, or other sequences such as transcription termination sequences, and the like.

A vector expressing a nucleic acid encoding an OMP porin polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli*.

Although any suitable expression vector may be used to incorporate the desired sequences, readily available bacterial expression vectors include, without limitation: plasmids such as pSC101, pBR322, pBBR1MCS-3, pUR, pET, pEX, pMR100, pCR4, pBAD24, p15a, pACYC, pUC, e.g., pUC18 or pUC19, or plasmids derived from these plasmids; and bacteriophages, such as M13 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to overexpress an OMP porin polypeptide. Such a host cell may comprise a nucleic acid encoding a heterologous OMP porin polypeptide, including any non-naturally occurring OMP porin polypeptide variant; or may be genetically modified to overexpress a native, or endogenous, OMP porin polypeptide relative to a wildtype host cell.

Genetic modification of a host cell to overexpress an OMP porin polypeptide is often performed in conjunction with modifying the host cell to overexpress a lysine decarboxylase polypeptide and/or one or more amino acid biosynthesis polypeptides.

A lysine decarboxylase refers to an enzyme that converts L-lysine into cadaverine. The enzyme is classified as E.C. 4.1.1.18. Lysine decarboxylase polypeptides are well characterized enzymes, the structures of which are well known in the art (see, e.g., Kanjee, et al., *EMBO J.* 30: 931-944, 2011; and a review by Lemmonier & Lane, *Microbiology* 144; 751-760, 1998; and references described therein). The EC number for lysine decarboxylase is 4.1.1.18. Please see attachment for lysine decarboxylases from other organisms. Illustrative lysine decarboxylase sequences are CadA homologs from *Klebsiella* sp., WP_012968785.1; *Enterobacter aerogenes*, YP 004592843.1; *Salmonella enterica*, WP_020936842.1; *Serratia* sp., WP_033635725.1; and *Raoultella ornithinolytica*, YP 007874766.1; and LdcC homologs from *Shigella* sp., WP_001020968.1; *Citrobacter* sp., WP_016151770.1; and *Salmonella enterica*, WP 001021062.1. As used herein, a lysine decarboxylase, includes variants of native lysine decarboxylase enzymes that have lysine decarboxylase enzymatic activity. Additional lysine decarboxylase enzyme are described in PCT/CN2014/080873 and PCT/CN2015/072978.

In some embodiments, a host cell may be genetically modified to express one or more lysine biosynthesis polypeptides. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms. Such genes are well known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
| --- | --- | --- | --- |
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate:meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |

-continued

| Protein | Gene | EC Number | GenBank Accession No. |
|---|---|---|---|
| putrescine importer (PuuP) | puuP | NA | AAC74378.2 |
| putrescine/cadaverine aminotransferase (YgjG) | ygjG | 2.6.1.82 | AAC76108.3 |

Nucleic acids encoding a lysine decarboxylase or an amino acid biosynthesis polypeptide may be introduced into the host cell along with the OMP porin polynucleotide, e.g., encoded on a single expression vector, or introduced in multiple expression vectors at the same time. Alternatively, the host cell may be genetically modified to overexpress lysine decarboxylase or one or more amino acid biosynthesis polypeptides before or after the host cells genetically modified to overexpress the porin polypeptide.

In alternative embodiments, a host cell that overexpresses a naturally occurring OMP porin polypeptide can be obtained by other techniques, e.g., by mutagenizing cells, e.g., E coli cells, and screening cells to identify those that express an OMP porin polypeptide, e.g., OmpA, OmpC, OmpF, OmpG, OmpE, OmpW, or OmpX, at a higher level compared to the cell prior to mutagenesis.

A host cell comprising an OMP porin polypeptide as described herein is a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella, or Klebsiella taxonomical classes. In some embodiments, the host cells are members of the genus Escherichia, Hafnia, or Corynebacterium. In some embodiments, the host cell is an Escherichia coli, Hafnia alvei, or Corynebacterium glutamicum host cell.

In some embodiments, the host cell is a gram-positive bacterial host cell, such as a Bacillus sp., e.g., Bacillus subtilis or Bacillus licheniformis; or another Bacillus sp. such as B. alcalophilus, B. aminovorans, B. amyloliquefaciens, B. caldolyticus, B. circulans, B. stearothermophilus, B. thermoglucosidasius, B. thuringiensis or B. vulgatis.

Host cells modified in accordance with the invention can be screened for increased production of an amino acid, such as lysine, or an amino acid derivative, such as cadaverine, as described herein.

Methods of Producing an Amino Acid or an Amino Acid Derivative.

A host cell genetically modified to overexpress an OMP porin polypeptide can be employed to produce amino acids or its derivative. In some embodiments, the host cell produces lysine. In some embodiments, the host cell produces cadaverine. To produce an amino acid or the amino acid derivative, a host cell genetically modified to overexpress an OMP porin polypeptide as described herein can be cultured under conditions suitable to allow expression of the polypeptide and expression of genes that encode the enzymes that are used to produce the amino acid or the amino acid derivative. A host cell modified in accordance with the invention provides a higher yield of amino acid or the amino acid derivatives relative to a non-modified counterpart host cell that expresses the OMP porin polypeptide at native levels.

Host cells may be cultured using well known techniques (e.g., the illustrative conditions provided in the examples section).

The amino acid or amino acid derivative can then be separated and purified using known techniques. Lysine or lysine derivatives, e.g., cadaverine, produced in accordance with the invention may then be used in any known process, e.g., to produce a polyamide.

In some embodiments, lysine may be converted to aminovalerate using enzymes or caprolactam by using enzymes and chemical catalysts.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Example 1: Construction of Plasmid Vectors that Encode CadA

A plasmid vector containing wild-type E. coli_cadA_ (SEQ ID NO: 1), which encodes the lysine decarboxylase CadA (SEQ ID NO: 2), was amplified from the E. coli MG1655 K12 genomic DNA using the PCR primers cadA-F and cadA-R, digested using the restriction enzymes SacI and XbaI, and ligated into pUC18 to generate the plasmid pCIB60.

Example 2: Construction of Plasmid Vectors Expressing Outer Membrane Proteins

The E. coli gene, ompA (SEQ ID NO: 3), that encodes the membrane porin protein, OmpA (SEQ ID NO: 4), was amplified from the E. coli MG1655 K12 genomic DNA using the PCR primers ompA-F and ompA-R, digested with the restriction enzymes SacI and XbaI, and ligated into a pUC18 plasmid vector to create pCIB88. Similarly, ompC (SEQ ID NO: 5), that encodes the membrane porin protein, OmpC (SEQ ID NO: 6), was cloned into a pUC18 plasmid vector using the primers ompC-F and ompC-R to create the plasmid pCIB89. Similarly, ompF (SEQ ID NO: 7), that encodes the membrane porin protein, OmpF (SEQ ID NO: 8), was cloned into a pUC18 plasmid vector using the primers ompF-F and ompF-R to create the plasmid pCIB87. Similarly, ompX(SEQ ID NO: 9), that encodes the membrane porin protein, OmpX (SEQ ID NO: 10), was cloned into a pUC18 plasmid vector using the primers ompX-F and ompX-R to create the plasmid pCIB86. Similarly, ompE (SEQ ID NO: 11), that encodes the membrane porin protein, OmpE (SEQ ID NO: 12), was cloned into a pUC18 plasmid vector using the primers ompE-F and ompE-R to create the plasmid pCIB91. Similarly, ompG (SEQ ID NO: 13), that encodes the membrane porin protein, OmpG (SEQ ID NO: 14), was cloned into a pUC18 plasmid vector using the primers ompG-F and ompG-R to create the plasmid pCIB80.

Similarly, ompW (SEQ ID NO: 15), that encodes the membrane porin protein, OmpW (SEQ ID NO: 16), was cloned into a pUC18 plasmid vector using the primers ompW-F and ompW-R to create the plasmid pCIB81.

Example 3: Construction of Plasmid Vectors that Encode a Tetracycline Efflux Pump The synthetic promoter sequence (SEQ ID NO: 17) was synthesized using the PCR primers psyn-1 and psyn-2. Primer psyn-1 contains the promoter sequence and a sequence homologous to pUC18, and primer psyn-2 contains a sequence homologous to pUC18. These two PCR primers were used to amplify a portion of pUC18 that includes the multi-cloning site from the plasmid inserted downstream of the synthetic promoter sequence. Restriction enzymes EcoRI and ScaI were used to digest the amplified DNA containing the synthetic promoter, which was further ligated into pUC18 to construct pCIB10.

The tetA gene (SEQ ID NO: 18), that encodes a tetracycline efflux pump, TetA (SEQ ID NO: 19), was amplified from the *E. coli* cloning vector pBR322 using the PCR primers tetA-F and tetA-R. The amplified DNA was digested with the restriction enzymes SacI and XbaI, and ligated into pCIB10 plasmid vector to create pCIB20.

Example 4: Construction of Plasmid Vectors Co-Expressing Synthetic Operon I that Contains Three Proteins (LysC, DapA, LysA) from the Lysine Biosynthetic Pathway Three genes from *E. coli*, lysC, dapA, and lysA, encode proteins involved in the *E. coli* lysine biosynthetic pathway: aspartate kinase (LysC or AKIII, encoded by lysC), dihydrodipicolinate synthase (DapA or DHDPS, encoded by dapA), and diaminopimelate decarboxylase (LysA, encoded by lysA). The three genes were cloned into a plasmid vector and the three proteins, LysC (SEQ ID NO: 21), DapA (SEQ ID NO: 23), and LysA (SEQ ID NO: 25) were overexpressed in *E. coli*. The gene lysC was amplified from the *E. coli* MG1655 K12 genomic DNA using the primers lysC-F and lysC-R, and the amplified fragment was digested using SacI and BamHI, and ligated into pUC18 to create pCIB7. The gene dapA was amplified from the *E. coli* MG1655 K12 genomic DNA using the primers dapA-F and dapA-R, and the amplified fragment was digested using BamHI and XbaI, and ligated into pCIB7 to create pCIB8. The gene lysA was amplified from the *E. coli* MG1655 K12 genomic DNA using the primers lysA-F and lysA-R, and the amplified fragment was digested using XbaI and SalI, and ligated into pCIB8 to create pCIB9. The three-gene operon was amplified from pCIB9 using the primers lysC-F and lysA-R. The amplified product was digested using SacI and SalI, and the digested fragment was ligated into pCIB10 to create pCIB32. The gene tetA was amplified from pCIB20 using the primers tetA-F3 and tetA-R3, and the amplified fragment was digested using SbfI and XhoI, and ligated into pCIB32 to generate plasmid pCIB42.

Example 5: Construction of Plasmid Vectors Co-Expressing Various Aspartokinases. Various Aspartokinases were Expressed in Order to Increase Lysine Production Two pairs of mutations were chosen that enabled the *E. coli* aspartokinase III (LysC or AKIII, encoded by lysC, SEQ ID NO: 20) to have an increased feedback resistance to lysine. The gene encoding the first mutant, LysC-1 (M318I, G323D) (SEQ. ID NO: 27) was constructed using the primers 318-F, 318-R, 323-F, 323-R. The genes encoding LysC-1 (M318I, G323D) was cloned into pCIB32 and replaced the wild-type *E. coli* aspartokinase, LysC, to create the plasmids pCIB43. The aspartokinase from *Streptomyces* strains that is capable of producing polylysine was previously suggested, but not proven, to be more feedback resistant to lysine compared to *E. coli* aspartokinase. As such, the aspartokinase gene from *Streptomyces lividans* was codon optimized, synthesized, and cloned in place of wild-type lysC in pCIB32 in order to create the plasmid pCIB55 using the primers SlysC-F and SlysC-R. The resulting aspartokinase protein that was expressed was named S-LysC (SEQ ID NO: 29).

Example 6: Construction of Plasmid Vectors Co-Expressing Synthetic Operon II that Contains Three Proteins (Asd, DapB, DapD, AspC) from the Lysine Biosynthetic Pathway Next, the expression of four additional genes, asd, dapB, dapD, and aspC, which are involved in the lysine biosynthetic pathway of *E. coli*, was enhanced. These genes encode the following enzymes: aspartate semialdehyde dehydrogenase (Asd (SEQ ID NO: 31), encoded by asd), dihydrodipicolinate reductase (DapB or DHDPR (SEQ ID NO: 33), encoded by dapB), tetrahydrodipicolinate succinylase (DapD (SEQ ID NO: 35), encoded by dapD), and aspartate transaminase (AspC (SEQ ID NO: 37), encoded by aspC). The gene asd was amplified from the *E. coli* MG1655 K12 genomic DNA using the primers asd-F and asd-R, and the amplified fragment was digested using SacI and BamHI, and ligated into pUC18 to create pCIB12. The gene dapB was amplified from the *E. coli* MG1655 K12 genomic DNA using the primers dapB-F and dapB-R, and the amplified fragment was digested using BamHI and XbaI, and ligated into pCIB12 to create pCIB13. The gene dapD was amplified from the *E. coli* MG1655 K12 genomic DNA using the primers dapD-F and dapD-R, and the amplified fragment was digested using XbaI and SalI, and ligated into pCIB13 to create pCIB14. Similarly, the gene aspC was amplified from the *E. coli* MG1655 K12 genomic DNA using the primers aspC-F and aspC-R, and the amplified fragment was digested using XbaI and SalI, and ligated into pCIB13 to create pCIB31. The gene tetA was amplified from pCIB20 using the primers tetA-F3 and tetA-R3, and the amplified fragment was digested using XhoI and SphI and ligated into pCIB14 and pCIB31 to generate plasmids pCIB15 and pCIB59, respectively.

Example 7: Construction of Plasmid Vectors Co-Expressing Synthetic Operons I and II that Contain Proteins from the Lysine Biosynthetic Pathway The two synthetic operons, Synthetic Operon I and Synthetic Operon II, consisting of the genes lysC, dapA, lysA, asd, dapB, and aspC were combined into a single vector. The operon from pCIB32 consisting of the genes lysC, dapA, and lysA was amplified using the primers LAL-F and LAL-R. The operon from pCIB59 consisting of the genes asd, dapB, and aspC and the tetA gene was amplified using the primers ABC-F and ABCT-R. The products were digested using the restriction enzymes ApaI and KpnI. The digested products of pCIB32 and pCIB59 were ligated to form pCIB103-1. Similarly, the variants of Synthetic Operon I that contain different aspartokinases were combined with Synthetic Operon II. The variant of Synthetic Operon I that contains LysC-1 was amplified from pCIB43 using the primers LAL-F and LAL-R, digested, and ligated with the digested product of pCIB59 to form pCIB103-2. The variant of Synthetic Operon I that contains S-LysC was amplified from pCIB55 using the primers SAL-F and SAL-R, digested, and ligated with the digested product of pCIB59 to form pCIB103-3.

Example 8: Production of Lysine from E. coli Over-Expressing Lysine Synthetic Operons I and II E. coli MG1655 K12 was transformed with one of the following plasmids: pCIB20, pCIB103-1, pCIB103-2, or pCIB103-3, in order to make the respective strains: CIB20, CIB103-1, CIB103-2, or CIB103-3. Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, and tetracycline (10 µg/mL). The following day, each culture was inoculated into 100 mL of fresh medium with 30 g/L of glucose, 0.7% $Ca(HCO_3)_2$, and tetracycline (10 µg/mL) and grown for 72 hours at 37° C., at which point the concentration of lysine in each culture was determined (Table 1).

TABLE 1

Production of lysine by E. coli strains containing Synthetic Operons I and II.

| Strain | Protein(s) | Lysine (g/L) |
|---|---|---|
| CIB20 | TetA | n.d. |
| CIB103-1 | LysC, DapA, LysA, Asd, DapB, AspC, TetA | 1.0 ± 0.4 |
| CIB103-2 | LysC-1, DapA, LysA, Asd, DapB, AspC, TetA | 6.6 ± 0.2 |
| CIB103-3 | S-LysC, DapA, LysA, Asd, DapB, AspC, TetA | 6.0 ± 0.5 | n.d.: none detected

As shown in Table 1, the over production of different variants of aspartokinase (LysC-1, LysC-2, S-LysC) increased lysine production compared to the expression of wild-type E. coli aspartokinase (LysC)—compare 1.0 g/L for CIB103-1 to 6.6 g/L for CIB103-2, 6.0 g/L for CIB103-3.

Example 9: Production of Lysine from E. coli Co-Overexpressing Genes that Encode Outer Membrane Proteins and Lysine Synthetic Operons I and II CIB103-3 was transformed with one of the plasmids overexpressing one of the outer membrane proteins: pCIB80, pCIB81, pCIB86, pCIB87, pCIB88, pCIB89, or pCIB91, in order to create the respective strains: CIB80, CIB81, CIB86, CIB87, CIB88, CIB89, or CIB91.

Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and tetracycline (10 µg/mL). The following day, each culture was inoculated into 100 mL of fresh medium with 30 g/L of glucose, 0.7% $Ca(HCO_3)2$, ampicillin (100 µg/mL) and tetracycline (10 µg/mL), and grown for 72 hours at 37° C., at which point the concentration of lysine in each culture was determined (Table 2).

TABLE 2

Production of lysine by E. coli strains that contain the lysine Synthetic Operons I and II and overproduce outer membrane proteins.

| Strain | Protein(s) | Lysine (g/L) |
|---|---|---|
| CIB103-3 | S-LysC, DapA, LysA, Asd, DapB, AspC, TetA | 6.0 ± 0.1 |
| CIB80 | S-LysC, DapA, LysA, Asd, DapB, AspC, TetA, OmpG | 6.3 ± 0.2 |
| CIB81 | S-LysC, DapA, LysA, Asd, DapB, AspC, TetA, OmpW | 7.1 ± 0.2 |
| CIB86 | S-LysC, DapA, LysA, Asd, DapB, AspC, TetA, OmpX | 6.7 ± 0.3 |
| CIB87 | S-LysC, DapA, LysA, Asd, DapB, AspC, TetA, OmpF | 7.0 ± 0.1 |
| CIB88 | S-LysC, DapA, LysA, Asd, DapB, AspC, TetA, OmpA | 7.6 ± 0.2 |
| CIB89 | S-LysC, DapA, LysA, Asd, DapB, AspC, TetA, OmpC | 7.3 ± 0.1 |
| CIB91 | S-LysC, DapA, LysA, Asd, DapB, AspC, TetA, OmpE | 6.0 ± 0.3 |

As shown in Table 2, overexpression of certain genes that encode outer membrane proteins increase lysine production. The overproduction of either OmpG or OmpE did not significantly increase lysine production—compare 6.2 g/L for CM 103-3 with 6.0 g/L for CIB80 and 5.9 g/L for CIB91. The overproduction of OmpW, OmpX, OmpF, OmpA, and OmpC increased lysine production, with the overproduction of OmpA leading to the greatest increase—7.0 g/L for CIB88 compared to 6.2 g/L for CM 103-3.

Example 10: Construction of Plasmid Vectors Co-Expressing Outer Membrane Proteins and CadA The E. coli outer membrane genes, ompA, ompC, ompE, ompF, ompG, ompW, and ompX, were amplified as described in Example 2 using the appropriate primers (ompA-F2, ompA-R2, ompC-F2, ompC-R2, ompE-F2, ompE-R2, ompF-F2, ompF-R2, ompG-F2, ompG-R2, ompW-F2, ompW-R2, ompX-F2, ompX-R2), digested using XbaI and HindIII, and ligated into pCIB60 in order to co-express the outer membrane genes with the lysine decarboxylase gene cadA. The plasmid co-expressing cadA and ompA is pCIB120, cadA and ompC is pCIB132, cadA and ompE is pCIB169, cadA and ompF is pCIB133, cadA and ompG is pCIB179, cadA and ompW is pCIB180, cadA and ompX is pCIB172.

Example 11: Construction of Plasmid Vectors Co-Expressing YbjE and CadA ybjE is a gene from E. coli that was previously shown to increase lysine production by potentially acting as a transporter (WO/2005/073390). We tested whether overexpression of ybjE could also increase cadaverine production.

The E. coli gene, ybjE (SEQ ID NO: 38), that encodes the membrane porin protein, YbjE (SEQ ID NO: 39), was amplified from the E. coli MG1655 K12 genomic DNA using the PCR primers ybjE-F and ybjE-R. The amplified DNA was digested with the restriction enzymes XbaI and HindIII, and ligated into a pCIB60 plasmid vector to create pCIB106.

Example 12: Production of Cadaverine from E. coli Co-Expressing Outer Membrane Proteins and CadA E. coli MG1655 K12 was transformed with pCIB60, pCIB106, pCIB120, pCIB132, pCIB169, pCIB133, pCIB179, pCIB180, or pCIB172. Three colonies of each transformation were grown overnight in LB medium with ampicillin (100 µg/mL) in a 3 mL culture at 37° C. The following day, 0.9 mL of each overnight culture was added to 0.1 mL of lysine-HCl and PLP to a final concentration of 40 g/L and 0.1 mM, respectively. Each mixture was incubated at 37° C. for 2 hours. Cadaverine production from each sample was quantified using NMR, and yield was calculated by dividing the molar amount of cadaverine produced by the molar amount of lysine added. The yield from each sample is presented in Table 3.

TABLE 3

Production of cadaverine by *E. coli* strains co-producing outer membrane proteins and CadA.

| Plasmid | Protein(s) | Cadaverine Yield (%) |
| --- | --- | --- |
| pCIB60 | CadA | 37.5 ± 5.2 |
| pCIB106 | CadA, YbjE | 35.2 ± 3.5 |
| pCIB120 | CadA, OmpA | 81.0 ± 4.7 |
| pCIB132 | CadA, OmpC | 79.0 ± 4.4 |
| pCIB169 | CadA, OmpE | 60.3 ± 3.9 |
| pCIB133 | CadA, OmpF | 70.2 ± 5.0 |
| pCIB179 | CadA, OmpG | 64.3 ± 3.1 |
| pCIB180 | CadA, OmpW | 80.4 ± 5.3 |
| pCIB172 | CadA, OmpX | 67.4 ± 6.2 |

As shown in Table 3, overproduction of the outer membrane proteins OmpA, OmpC, OmpE, OmpF, OmpG, OmpW, and OmpX in addition to CadA increased cadaverine production compared to the control that only overproduced CadA in *E. coli*. Surprisingly, overexpression of ybjE (pCIB106) did not increase cadaverine production, which suggests that its activity is specific to increasing lysine production.

Example 13: Production of Cadaverine from *H. alvei* Co-Expressing Outer Membrane Proteins and CadA

*H. alvei* was transformed with pCIB60, pCIB120, pCIB132, pCIB169, pCIB133, pCIB179, pCIB180, or pCIB172. Three colonies of each transformation were grown overnight in LB medium with ampicillin (100 µg/mL) in a 3 mL culture at 37° C. The following day, 0.9 mL of each overnight culture was added to 0.1 mL of lysine-HCl and PLP to a final concentration of 40 g/L and 0.1 mM, respectively. Each mixture was incubated at 37° C. for 2 hours. Cadaverine production from each sample was quantified using NMR, and yield was calculated by dividing the molar amount of cadaverine produced by the molar amount of lysine added. The yield from each sample is presented in Table 4.

TABLE 4

Production of cadaverine by *H. alvei* strains co-producing outer membrane proteins and CadA.

| Plasmid | Protein(s) | Cadaverine Yield (%) |
| --- | --- | --- |
| pCIB60 | CadA | 46.7 ± 8.3 |
| pCIB120 | CadA, OmpA | 70.1 ± 3.4 |
| pCIB132 | CadA, OmpC | 79.6 ± 5.4 |
| pCIB169 | CadA, OmpE | 45.5 ± 4.9 |
| pCIB133 | CadA, OmpF | 59.1 ± 5.1 |
| pCIB179 | CadA, OmpG | 50.5 ± 3.7 |
| pCIB180 | CadA, OmpW | 62.5 ± 2.9 |
| pCIB172 | CadA, OmpX | 45.2 ± 7.3 |

As shown in Table 4, overproduction of the outer membrane proteins OmpA, OmpC, OmpF, and OmpW in addition to CadA increased cadaverine production compared to the control that only overproduced CadA in *H. alvei*. Surprisingly, this is different from the result observed in *E. coli*, where OmpA, OmpC, OmpE, OmpF, OmpG, OmpW, and OmpX all increased cadaverine production.

Example 14: Cadaverine Inhibits Gram-Negative Bacteria

It was previously shown byQian et al., *Biotechnology and Bioengineering* 108:93-103, 2010 that cadaverine inhibits growth of the gram-negative bacteria *E. coli*. We studied the affect of cadaverine on the gram-negative bacteria *H. alvei*. First, *H. alvei* was transformed with pCIB60 and grown for 24 hours in 50 mL LB medium with ampicillin (100 µg/mL) at 37° C. The following day, 50 mL of the seed culture was added to a 10 L jar fermenter containing 7 mL of fermentation medium (20 g/L glucose, 30 g/L corn steep liquor, 10 g/L yeast extract, 5 g/L ammonium sulfate, 10 g/L MgSO$_4$, 0.05 g/L FeSO$_4$, 0.05 g/L MnSO$_4$, 5 g/L CaCl$_2$, 0.1 g/L ampicillin), and the fermentation proceeded for 18 hours. 10 g of fermentation broth was collected, centrifuged at 6000 rpm for 5 min at room temperature, and the biomass was recovered. 0.5 g of biomass was added to a 50 mM potassium phosphate buffer with either 0% or 3% cadaverine for 24 hours. After incubation, each sample was centrifuged at 6000 rpm for 5 min at room temperature, the biomass was recovered, and fresh potassium phosphate buffer with lysine-HCl and PLP to a final concentration of 200 g/L and 0.1 mM, respectively, was added. The initial pH of the reaction as adjusted to 5.0, and the reaction was allowed to proceed for 120 minutes at 37° C. 1.3 mL of each sample was taken, boiled for 5 minutes, and centrifuged at 10,000 rpm for 1 minute. The cadaverine concentration in each sample was quantified using NMR, and yield was calculated by dividing the molar amount of cadaverine produced by the molar amount of lysine added. The affect of incubating the cells in cadaverine is shown in Table 5.

TABLE 5

Cadaverine inhibits gram-negative bacteria.

| Plasmid | Cadaverine Yield (%) | |
| --- | --- | --- |
| | 0% cadaverine | 3% cadaverine |
| pCIB60 | 35 ± 4.9 | 22 ± 2.1 |

As shown in Table 5, the incubation of *H. alvei* cells in a solution containing cadaverine prior to using the cells to convert lysine to cadaverine negatively affects the cell's ability to act as a catalyst, and a significant decrease in conversion ability is observed. This data supports previous observations that cadaverine negatively affects gram-negative bacteria, including *H. alvei*.

Example 15: Kinetics of Cadaverine Production by *H. alvei* Co-Expressing Outer Membrane Proteins and CadA

*H. alvei* was transformed with pCIB60, pCIB120, pCIB132, pCIB169, pCIB133, pCIB179, pCIB180, or pCIB172. For each transformation, one colony was grown for 24 hours in 50 mL LB medium with ampicillin (100 µg/mL) at 37° C. The following day, 50 mL of the seed culture was added to a 10 L jar fermenter containing 7 mL of fermentation medium (20 g/L glucose, 30 g/L corn steep liquor, 10 g/L yeast extract, 5 g/L ammonium sulfate, 10 g/L $MgSO_4$, 0.05 g/L $FeSO_4$, 0.05 g/L $MnSO_4$, 5 g/L $CaCl_2$, 0.1 g/L ampicillin), and the fermentation proceeded for 18 hours. 10 g of fermentation broth was collected, centrifuged at 6000 rpm for 5 min at room temperature, and the biomass was recovered. 0.5 g of biomass was added to a 50 mM potassium phosphate buffer with 0.1 mL of lysine-HCl and PLP to a final concentration of 200 g/L and 0.1 mM, respectively. The initial pH of the reaction as adjusted to 5.0, and the reaction was allowed to proceed for 240 minutes at 37° C. 1.3 mL samples were taken every 10 to 20 minutes, boiled for 5 minutes, and centrifuged at 10,000 rpm for 1 minute. The cadaverine concentration in each sample was quantified using NMR, and yield was calculated by dividing the molar amount of cadaverine produced by the molar amount of lysine added. By plotting the cadaverine yield over time, the velocity of each reaction was determined (Table 6). Each reaction slowed down significantly by 240 min (<0.1%/min), and the maximum yield at 240 min is shown in Table 6.

TABLE 6

Kinetics of cadaverine production by *H. alvei* strains co-expressing outer membrane proteins and CadA.

| Plasmid | Protein(s) | Velocity (%/min) | Maximum Yield (%) |
|---|---|---|---|
| pCIB60 | CadA | 0.31 | 35 |
| pCIB120 | CadA, OmpA | 0.64 | 45 |
| pCIB132 | CadA, OmpC | 0.67 | 48 |
| pCIB169 | CadA, OmpE | 0.30 | 32 |
| pCIB133 | CadA, OmpF | 0.54 | 46 |
| pCIB179 | CadA, OmpG | 0.48 | 38 |
| pCIB180 | CadA, OmpW | 0.59 | 42 |
| pCIB172 | CadA, OmpX | 0.44 | 39 |

As shown in Table 6, the overproduction of outermembrane proteins OmpA, OmpC, OmpF, OmpG, OmpW, and OmpX with CadA increased the velocity of the catalytic reaction. The concentration of CadA protein did not change across the different strains (verified by SDS-PAGE), so the increase in velocity is due to the increased permeability of the membrane to lysine and/or cadaverine that resulted from the overexpression of the outermembrane proteins. Table 6 also shows that the overproduction of outermembrane proteins OmpA, OmpC, OmpF, OmpW, and OmpX increased the maximum yield, indicating that the overproduction of these proteins increased tolerance to cadaverine.

Example 16: Production of Cadaverine from *E. coli* Co-Overexpressing Genes that Encode a Lysine Decarboxylase and the Lysine Synthetic Operons I and II CIB103-1, CIB103-2, and CIB103-3 were transformed with pCIB60 in order to construct the strains CIB60-1, CIB60-2, and CIB60-3. CIB60-1, CIB60-2, and CIB60-3 all express the genes that encode the lysine decarboxylase gene cadA, and six lysine biosynthesis genes. However, CIB60-1 expresses the wild-type *E. coli* aspartokinase lysC, CIB60-2 expresses a mutant feedback-resistant aspartokinase lysC-1, and CIB60-3 expresses the wild-type *S. lividans* aspartokinase S-lysC.

Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 μg/mL), and ampicillin (100 m/mL). The following day, each culture was inoculated into 100 mL of fresh medium with 30 g/L of glucose, 0.7% $Ca(HCO_3)_2$, tetracycline (10 m/mL) and ampicillin (100 m/mL), and grown for 72 hours at 37° C., at which point the concentration of lysine in each culture was determined (Table 7).

TABLE 7

Production of lysine and cadaverine by *E. coli* strains containing Synthetic Operons I and II and co-producing CadA.

| Strain | Protein(s) | Lysine (g/L) | Cadaverine (g/L) | Total (g/L) |
|---|---|---|---|---|
| CIB103-1 | LysC, DapA, LysA, Asd, DapB, AspC, TetA | 1.9 ± 0.5 | n.d. | 1.9 |
| CIB103-2 | LysC-1, DapA, LysA, Asd, DapB, AspC, TetA | 6.2 ± 0.4 | n.d. | 6.2 |
| CIB103-3 | S-LysC, DapA, LysA, Asd, DapB, AspC, TetA | 5.7 ± 0.3 | n.d. | 5.7 |
| CIB60-1 | LysC, DapA, LysA, Asd, DapB, AspC, TetA, CadA | 1.3 ± 0.2 | 2.5 ± 0.7 | 3.8 |
| CIB60-2 | LysC-1, DapA, LysA, Asd, DapB, AspC, TetA, CadA | 2.9 ± 0.4 | 3.7 ± 0.2 | 6.3 |
| CIB60-3 | S-LysC, DapA, LysA, Asd, DapB, AspC, TetA, CadA | 2.6 ± 0.2 | 3.8 ± 0.6 | 6.4 |

As shown in Table 7, the overproduction of CadA with the lysine Synthetic Operons I and II leads to the production of both lysine and cadaverine. Furthermore, the total production of lysine and cadaverine from glucose increased with the overproduction of CadA. This is most evident when comparing 1.9 g/L for CM 103-1 and 3.8 g/L for CIB60-1. The observation suggests that conversion of lysine to cadaverine is also an effective tool to remove feedback inhibition associated with high lysine concentrations.

Example 17: Production of Cadaverine from *E. coli* Co-Overexpressing Genes that Encode a Lysine Decarboxylase, Outer Membrane Proteins, and the Lysine Synthetic Operons I and II CIB103-3 was transformed with pCIB60, pCIB120, pCIB132, pCIB169, pCIB133, pCIB179, pCIB180, or pCIB172 to make the respective strains CIB60-3, CIB120-3, CIB132-3, CIB169-3, CIB133-3, CIB179-3, CIB180-3, and pCIB172-3.

Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 μg/mL), and ampicillin (100 m/mL). The following day, each culture was inoculated into 100 mL of fresh medium with 30 g/L of glucose, 0.7% $Ca(HCO_3)_2$, tetracycline (10 μg/mL) and ampicillin (100 m/mL), and grown for 72 hours at 37° C., at which point the concentration of lysine in each culture was determined (Table 8).

TABLE 8

Production of lysine and cadaverine by *E. coli* strains containing Synthetic Operons I and II and co-producing CadA and outer membrane proteins.

| Strain | Protein(s) | Lysine (g/L) | Cadaverine (g/L) | Total (g/L) |
|---|---|---|---|---|
| CIB103-3 | S-LysC, DapA, LysA, Asd, DapB, AspC, TetA | 6.0 ± 0.2 | n.d. | 6.0 |
| CIB60-3 | S-LysC, DapA, LysA, Asd, DapB, AspC, TetA, CadA | 2.8 ± 0.2 | 3.6 ± 0.3 | 6.4 |
| CIB120-3 | S-LysC, DapA, LysA, Asd, DapB, AspC, TetA, CadA, OmpA | 2.8 ± 0.2 | 4.8 ± 0.2 | 7.6 |
| CIB132-3 | S-LysC, DapA, LysA, Asd, DapB, AspC, TetA, CadA, OmpC | 3.0 ± 0.3 | 4.9 ± 0.3 | 7.9 |
| CIB169-3 | S-LysC, DapA, LysA, Asd, DapB, AspC, TetA, CadA, OmpE | 2.5 ± 0.2 | 3.3 ± 0.2 | 5.8 |
| CIB133-3 | S-LysC, DapA, LysA, Asd, DapB, AspC, TetA, CadA, OmpF | 3.2 ± 0.3 | 4.5 ± 0.3 | 7.7 |
| CIB179-3 | S-LysC, DapA, LysA, Asd, DapB, AspC, TetA, CadA, OmpG | 2.3 ± 0.2 | 3.5 ± 0.2 | 5.8 |
| CIB180-3 | S-LysC, DapA, LysA, Asd, DapB, AspC, TetA, CadA, OmpW | 3.0 ± 0.1 | 4.3 ± 0.2 | 7.3 |
| CIB172-3 | S-LysC, DapA, LysA, Asd, DapB, AspC, TetA, CadA, OmpX | 2.9 ± 0.2 | 4.4 ± 0.2 | 7.3 |

As shown in Table 8, overproduction of the outer membrane proteins OmpA, OmpC, OmpF, OmpW, and OmpX in addition to CadA increased total lysine and cadaverine production compared to the control that only overproduced CadA in *E. coli* co-expressing the lysine Synthetic Operons I and II. Overproduction of OmpF and OmpW led to the highest increase in total lysine and cadaverine production—compare 7.2 g/L for CIB132-3 and 7.4 g/L for CIB180-3 to 6.4 g/L for CIB60-3. In most cases, both lysine and cadaverine production increased with the overproduction of the outer membrane protein.

| Table of plasmids used in Examples | | | |
|---|---|---|---|
| Host | Protein(s) Overexpressed | Plasmid | Strain |
| | CadA | pCIB60 | |
| | OmpA | pCIB88 | |
| | OmpC | pCIB89 | |
| | OmpE | pCIB91 | |
| | OmpF | pCIB87 | |
| | OmpG | pCIB80 | |
| | OmpW | pCIB81 | |
| | OmpX | pCIB86 | |
| | TetA | pCIB20 | |
| | LysC | pCIB7 | |
| | LysC, DapA | pCIB8 | |
| | LysC, DapA, LysA | pCIB9 | |
| | LysC, DapA, LysA | pCIB32 | |
| | LysC, DapA, LysA, TetA | pCIB42 | |
| | LysC-1, DapA, LysA | pCIB43 | |
| | S-LysC, DapA, LysA | pCIB55 | |
| | Asd | pCIB12 | |
| | Asd, DapB | pCIB13 | |
| | Asd, DapB, DapD | pCIB14 | |
| | Asd, DapB, AspC | pCIB31 | |
| | Asd, DapB, DapD, TetA | pCIB15 | |
| | Asd, DapB, AspC, TetA | pCIB59 | |
| | LysC, DapA, LysA, Asd, DapB, AspC, TetA | pCIB103-1 | |
| | LysC-1, DapA, LysA, Asd, DapB, AspC, TetA | pCIB103-2 | |
| | S-LysC, DapA, LysA, Asd, DapB, AspC, TetA | pCIB103-3 | |
| *E. coli* | TetA | | CIB20 |
| *E. coli* | LysC, DapA, LysA, Asd, DapB, AspC, TetA | | CIB103-1 |
| *E. coli* | LysC-1, DapA, LysA, Asd, DapB, AspC, TetA | | CIB103-2 |
| *E. coli* | S-LysC, DapA, LysA, Asd, DapB, AspC, TetA | | CIB103-3 |
| *E. coli* | S-LysC, DapA, LysA, Asd, DapB, AspC, TetA, OmpA | | CIB88 |
| *E. coli* | S-LysC, DapA, LysA, Asd, DapB, AspC, TetA, OmpC | | CIB89 |
| *E. coli* | S-LysC, DapA, LysA, Asd, DapB, AspC, TetA, OmpE | | CIB91 |
| *E. coli* | S-LysC, DapA, LysA, Asd, DapB, AspC, TetA, OmpF | | CIB87 |
| *E. coli* | S-LysC, DapA, LysA, Asd, DapB, AspC, TetA, OmpG | | CIB80 |

Table of plasmids used in Examples

| Host | Protein(s) Overexpressed | Plasmid | Strain |
|---|---|---|---|
| E. coli | S-LysC, DapA, LysA, Asd, DapB, AspC, TetA, OmpW | | CIB81 |
| E. coli | S-LysC, DapA, LysA, Asd, DapB, AspC, TetA, OmpX | | CIB86 |
| | CadA, OmpA | pCIB120 | |
| | CadA, OmpC | pCIB132 | |
| | CadA, OmpE | pCIB169 | |
| | CadA, OmpF | pCIB133 | |
| | CadA, OmpG | pCIB179 | |
| | CadA, OmpW | pCIB180 | |
| | CadA, OmpX | pCIB172 | |
| | CadA, YbjE | pCIB106 | |
| E. coli | LysC, DapA, LysA, Asd, DapB, AspC, TetA, CadA | | CIB60-1 |
| E. coli | LysC-1, DapA, LysA, Asd, DapB, AspC, TetA, CadA | | CIB60-2 |
| E. coli | S-LysC, DapA, LysA, Asd, DapB, AspC, TetA, CadA | | CIB60-3 |
| E. coli | S-LysC, DapA, LysA, Asd, DapB, AspC, TetA, CadA, OmpA | | CIB120-3 |
| E. coli | S-LysC, DapA, LysA, Asd, DapB, AspC, TetA, CadA, OmpC | | CIB132-3 |
| E. coli | S-LysC, DapA, LysA, Asd, DapB, AspC, TetA, CadA, OmpE | | CIB169-3 |
| E. coli | S-LysC, DapA, LysA, Asd, DapB, AspC, TetA, CadA, OmpF | | CIB133-3 |
| E. coli | S-LysC, DapA, LysA, Asd, DapB, AspC, TetA, CadA, OmpG | | CIB179-3 |
| E. coli | S-LysC, DapA, LysA, Asd, DapB, AspC, TetA, CadA, OmpW | | CIB180-3 |
| E. coli | S-LysC, DapA, LysA, Asd, DapB, AspC, TetA, CadA, OmpX | | CIB172-3 |

Table of primer sequences used in Examples.

| Name | Sequence (5'-3') |
|---|---|
| cadA-F | ggcgagctcacacaggaaacagaccatgaacgttattgcaatattgaatcac (SEQ ID NO: 39) |
| cadA-R | ggctctagaccacttcccttgtacgagc (SEQ ID NO: 40) |
| ompA-F | ggcgagctcacacaggaaacagaccATGAAAAAGACAGCTATCGC (SEQ ID NO: 41) |
| ompA-R | ggctctagaACCAGACGAGAACTTAAGCC (SEQ ID NO: 42) |
| ompC-F | ggcgagctcacacaggaaacagaccATGAAAGTTAAAGTACTGTCCCTC (SEQ ID NO: 43) |
| ompC-R | ggctctagaTTAGAACTGGTAAACCAGACC (SEQ ID NO: 44) |
| ompF-F | ggcgagctcacacaggaaacagaccATGATGAAGCGCAATATTCTG (SEQ ID NO: 45) |
| ompF-R | ggctctagaGCATTTAACAAAGAGGTGTGC (SEQ ID NO: 46) |
| ompX-F | ggcgagctcacacaggaaacagaccATGAAAAAAATTGCATGTCTTTCAG (SEQ ID NO: 47) |
| ompX-R | ggctctagaTTAGAAGCGGTAACCAACAC (SEQ ID NO: 48) |
| ompE-F | ggcgagctcacacaggaaacagaccATGAAAAAGAGCACTCTGGC (SEQ ID NO: 49) |
| ompE-R | ggctctagaTTAAAACTGATACGTCATGCCAAC (SEQ ID NO: 50) |
| ompG-F | ggcgagctcacacaggaaacagaccATGAAAAAGTTATTACCTGTACC (SEQ ID NO: 51) |
| ompG-R | ggctctagaTCAGAACGAGTAATTTACGC (SEQ ID NO: 52) |
| ompW-F | ggcgagctcacacaggaaacagaccATGAAAAAGTTAACAGTGGCG (SEQ ID NO: 53) |
| ompW-R | ggctctagaTTAAAAACGATATCCTGCTGAG (SEQ ID NO: 54) |
| psyn-1 | ggcgaattcagtttattatgacatgtagtgaggggggctggtataatgagctcggtacccggggat (SEQ ID NO: 55) |
| psyn-2 | ggcagtactcaaccaagtcattctgagaatagtg (SEQ ID NO: 56) |
| tetA-F | ggcgagctcacacaggaaacagaccATGAAATCTAACAATGCGCTCATC (SEQ ID NO: 57) |
| tetA-R | ggctctagaTCAACGACAGGAGCACGATC (SEQ ID NO: 58) |

Table of primer sequences used in Examples.

| Name | Sequence (5'-3') |
|---|---|
| lysC-F | ggcgagctcacacaggaaacagaccatgtctgaaattgttgtctcc (SEQ ID NO: 59) |
| lysC-R | ggcggatccttactcaaacaaattactatgcag (SEQ ID NO: 60) |
| dapA-F | ggcggatccacacaggaaacagaccatgttcacgggaagtattgtc (SEQ ID NO: 61) |
| dapA-R | ggctctagattacagcaaaccggcatgc (SEQ ID NO: 62) |
| lysA-F | ggctctagaacacaggaaacagaccatgccacattcactgttcagc (SEQ ID NO: 63) |
| lysA-R | ggcgtcgacttaaagcaattccagcgccag (SEQ ID NO: 64) |
| tetA-F3 | ggcctcgagagtttattcttgacatgtagtgagg (SEQ ID NO: 65) |
| tetA-R3 | ggcgcatgctcaacgacaggagcacgatc (SEQ ID NO: 66) |
| 318-F | cagcctgaatatactgcattctc (SEQ ID NO: 67) |
| 318-R | gagaatgcagtatattcaggctg (SEQ ID NO: 68) |
| 323-F | gcattctcgcgatttcctcg (SEQ ID NO: 69) |
| 323-R | cgaggaaatcgcgagaatgc (SEQ ID NO: 70) |
| SlysC-F | ggcgagctcacacaggaaacagaccatgggcttagttgtgcagaaa (SEQ ID NO: 71) |
| SlysC-R | ggcggatccttaacgacctgtgccgccata (SEQ ID NO: 72) |
| asd-F | ggcgagctcacacaggaaacagaccatgaaaaatgttggttttatcgg (SEQ ID NO: 73) |
| asd-R | ggcggatccttacgccagttgacgaagc (SEQ ID NO: 74) |
| dapB-F | ggcacacaggaaacagaccatgcatgatgcaaacatccg (SEQ ID NO: 75) |
| dapB-R | ggctctagattacaaattattgagatcaagtacatctc- (SEQ ID NO: 76) |
| dapD-F | ggctctagaacacaggaaacagaccatgcagcagttacagaacat (SEQ ID NO: 77) |
| dapD-R | ggcgcatgcttagtcgatggtacgcagca (SEQ ID NO: 78) |
| aspC-F | ggctctagaacacaggaaacagaccatgtttgagaacattaccgcc (SEQ ID NO: 79) |
| aspC-R | ggcgcatgcgacctcgaggtagtcgacttacagcactgccacaatcg (SEQ ID NO: 80) |
| LAL-F | ggcggtaccagtttattcttgacatgtagtgagg (SEQ ID NO: 81) |
| LAL-R | ggcgggcccttaaagcaattccagcgcca (SEQ ID NO: 82) |
| ABC-F | ggcgggccctgctggccttttgctcacat (SEQ ID NO: 83) |
| ABCT-R | ggcggtacctcaacgacaggagcacgatc (SEQ ID NO: 84) |
| SAL-F | ggcggtaccagtttattcttgacatgtagtgagg (SEQ ID NO: 85) |
| SAL-R | ggcgggcccttaaagcaattccagcgcca (SEQ ID NO: 86) |
| ompA-F2 | ggctctagaacacaggaaacagaccATGAAAAAGACAGCTATCGC (SEQ ID NO: 87) |
| ompA-R2 | ggcaagcttACCAGACGAGAACTTAAGCC (SEQ ID NO: 88) |
| ompC-F2 | ggctctagaacacaggaaacagaccATGAAAGTTAAAGTACTGTCCCTC (SEQ ID NO: 89) |
| ompC-R2 | ggcaagcttTTAGAACTGGTAAACCAGACC (SEQ ID NO: 90) |
| ompF-F2 | ggctctagaacacaggaaacagaccATGATGAAGCGCAATATTCTG (SEQ ID NO: 91) |
| ompF-R2 | ggcaagcttGCATTTAACAAAGAGGTGTGC (SEQ ID NO: 92) |
| ompX-F2 | ggctctagaacacaggaaacagaccATGAAAAAAATTGCATGTCTTTCAG (SEQ ID NO: 93) |
| ompX-R2 | ggcaagcttTTAGAAGCGGTAACCAACAC (SEQ ID NO: 94) |
| ompE-F2 | ggctctagaacacaggaaacagaccATGAAAAAGAGCACTCTGGC (SEQ ID NO: 95) |
| ompE-R2 | ggcaagcttTTAAAACTGATACGTCATGCCAAC (SEQ ID NO: 96) |
| ompG-F2 | ggctctagaacacaggaaacagaccATGAAAAAGTTATTACCCTGTACC (SEQ ID NO: 97) |
| ompG-R2 | ggcaagcttTCAGAACGAGTAATTTACGC (SEQ ID NO: 98) |
| ompW-F2 | ggctctagaacacaggaaacagaccATGAAAAAGTTAACAGTGGCG (SEQ ID NO: 99) |
| ompW-R2 | ggcaagcttTTAAAAACGATATCCTGCTGAG (SEQ ID NO: 100) |
| ybjE-F | ggctctagaacacaggaaacagaccATGTTTTCTGGGCTGTTAATCA (SEQ ID NO: 101) |
| ybjE-R | ggcaagcttGATCTACCGCCAGAGAGGTA (SEQ ID NO: 102) |

Illustrative Sequences

*Escherichia coli* cadA nucleic acid sequence
SEQ ID NO: 1
ATGAACGTTATTGCAATATTGAATCACATGGGGGTTTATTTTAAAGAAG
AACCCATCCGTGAACTTCATCGCGCGCTTGAACGTCTGAACTTCCAGAT
TGTTTACCCGAACGACCGTGACGACTTATTAAAACTGATCGAAAACAAT
GCGCGTCTGTGCGGCGTTATTTTTGACTGGGATAAATATAATCTCGAGC
TGTGCGAAGAAATTAGCAAAATGAACGAGAACCTGCCGTTGTACGCGTT
CGCTAATACGTATTCCACTCTCGATGTAAGCCTGAATGACCTGCGTTTA
CAGATTAGCTTCTTTGAATATGCGCTGGGTGCTGCTGAAGATATTGCTA
ATAAGATCAAGCAGACCACTGACGAATATATCAACACTATTCTGCCTCC
GCTGACTAAAGCACTGTTTAAATATGTTCGTGAAGGTAAATATACTTTC
TGTACTCCTGGTCACATGGGCGGTACTGCATTCCAGAAAAGCCCGGTAG
GTAGCCTGTTCTATGATTTCTTTGGTCCGAATACCATGAAATCTGATAT
TTCCATTTCAGTATCTGAACTGGGTTCTCTGCTGGATCACAGTGGTCCA
CACAAAGAAGCAGAACAGTATATCGCTCGCGTCTTTAACGCAGACCGCA
GCTACATGGTGACCAACGGTACTTCCACTGCGAACAAAATTGTTGGTAT
GTACTCTGCTCCAGCAGGCAGCACCATTCTGATTGACCGTAACTGCCAC
AAATCGCTGACCCACCTGATGATGATGAGCGATGTTACGCCAATCTATT
TCCGCCCGACCCGTAACGCTTACGGTATTCTTGGTGGTATCCCACACGAG
TGAATTCCAGCACGCTACCATTGCTAAGCGCGTGAAAGAAACACCAAAC
GCAACCTGGCCGGTACATGCTGTAATTACCAACTCTACCTATGATGGTC
TGCTGTACAACACCGACTTCATCAAGAAAACACTGGATGTGAAATCCAT
CCACTTTGACTCCGCGTGGGTGCCTTACACCAACTTCTCACCGATTTAC
GAAGGTAAATGCGGTATGAGCGGTGGCCGTGTAGAAGGGAAAGTGATTT
ACGAAACCCAGTCCACTCACAAACTGCTGGCGGCGTTCTCTCAGGCTTC
CATGATCCACGTTAAAGGTGACGTAAACGAAGAAACCTTTAACGAAGCC
TACATGATGCACACCACCACTTCTCCGCACTACGGTATCGTGGCGTCCA
CTGAAACCGCTGCGGCGATGATGAAAGGCAATGCAGGTAAGCGTCTGAT
CAACGGTTCTATTGAACGTGCGATCAAATTCCGTAAAGAGATCAAACGT
CTGAGAACGGAATCTGATGGCTGGTTCTTTGATGTATGGCAGCCGGATC
ATATCGATACGACTGAATGCTGGCCGCTGCGTTCTGACAGCACCTGGCA
CGGCTTCAAAAACATCGATAACGAGCACATGTATCTTGACCCGATCAAA
GTCACCCTGCTGACTCCGGGGATGGAAAAAGACGGCACCATGAGCGACT
TTGGTATTCCGCCAGCATCGTGGCGAAATACCTCGACGAACATGGCAT
CGTTGTTGAGAAAACCGGTCCGTATAACCTGCTGTTCCTGTTCAGCATC
GGTATCGATAAGACCAAAGCACTGAGCCTGCTGCGTGCTCTGACTGACT
TTAAACGTGCGTTCGACCTGAACCTGCGTGTGAAAAACATGCTGCCGTC
TCTGTATCGTGAAGATCCTGAATTCTATGAAAACATGCGTATTCAGGAA
CTGGCTCAGAATATCCACAAACTGATTGTTCACCACAATCTGCCGGATC
TGATGTATCGCGCATTTGAAGTGCTGCCGACGATGGTAATGACTCCGTA
TGCTGCATTCCAGAAAGAGCTGCACGGTATGACCGAAGAAGTTTACCTC
GACGAAATGGTAGGTCGTATTAACGCCAATATGATCCTTCCGTACCCGC
CGGGAGTTCCTCTGGTAATGCCGGGTGAAATGATCACCGAAGAAAGCCG
TCCGGTTCTGGAGTTCCTGCAGATGCTGTGTGAAATCGGCGCTCACTAT
CCGGGCTTTGAAACCGATATTCACGGTGCATACCGTCAGGCTGATGGCC
GCTATACCGTTAAGGTATTGAAAGAAGAAAGCAAAAAATAA CadA polypeptide sequence
SEQ ID NO: 2
MNVIAILNHMGVYFKEEPIRELHRALERLNFQIVYPNDRDDLLKLIENN
ARLCGVIFDWDKYNLELCEEISKMNENLPLYAFANTYSTLDVSLNDLRL
QISFFEYALGAAEDIANKIKQTTDEYINTILPPLTKALFKYVREGKYTF
CTPGHMGGTAFQKSPVGSLFYDFFGPNTMKSDISISVSELGSLLDHSGP
HKEAEQYIARVFNADRSYMVTNGTSTANKIVGMYSAPAGSTILIDRNCH
KSLTHLMMMSDVTPIYFRPTRNAYGILGGIPQSEFQHATIAKRVKETPN
ATWPVHAVITNSTYDGLLYNTDFIKKTLDVKSIHFDSAWVPYTNFSPIY
EGKCGMSGGRVEGKVIYETQSTHKLLAAFSQASMIHVKGDVNEETFNEA
YMMHTTTSPHYGIVASTETAAAMMKGNAGKRLINGSIERAIKFRKEIKR
LRTESDGWFFDVWQPDHIDTTECWPLRSDSTWHGFKNIDNEHMYLDPIK
VTLLTPGMEKDGTMSDFGIPASIVAKYLDEHGIVVEKTGPYNLLFLFSI
GIDKTKALSLLRALTDFKRAFDLNLRVKNMLPSLYREDPEFYENMRIQE
LAQNIHKLIVHHNLPDLMYRAFEVLPTMVMTPYAAFQKELHGMTEEVYL
DEMVGRINANMILPYPPGVPLVMPGEMITEESRPVLEFLQMLCEIGAHY
PGFETDIHGAYRQADGRYTVKVLKEESKK

*E. coli* ompA nucleic acid sequence
SEQ ID NO: 3
ATGAAAAAGACAGCTATCGCGATTGCAGTGGCACTGGCTGGTTTCGCTA
CCGTAGCGCAGGCCGCTCCGAAAGATAACACCTGGTACACTGGTGCTAA
ACTGGGCTGGTCCCAGTACCATGACACTGGTTTCATCAACAACAATGGC
CCGACCCATGAAAACCAACTGGGCGCTGGTGCTTTTGGTGGTTACCAGG
TTAACCCGTATGTTGGCTTTGAAATGGGTTACGACTGGTTAGGTCGTAT
GCCGTACAAAGGCAGCGTTGAAAACGGTGCATACAAAGCTCAGGGCGTT
CAACTGACCGCTAAACTGGGTTACCCAATCACTGACGACCTGGACATCT
ACACTCGTCTGGGTGGCATGGTATGGCGTGCAGACACTAAATCCAACGT
TTATGGTAAAAACCACGACACCGGCGTTTCTCCGGTCTTCGCTGGCGGT
GTTGAGTACGCGATCACTCCTGAAATCGCTACCCGTCTGGAATACCAGT
GGACCAACAACATCGGTGACGCACACACCATCGGCACTCGTCCGGACAA
CGGCATGCTGAGCCTGGGTGTTTCCTACCGTTTCGGTCAGGGCGAAGCA
GCTCCAGTAGTTGCTCCGGCTCCAGCTCCGGCACCGGAAGTACAGACCA
AGCACTTCACTCTGAAGTCTGACGTTCTGTTCAACTTCAACAAAGCAAC
CCTGAAACCGGAAGGTCAGGCTGCTCTGGATCAGCTGTACAGCCAGCTG
AGCAACCTGGATCCGAAAGACGGTTCCGTAGTTGTTCTGGGTTACACCG
ACCGCATCGGTTCTGACGCTTACAACCAGGGTCTGTCCGAGCGCCGTGC
TCAGTCTGTTGTTGATTACCTGATCTCCAAAGGTATCCCGGCAGACAAG -continued

ATCTCCGCACGTGGTATGGGCGAATCCAACCCGGTTACTGGCAACACCT

GTGACAACGTGAAACAGCGTGCTGCACTGATCGACTGCCTGGCTCCGGA

TCGTCGCGTAGAGATCGAAGTTAAAGGTATCAAAGACGTTGTAACTCAG

CCGCAGGCTTAA

OmpA polypeptide sequence (underlined sequence is a signal peptide that is cleaved in the mature protein)
SEQ ID NO: 4
<u>MKKTAIAIAVALAGFATVAQA</u>APKDNTWYTGAKLGWSQYHDTGFINNNG

PTHENQLGAGAFGGYQVNPYVGFEMGYDWLGRMPYKGSVENGAYKAQGV

QLTAKLGYPITDDLDIYTRLGGMVWRADTKSNVYGKNHDTGVSPVFAGG

VEYAITPEIATRLEYQWTNNIGDAHTIGTRPDNGMLSLGVSYRFGQGEA

APVVAPAPAPAPEVQTKHFTLKSDVLFNFNKATLKPEGQAALDQLYSQL

SNLDPKDGSVVVLGYTDRIGSDAYNQGLSERRAQSVVDYLISKGIPADK

ISARGMGESNPVTGNTCDNVKQRAALIDCLAPDRRVEIEVKGIKDVVTQ

PQA

E. coli ompC nucleic acid sequence
SEQ ID NO: 5
ATGAAAGTTAAAGTACTGTCCCTCCTGGTCCCAGCTCTGCTGGTAGCAG

GCGCAGCAAACGCTGCTGAAGTTTACAACAAAGACGGCAACAAATTAGA

TCTGTACGGTAAAGTAGACGGCCTGCACTATTTCTCTGACAACAAAGAT

GTAGATGGCGACCAGACCTACATGCGTCTTGGCTTCAAAGGTGAAACTC

AGGTTACTGACCAGCTGACCGGTTACGGCCAGTGGGAATATCAGATCCA

GGGCAACAGCGCTGAAAACGAAAACAACTCCTGGACCCGTGTGGCATTC

GCAGGTCTGAAATTCCAGGATGTGGGTTCTTTCGACTACGGTCGTAACT

ACGGCGTTGTTTATGACGTAACTTCCTGGACCGACGTACTGCCAGAATT

CGGTGGTGACACCTACGGTTCTGACAACTTCATGCAGCAGCGTGGTAAC

GGCTTCGCGACCTACCGTAACACTGACTTCTTCGGTCTGGTTGACGGCC

TGAACTTTGCTGTTCAGTACCAGGGTAAAAACGGCAACCCATCTGGTGA

AGGCTTTACTAGTGGCGTAACTAACAACGGTCGTGACGCACTGCGTCAA

AACGGCGACGGCGTCGGCGGTTCTATCACTTATGATTACGAAGGTTTCG

GTATCGGTGGTGCGATCTCCAGCTCCAAACGTACTGATGCTCAGAACAC

CGCTGCTTACATCGGTAACGGCGACCGTGCTGAAACCTACACTGGTGGT

CTGAAATACGACGCTAACAACATCTACCTGGCTGCTCAGTACACCCAGA

CCTACAACGCAACTCGCGTAGGTTCCCTGGGTTGGGCGAACAAAGCACA

GAACTTCGAAGCTGTTGCTCAGTACCAGTTCGACTTCGGTCTGCGTCCG

TCCCTGGCTTACCTGCAGTCTAAAGGTAAAAACCTGGGTCGTGGCTACG

ACGACGAAGATATCCTGAAATATGTTGATGTTGGTGCTACCTACTACTT

CAACAAAAACATGTCCACCTACGTTGACTACAAAATCAACCTGCTGGAC

GACAACCAGTTCACTCGTGACGCTGGCATCAACACTGATAACATCGTAG

CTCTGGGTCTGGTTTACCAGTTCTAA

OmpC polypeptide sequence (underlined sequence is a signal peptide that is cleaved in the mature protein)
SEQ ID NO: 6
<u>MKVKVLSLLVPALLVAGAANA</u>AEVYNKDGNKLDLYGKVDGLHYFSDNKD

VDGDQTYMRLGFKGETQVTDQLTGYGQWEYQIQGNSAENENNSWTRVAF

AGLKFQDVGSFDYGRNYGVVYDVTSWTDVLPEFGGDTYGSDNFMQQRGN

GFATYRNTDFFGLVDGLNFAVQYQGKNGNPSGEGFTSGVTNNGRDALRQ

NGDGVGGSITYDYEGFGIGGAISSSKRTDAQNTAAYIGNGDRAETYTGG

LKYDANNIYLAAQYTQTYNATRVGSLGWANKAQNFEAVAQYQFDFGLRP

SLAYLQSKGKNLGRGYDDEDILKYVDVGATYYFNKNMSTYVDYKINLLD

DNQFTRDAGINTDNIVALGLVYQF

E. coli ompF nucleic acid sequence
SEQ ID NO: 7
ATGAAGCGCAATATTCTGGCAGTGATCGTCCCTGCTCTGTTAGTAGCAG

GTACTGCAAACGCTGCAGAAATCTATAACAAAGATGGCAACAAAGTAGA

TCTGTACGGTAAAGCTGTTGGTCTGCATTATTTTTCCAAGGGTAACGGT

GAAAACAGTTACGGTGGCAATGGCGACATGACCTATGCCCGTCTTGGTT

TTAAAGGGGAAACTCAAATCAATTCCGATCTGACCGGTTATGGTCAGTG

GGAATATAACTTCCAGGGTAACAACTCTGAAGGCGCTGACGCTCAAACT

GGTAACAAAACGCGTCTGGCATTCGCGGGTCTTAAATACGCTGACGTTG

GTTCTTTCGATTACGGCCGTAACTACGGTGTGGTTTATGATGCACTGGG

TTACACCGATATGCTGCCAGAATTTGGTGGTGATACTGCATACAGCGAT

GACTTCTTCGTTGGTCGTGTTGGCGGCGTTGCTACCTATCGTAACTCCA

ACTTCTTTGGTCTGGTTGATGGCCTGAACTTCGCTGTTCAGTACCTGGG

TAAAAACGAGCGTGACACTGCACGCCGTTCTAACGGCGACGGTGTTGGC

GGTTCTATCAGCTACGAATACGAAGGCTTTGGTATCGTTGGTGCTTATG

GTGCAGCTGACCGTACCAACCTGCAAGAAGCTCAACCTCTTGGCAACGG

TAAAAAAGCTGAACAGTGGGCTACTGGTCTGAAGTACGACGCGAACAAC

ATCTACCTGGCAGCGAACTACGGTGAAACCCGTAACGCTACGCCGATCA

CTAATAAATTTACAAACACCAGCGGCTTCGCCAACAAAACGCAAGACGT

TCTGTTAGTTGCGCAATACCAGTTCGATTTCGGTCTGCGTCCGTCCATC

GCTTACACCAAATCTAAAGCGAAAGACGTAGAAGGTATCGGTGATGTTG

ATCTGGTGAACTACTTTGAAGTGGGCGCAACCTACTACTTCAACAAAAA

CATGTCCACCTATGTTGACTACATCATCAACCAGATCGATTCTGACAAC

AAACTGGGCGTAGGTTCAGACGACACCGTTGCTGTGGGTATCGTTTACC

AGTTCTAA

OmpF polypeptide sequence (underlined sequence is a signal peptide that is cleaved in the mature protein)
SEQ ID NO: 8
<u>MKRNILAVIVPALLVAGTANA</u>AEIYNKDGNKVDLYGKAVGLHYFSKGNG

ENSYGGNGDMTYARLGFKGETQINSDLTGYGQWEYNFQGNNSEGADAQT

GNKTRLAFAGLKYADVGSFDYGRNYGVVYDALGYTDMLPEFGGDTAYSD

DFFVGRVGGVATYRNSNFFGLVDGLNFAVQYLGKNERDTARRSNGDGVG

-continued
GSISYEYEGFGIVGAYGAADRTNLQEAQPLGNGKKAEQWATGLKYDANN
IYLAANYGETRNATPITNKFTNTSGFANKTQDVLLVAQYQFDFGLRPST
AYTKSKAKDVEGIGDVDLVNYFEVGATYYFNKNMSTYVDYTINQIDSDN
KLGVGSDDTVAVGIVYQF

*E. coli* ompX nucleic acid sequence
SEQ ID NO: 9
ATGAAAAAAATTGCATGTCTTTCAGCACTGGCCGCAGTTCTGGCTTTCA

CCGCAGGTACTTCCGTAGCTGCGACTTCTACTGTAACTGGCGGTTACGC

ACAGAGCGACGCTCAGGGCCAAATGAACAAAATGGGCGGTTTCAACCTG

AAATACCGCTATGAAGAAGACAACAGCCCGCTGGGTGTGATCGGTTCTT

TCACTTACACCGAGAAAGCCGTACTGCAAGCTCTGGTGACTACAACAA

AAACCAGTACTACGGCATCACTGCTGGTCCGGCTTACCGCATTAACGAC

TGGGCAAGCATCTACGGTGTAGTGGGTGTGGGTTATGGTAAATTCCAGA

CCACTGAATACCCGACCTACAAACACGACACCAGCGACTACGGTTTCTC

CTACGGTGCGGGTCTGCAGTTCAACCCGATGGAAAACGTTGCTCTGGAC

TTCTCTTACGAGCAGAGCCGTATTCGTAGCGTTGACGTAGGCACCTGGA

TTGCCGGTGTTGGTTACCGCTTCTAA

OmpX polypeptidesequence (underlined sequence is
a signal peptide that is cleaved in the mature
protein)
SEQ ID NO: 10
<u>MKKIACLSALAAVLAFTAGTSVA</u>ATSTVTGGYAQSDAQGQMNKMGGFNL

KYRYEEDNSPLGVIGSFTYTEKSRTASSGDYNKNQYYGITAGPAYRIND

WASIYGVVGVGYGKFQTTEYPTYKHDTSDYGFSYGAGLQFNPMENVALD

FSYEQSRIRSVDVGTWIAGVGYRF

*E coli* ompE nucleic acid sequence
SEQ ID NO: 11
ATGAAAAAGAGCACTCTGGCATTAGTGGTGATGGGCATTGTGGCATCTG

CATCTGTACAGGCTGCAGAAATATATAATAAAGACGGTAATAAACTGGA

TGTCTATGGCAAAGTTAAAGCCATGCATTATATGAGTGATAACGCCAGT

AAAGATGGCGACCAGAGTTATATCCGTTTTGGTTTCAAAGGCGAAACAC

AAATTAACGATCAACTGACTGGTTATGGTCGTTGGGAAGCAGAGTTTGC

CGGTAATAAAGCAGAGAGTGATACTGCACAGCAAAAAACGCGTCTCGCT

TTTGCCGGGTTGAAATATAAAGATTTGGGTTCTTTCGATTATGGTCGTA

ACCTGGGGGCGTTGTATGACGTGGAAGCCTGGACCGATATGTTCCCGGA

ATTTGGTGGCGATTCCTCGGCGCAGACCGACAACTTTATGACCAAACGC

GCCAGCGGTCTGGCGACGTATCGGAACACCGACTTCTTCGGCGTTATCG

ATGGCCTGAACTTAACCCTGCAATATCAAGGGAAAAACGAAAACCGCGA

CGTTAAAAAGCAAACGGCGATGGCTTCGGCACGTCATTGACATATGAC

TTTGGCGGCAGCGATTTCGCCATTAGTGGGCCTATACCAACTCAGATC

GCACCAACGAGCAGAACCTGCAAAGCCGTGGCACAGGCAAGCGTGCAGA

AGCATGGGCAACAGGTCTGAAATACGATGCCAATAATATTTATCTGGCA

ACTTTCTATTCTGAAACACGCAAAATGACGCCAATAACTGGCGGCTTTG

CCAATAAGACACAGAACTTTGAAGCGGTCGCTCAATACCAGTTTGACTT

TGGTCTGCGTCCATCGCTGGGTTATGTCTTATCGAAAGGGAAAGATATT

-continued
GAAGGTATCGGTGATGAAGATCTGGTCAATTATATCGACGTCGGTGCTA

CGTATTATTTCAACAAAAATATGTCAGCGTTTGTTGATTATAAAATCAA

CCAACTGGATAGCGATAACAAATTGAATATTAATAATGATGATATTGTC

GCGGTTGGCATGACGTATCAGTTTTAA

OmpE polypeptide sequence (underlined sequence is
a signal peptide that is cleaved in the mature
protein)
SEQ ID NO: 12
<u>MKKSTLALVVMGIVASASVQA</u>AEIYNKDGNKLDVYGKVKAMHYMSDNAS

KDGDQSYIRFGFKGETQINDQLTGYGRWEAEFAGNKAESDTAQQKTRLA

FAGLKYKDLGSFDYGRNLGALYDVEAWTDMFPEFGGDSSAQTDNFMTKR

ASGLATYRNTDFFGVIDGLNLTLQYQGKNENRDVKKQNGDGFGTSLTYD

FGGSDFAISGAYTNSDRTNEQNLQSRGTGKRAEAWATGLKYDANNIYLA

TFYSETRKMTPITGGFANKTQNFEAVAQYQFDFGLRPSLGYVLSKGKDI

EGIGDEDLVNYIDVGATYYFNKNMSAFVDYKINQLDSDNKLNINNDDIV

AVGMTYQF

*E. coli* ompG nucleic acid sequence
SEQ ID NO: 13
ATGAAAAAGTTATTACCCTGTACCGCACTGGTGATGTGTGCGGGAATGG

CCTGCGCACAGGCCGAGGAAAGGAACGACTGGCACTTTAATATCGGCGC

GATGTACGAAATAGAAAACGTCGAGGGTTATGGCGAAGATATGGATGGG

CTGGCGGAGCCTTCAGTCTATTTTAATGCCGCCAACGGGCCGTGGAGAA

TTGCTCTGGCCTATTATCAGGAAGGGCCGGTAGATTATAGCGCGGGTAA

ACGTGGAACGTGGTTTGATCGCCCGGAGCTGGAGGTGCATTATCAGTTC

CTCGAAAACGATGATTTCAGTTTCGGCCTGACCGGCGGTTTCCGTAATT

ATGGTTATCACTACGTTGATGAACCGGGTAAAGACACGGCGAATATGCA

GCGCTGGAAAATCGCGCCAGACTGGGATGTGAAACTGACTGACGATTTA

CGTTTCAACGGTTGGTTGTCGATGTATAAATTTGCCAACGATCTGAACA

CTACCGGTTACGCTGATACCCGTGTCGAAACGGAAACAGGTCTGCAATA

TACCTTCAACGAAACGGTTGCCTTGCGAGTGAACTATTATCTCGAGCGC

GGCTTCAATATGGACGACAGCCGCAATAACGGTGAGTTTTCCACGCAAG

AAATTCGCGCCTATTTGCCGCTGACGCTCGGCAACCACTCGGTGACGCC

GTATACGCGCATTGGGCTGGATCGCTGGAGTAACTGGGACTGGCAGGAT

GATATTGAACGTGAAGGCCATGATTTTAACCGTGTAGGTTTATTTTACG

GTTATGATTTCCAGAACGGACTTTCCGTTTCGCTGGAATACGCGTTTGA

GTGGCAGGATCACGACGAAGGCGACAGTGATAAATTCCATTATGCAGGT

GTCGGCGTAAATTACTCGTTCTGA

OmpG polypeptide sequence (underlined sequence is
a signal peptide that is cleaved in the mature
protein)
SEQ ID NO: 14
<u>MKKLLPCTALVMCAGMACAQA</u>EERNDWHENIGAMYEIENVEGYGEDMDG

LAEPSVYFNAANGPWRIALAYYQEGPVDYSAGKRGTWFDRPELEVHYQF

LENDDFSFGLTGGFRNYGYHYVDEPGKDTANMQRWKIAPDWDVKLTDDL

RENGWLSMYKFANDLNTTGYADTRVETETGLQYTFNETVALRVNYYLER

-continued
GFNMDDSRNNGEFSTQEIRAYLPLTLGNHSVTPYTRIGLDRWSNWDWQD
DIEREGHDENRVGLFYGYDFQNGLSVSLEYAFEWQDHDEGDSDKFHYAG
VGVNYSF E. coli ompW nucleic acid sequence
SEQ ID NO: 15
ATGAAAAAGTTAACAGTGGCGGCTTTGGCAGTAACAACTCTTCTCTCTG
GCAGTGCCTTTGCGCATGAAGCAGGCGAATTTTTTATGCGTGCAGGTTC
TGCAACCGTACGTCCAACAGAAGGTGCTGGTGGTACGTTAGGAAGTCTG
GGTGGATTCAGCGTGACCAATAACACGCAACTGGGCCTTACGTTTACTT
ATATGGCGACCGACAACATTGGTGTGGAATTACTGGCAGCGACGCCGTT
CCGCCATAAAATCGGCACCCGGGCGACCGGCGATATTGCAACCGTTCAT
CATCTGCCACCAACACTGATGGCGCAGTGGTATTTTGGTGATGCCAGCA
GCAAATTCCGTCCTTACGTTGGGGCAGGTATTAACTACACCACCTTCTT
TGATAATGGATTTAACGATCATGGCAAAGAGGCAGGGCTTTCCGATCTC
AGTCTGAAAGATTCCTGGGGAGCTGCCGGGCAGGTGGGGGTTGATTATC
TGATTAACCGTGACTGGTTGGTTAACATGTCAGTGTGGTACATGGATAT
CGATACCACCGCCAATTATAAGCTGGGCGGTGCACAGCAACACGATAGC
GTACGCCTCGATCCGTGGGTGTTTATGTTCTCAGCAGGATATCGTTTTT
AA OmpW polypeptide sequence (underlined sequence is
a signal peptide that is cleaved in the mature
protein)
SEQ ID NO: 16
<u>MKKLTVAALAVTTLLSGSAFA</u>HEAGEFFMRAGSATVRPTEGAGGTLGSL
GGFSVTNNTQLGLTFTYMATDNIGVELLAATPERHKIGTRATGDIATVH
HLPPTLMAQWYEGDASSKFRPYVGAGINYTTFEDNGENDHGKEAGLSDL
SLKDSWGAAGQVGVDYLINRDWLVNMSVWYMDIDTTANYKLGGAQQHDS
VRLDPWVFMFSAGYRF synthetic promoter nucleic acid sequence
SEQ ID NO: 17
AGTTTATTCTTGACATGTAGTGAGGGGGCTGGTATAAT tetA nucleic acid sequence
SEQ ID NO: 18
ATGAAATCTAACAATGCGCTCATCGTCATCCTCGGCACCGTCACCCTGG
ATGCTGTAGGCATAGGCTTGGTTATGCCGGTACTGCCGGGCCTCTTGCG
GGATATCGTCCATTCCGACAGCATCGCCAGTCACTATGGCGTGCTGCTA
GCGCTATATGCGTTGATGCAATTTCTATGCGCACCCGTTCTCGGAGCAC
TGTCCGACCGCTTTGGCCGCCGCCCAGTCCTGCTCGCTTCGCTACTTGG
AGCCACTATCGACTACGCGATCATGGCGACCACACCCGTCCTGTGGATC
CTCTACGCCGGACGCATCGTGGCCGGCATCACCGGCGCCACAGGTGCGG
TTGCTGGCGCCTATATCGCCGACATCACCGATGGGGAAGATCGGGCTCG
CCACTTCGGGCTCATGAGCGCTTGTTTCGGCGTGGGTATGGTGGCAGGC
CCCGTGGCCGGGGGACTGTTGGGCGCCATCTCCTTGCATGCACCATTCC
TTGCGGCGGCGGTGCTCAACGGCCTCAACCTACTACTGGGCTGCTTCCT
AATGCAGGAGTCGCATAAGGGAGAGCGTCGACCGATGCCCTTGAGAGCC
TTCAACCCAGTCAGCTCCTTCCGGTGGGCGCGGGGCATGACTATCGTCG CCGCACTTATGACTGTCTTCTTTATCATGCAACTCGTAGGACAGGTGCC
GGCAGCGCTCTGGGTCATTTTCGGCGAGGACCGCTTTCGCTGGAGCGCG
ACGATGATCGGCCTGTCGCTTGCGGTATTCGGAATCTTGCACGCCCTCG
CTCAAGCCTTCGTCACTGGTCCCGCCACCAAACGTTTCGGCGAGAAGCA
GGCCATTATCGCCGGCATGGCGGCCGACGCGCTGGGCTACGTCTTGCTG
GCGTTCGCGACGCGAGGCTGGATGGCCTTCCCCATTATGATTCTTCTCG
CTTCCGGCGGCATCGGGATGCCCGCGTTGCAGGCCATGCTGTCCAGGCA
GGTAGATGACGACCATCAGGGACAGCTTCAAGGATCGCTCGCGGCTCTT
ACCAGCCTAACTTCGATCATTGGACCGCTGATCGTCACGGCGATTTATG
CCGCCTCGGCGAGCACATGGAACGGGTTGGCATGGATTGTAGGCGCCGC
CCTATACCTTGTCTGCCTCCCCGCGTTGCGTCGCGGTGCATGGAGCCGG
GCCACCTCGACCTGA TetA polypeptide sequence
SEQ ID NO: 19
MKSNNALIVILGTVTLDAVGIGLVMPVLPGLLRDIVHSDSIASHYGVLL
ALYALMQFLCAPVLGALSDRFGRRPVLLASLLGATIDYAIMATTPVLWI
LYAGRIVAGITGATGAVAGAYIADITDGEDRARHFGLMSACFGVGMVAG
PVAGGLLGAISLHAPFLAAAVLNGLNLLLGCFLMQESHKGERRPMPLRA
FNPVSSFRWARGMTIVAALMTVFFIMQLVGQVPAALWVIFGEDRFRWSA
TMIGLSLAVFGILHALAQAFVTGPATKRFGEKQATIAGMAADALGYVLL
AFATRGWMAFPIMILLASGGIGMPALQAMLSRQVDDDHQGQLQGSLAAL
TSLTSIIGPLIVTAIYAASASTWNGLAWIVGAALYLVCLPALRRGAWSR
ATST lysC nucleic acid sequence
SEQ ID NO: 20
ATGTCTGAAATTGTTGTCTCCAAATTTGGCGGTACCAGCGTAGCTGATT
TTGACGCCATGAACCGCAGCGCTGATATTGTGCTTTCTGATGCCAACGT
GCGTTTAGTTGTCCTCTCGGCTTCTGCTGGTATCACTAATCTGCTGGTC
GCTTTAGCTGAAGGACTGGAACCTGGCGAGCGATTCGAAAAACTCGACG
CTATCCGCAACATCCAGTTTGCCATTCTGGAACGTCTGCGTTACCCGAA
CGTTATCCGTGAAGAGATTGAACGTCTGCTGGAGAACATTACTGTTCTG
GCAGAAGCGGCGGCGCTGGCAACGTCTCCGGCGCTGACAGATGAGCTGG
TCAGCCACGGCGAGCTGATGTCGACCCTGCTGTTTGTTGAGATCCTGCG
CGAACGCGATGTTCAGGCACAGTGGTTTGATGTACGTAAAGTGATGCGT
ACCAACGACCGATTTGGTCGTGCAGAGCCAGATATAGCCGCGCTGGCGG
AACTGGCCGCGCTGCAGCTGCTCCCACGTCTCAATGAAGGCTTAGTGAT
CACCCAGGGATTTATCGGTAGCGAAAATAAAGGTCGTACAACGACGCTT
GGCCGTGGAGGCAGCGATTATACGGCAGCCTTGCTGGCGGAGGCTTTAC
ACGCATCTCGTGTTGATATCTGGACCGACGTCCCGGGCATCTACACCAC
CGATCCACGCGTAGTTTCCGCAGCAAAACGCATTGATGAAATCGCGTTT
GCCGAAGCGGCAGAGATGGCAACTTTTGGTGCAAAAGTACTGCATCCG
CAACGTTGCTACCCGCAGTACGCAGCGATATCCCGGTCTTTGTCGGCTC -continued

```
CAGCAAAGACCCACGCGCAGGTGGTACGCTGGTGTGCAATAAAACTGAA
AATCCGCCGCTGTTCCGCGCTCTGGCGCTTCGTCGCAATCAGACTCTGC
TCACTTTGCACAGCCTGAATATGCTGCATTCTCGCGGTTTCCTCGCGGA
AGTTTTCGGCATCCTCGCGCGGCATAATATTTCGGTAGACTTAATCACC
ACGTCAGAAGTGAGCGTGGCATTAACCCTTGATACCACCGGTTCAACCT
CCACTGGCGATACGTTGCTGACGCAATCTCTGCTGATGGAGCTTTCCGC
ACTGTGTCGGGTGGAGGTGGAAGAAGGTCTGGCGCTGGTCGCGTTGATT
GGCAATGACCTGTCAAAAGCCTGCGGCGTTGGCAAAGAGGTATTCGGCG
TACTGGAACCGTTCAACATTCGCATGATTTGTTATGGCGCATCCAGCCA
TAACCTGTGCTTCCTGGTGCCCGGCGAAGATGCCGAGCAGGTGGTGCAA
AAACTGCATAGTAATTTGTTTGAGTAA
```

LysC polypeptide sequence
SEQ ID NO: 21
```
MSEIVVSKFGGTSVADFDAMNRSADIVLSDANVRLVVLSASAGITNLLV
ALAEGLEPGERFEKLDAIRNIQFAILERLRYPNVIREEIERLLENITVL
AEAAALATSPALTDELVSHGELMSTLLFVEILRERDVQAQWFDVRKVMR
TNDRFGRAEPDIAALAELAALQLLPRLNEGLVITQGFIGSENKGRTTTL
GRGGSDYTAALLAEALHASRVDIWTDVPGIYTTDPRVVSAAKRIDEIAF
AEAAEMATFGAKVLHPATLLPAVRSDIPVFVGSSKDPRAGGTLVCNKTE
NPPLFRALALRRNQTLLTLHSLNMLHSRGFLAEVFGILARHNISVDLIT
TSEVSVALTLDTTGSTSTGDTLLTQSLLMELSALCRVEVEEGLALVALI
GNDLSKACGVGKEVFGVLEPFNIRMICYGASSHNLCFLVPGEDAEQVVQ
KLHSNLFE
``` dapA nucleic acid sequence
SEQ ID NO: 22
```
ATGTTCACGGGAAGTATTGTCGCGATTGTTACTCCGATGGATGAAAAG
GTAATGTCTGTCGGGCTAGCTTGAAAAAACTGATTGATTATCATGTCGC
CAGCGGTACTTCGGCGATCGTTTCTGTTGGCACCACTGGCGAGTCCGCT
ACCTTAAATCATGACGAACATGCTGATGTGGTGATGATGACGCTGGATC
TGGCTGATGGGCGCATTCCGGTAATTGCCGGGACCGGCGCTAACGCTAC
TGCGGAAGCCATTAGCCTGACGCAGCGCTTCAATGACAGTGGTATCGTC
GGCTGCCTGACGGTAACCCCTTACTACAATCGTCCGTCGCAAGAAGGTT
TGTATCAGCATTTCAAAGCCATCGCTGAGCATACTGACCTGCCGCAAAT
TCTGTATAATGTGCCGTCCCGTACTGGCTGCGATCTGCTCCCGGAAACG
GTGGGCCGTCTGGCGAAAGTAAAAAATATTATCGGAATCAAAGAGGCAA
CAGGGAACTTAACGCGTGTAAACCAGATCAAAGAGCTGGTTTCAGATGA
TTTTGTTCTGCTGAGCGGCGATGATGCGAGCGCGCTGGACTTCATGCAA
TTGGGCGGTCATGGGGTTATTTCCGTTACGGCTAACGTCGCAGCGCGTG
ATATGGCCCAGATGTGCAAACTGGCAGCAGAAGGGCATTTTGCCGAGGC
ACGCGTTATTAATCAGCGTCTGATGCCATTACACAACAAACTATTTGTC
GAACCCAATCCAATCCCGGTGAAATGGGCATGTAAGGAACTGGGTCTTG
TGGCGACCGATACGCTGCGCCTGCCAATGACACCAATCACCGACAGTGG
TCGTGAGACGGTCAGAGCGGCGCTTAAGCATGCCGGTTTGCTGTAA
```

DapA polypeptide sequence
SEQ ID NO: 23
```
MFTGSIVAIVTPMDEKGNVCRASLKKLIDYHVASGTSAIVSVGTTGESA
TLNHDEHADVVMMTLDLADGRIPVIAGTGANATAEAISLTQRFNDSGIV
GCLTVTPYYNRPSQEGLYQHFKAIAEHTDLPQILYNVPSRTGCDLLPET
VGRLAKVKNIIGIKEATGNLTRVNQIKELVSDDFVLLSGDDASALDFMQ
LGGHGVISVTANVAARDMAQMCKLAAEGHFAEARVINQRLMPLHNKLFV
EPNPIPVKWACKELGLVATDTLRLPMTPITDSGRETVRAALKHAGLL
``` lysA nucleic acid sequence
SEQ ID NO: 24
```
ATGCCACATTCACTGTTCAGCACCGATACCGATCTCACCGCCGAAAATC
TGCTGCGTTTGCCCGCTGAATTTGGCTGCCCGGTGTGGGTCTACGATGC
GCAAATTATTCGTCGGCAGATTGCAGCGCTGAAACAGTTTGATGTGGTG
CGCTTTGCACAGAAAGCCTGTTCCAATATTCATATTTTGCGCTTAATGC
GTGAGCAGGGCGTGAAAGTGGATTCCGTCTCGTTAGGCGAAATAGAGCG
TGCGTTGGCGGCGGGTTACAATCCGCAAACGCACCCCGATGATATTGTT
TTTACGGCAGATGTTATCGATCAGGCGACGCTTGAACGCGTCAGTGAAT
TGCAAATTCCGGTGAATGCGGGTTCTGTTGATATGCTCGACCAACTGGG
CCAGGTTTCGCCAGGGCATCGGGTATGGCTGCGCGTTAATCCGGGGTTT
GGTCACGGACATAGCCAAAAAACCAATACCGGTGGCGAAAACAGCAAGC
ACGGTATCTGGTACACCGATCTGCCCGCCGCACTGGACGTGATACAACG
TCATCATCTGCAGCTGGTCGGCATTCACATGCACATTGGTTCTGGCGTT
GATTATGCCCATCTGGAACAGGTGTGTGGTGCTATGGTGCGTCAGGTCA
TCGAATTCGGTCAGGATTTACAGGCTATTTCTGCGGGCGGTGGGCTTTC
TGTTCCTTATCAACAGGGTGAAGAGGCGGTTGATACCGAACATTATTAT
GGTCTGTGGAATGCCGCGCGTGAGCAAATCGCCCGCCCATTTGGGCCACC
CTGTGAAACTGGAAATTGAACCGGGTCGCTTCCTGGTAGCGCAGTCTGG
CGTATTAATTACTCAGGTGCGGAGCGTCAAACAAATGGGGAGCCGCCAC
TTTGTGCTGGTTGATGCCGGGTTCAACGATCTGATGCGCCCGGCAATGT
ACGGTAGTTACCACCATATCAGTGCCCTGGCAGCTGATGGTCGTTCTCT
GGAACACGCGCCAACGGTGGAAACCGTCGTCGCCGGACCGTTATGTGAA
TCGGGCGATGTCTTTACCCAGCAGGAAGGGGGAAATGTTGAAACCCGCG
CCTTGCCGGAAGTGAAGGCAGGTGATTATCTGGTACTGCATGATACAGG
GGCATATGGCGCATCAATGTCATCCAACTACAATAGCCGTCCGCTGTTA
CCAGAAGTTCTGTTTGATAATGGTCAGGCGCGGTTGATTCGCCGTCGCC
AGACCATCGAAGAATTACTGGCGCTGGAATTGCTTTAA
```

LysA polypeptide sequence
SEQ ID NO: 25
```
MPHSLFSTDTDLTAENLLRLPAEFGCPVWVYDAQIIRRQIAALKQFDVV
RFAQKACSNIHILRLMREQGVKVDSVSLGEIERALAAGYNPQTHPDDIV
FTADVIDQATLERVSELQIPVNAGSVDMLDQLGQVSPGHRVWLRVNPGF
GHGHSQKTNTGGENSKHGIWYTDLPAALDVIQRHHLQLVGIHMHIGSGV
DYAHLEQVCGAMVRQVIEFGQDLQAISAGGGLSVPYQQGEEAVDTEHYY
```

GLWNAAREQIARHLGHPVKLEIEPGRFLVAQSGVLITQVRSVKQMGSRH
FVLVDAGFNDLMRPAMYGSYHHISALAADGRSLEHAPTVETVVAGPLCE
SGDVFTQQEGGNVETRALPEVKAGDYLVLHDTGAYGASMSSNYNSRPLL
PEVLFDNGQARLIRRRQTIEELLALELL lysC-1 nucleic acid sequence
SEQ ID NO: 26
TGTCTGAAATTGTTGTCTCCAAATTTGGCGGTACCAGCGTAGCTGATTT
TGACGCCATGAACCGCAGCGCTGATATTGTGCTTTCTGATGCCAACGTG
CGTTTAGTTGTCCTCTCGGCTTCTGCTGGTATCACTAATCTGCTGGTCG
CTTTAGCTGAAGGACTGGAACCTGGCGAGCGATTCGAAAAACTCGACGC
TATCCGCAACATCCAGTTTGCCATTCTGGAACGTCTGCGTTACCCGAAC
GTTATCCGTGAAGAGATTGAACGTCTGCTGGAGAACATTACTGTTCTGG
CAGAAGCGGCGGCGCTGGCAACGTCTCCGGCGCTGACAGATGAGCTGGT
CAGCCACGGCGAGCTGATGTCGACCCTGCTGTTTGTTGAGATCCTGCGC
GAACGCGATGTTCAGGCACAGTGGTTTGATGTACGTAAAGTGATGCGTA
CCAACGACCGATTTGGTCGTGCAGAGCCAGATATAGCCGCGCTGGCGGA
ACTGGCCGCGCTGCAGCTGCTCCCACGTCTCAATGAAGGCTTAGTGATC
ACCCAGGGATTTATCGGTAGCGAAAATAAAGGTCGTACAACGACGCTTG
GCCGTGGAGGCAGCGATTATACGGCAGCCTTGCTGGCGGAGGCTTTACA
CGCATCTCGTGTTGATATCTGGACCGACGTCCCGGGCATCTACACCACC
GATCCACGCGTAGTTTCCGCAGCAAAACGCATTGATGAAATCGCGTTTG
CCGAAGCGGCAGAGATGGCAACTTTTGGTGCAAAAGTACTGCATCCGGC
AACGTTGCTACCCGCAGTACGCAGCGATATCCCGGTCTTTGTCGGCTCC
AGCAAAGACCCACGCGCAGGTGGTACGCTGATGTGCAATAAAACTGAAA
ATCCGCCGCTGTTCCGCGCTCTGGCGCTTCGTCGCAATCAGACTCTGCT
CACTTTGCACAGCCTGAATATACTGCATTCTCGCGATTTCCTCGCGGAA
GTTTTCGGCATCCTCGCGCGGCATAATATTTCGGTAGACTTAATCACCA
CGTCAGAAGTGAGCGTGGCATTAACCCTTGATACCACCGGTTCAACCTC
CACTGGCGATACGTTGCTGACGCAATCTCTGCTGATGGAGCTTTCCGCA
CTGTGTCGGGTGGAGGTGGAAGAAGGTCTGGCGCTGGTCGCGTTGATTG
GCAATGACCTGCCAAAAGCCTGCGGCGTTGGCAAAGAGGTATTCGGCGT
ACTGGAACCGTTCAACATTCGCATGATTTGTTATGGCGCATCCAGCCAT
AACCTGTGCTTCCTGGTGCCCGGCGAAGATGCCGAGCAGGTGGTGCAAA
AACTGCATAGTAATTTGTTTGAGTAA LysC-1 polypeptide sequence
SEQ ID NO: 27
MSEIVVSKFGGTSVADFDAMNRSADIVLSDANVRLVVLSASAGITNLLV
ALAEGLEPGERFEKLDAIRNIQFAILERLRYPNVIREEIERLLENITVL
AEAAALATSPALTDELVSHGELMSTLLFVEILRERDVQAQWFDVRKVMR
TNDRFGRAEPDIAALAELAALQLLPRLNEGLVITQGFIGSENKGRTTTL
GRGGSDYTAALLAEALHASRVDIWTDVPGIYTTDPRVVSAAKRIDEIAF
AEAAEMATFGAKVLHPATLLPAVRSDIPVFVGSSKDPRAGGTLVCNKTE
NPPLFRALALRRNQTLLTLHSLNILHSRDFLAEVFGILARHNISVDLIT TSEVSVALTLDTTGSTSGDTLLTQSLLMELSALCRVEVEEGLALVALI
GNDLSKACGVGKEVFGVLEPFNIRMICYGASSHNLCFLVPGEDAEQVVQ
KLHSNLFE S-lysC nucleic acid sequence
SEQ ID NO: 28
ATGGGCTTAGTTGTGCAGAAATACGGCGGTAGTAGCGTGGCCGATGCCG
AAGGCATCAAACGTGTTGCCAAACGCATTGTTGAAGCCAAAAAGAATGG
TAATCAGGTTGTGGTTGTCGTTTCAGCAATGGGCGATACCACAGATGAA
CTTATTGATCTGGCCCAGGAAGTTAGCCCGATTCCGAGCGGTCGTGAAT
TTGATATGTTACTTACAGCCGGTGAACGTATTAGCATGGCCTTACTGGC
CATGGCAATCAAAAATCTGGGTCACGAAGCCCAGAGCTTCACAGGTTCA
CAGGCCGGTGTTATTACAGATAGCGTTCATAATAAAGCGCGCATTATCG
ATGTTACCCCGGGTCGTATTAAAGCAAGCCTGGATGAAGGCAACATCGC
CATTGTGGCAGGCTTTCAGGGTGTTAGCCAGGATAAAAAGGATATTACC
ACACTGGGTCGCGGTGGCAGCGATACAACGGCAGTGGCCCTGGCAGCCG
CATTAAATGCAGATGTTTGTGAAATCTATACCGATGTTGATGGTGTTTT
TACCGCAGATCCGCGCGTGGTTAAGAAAGCCCGTAAAATTGAATGGATC
TCATTCGAAGATATGCTGGAATTAGCCAGCAGCGGTAGCAAAGTTCTGC
TGCATCGTTGTGTTGAATATGCACGCCGTTACAATATTCCTATTCATGT
TCGTTCAAGTTTTTCAGGTTTACAGGGCACATGGGTTAGCAATGAACCG
CAGGGTGATCGTCCGATGGAACAGGCAATCATTAGCGGTGTTGCACATG
ATACCTCAGAAGCAAAAGTTACCGTTGTTGGTGTTCCGGATAAACCGGG
CGAAGCAGCACGTATCTTTCGGGCCATTGCCGATTCAGAAGTGAATATC
GACATGGTGGTTCAGAATGTTAGCGCAGCAAGCACCGGTCTGACCGATA
TTAGCTTTACCCTGCCGAAAGCAGAAGGTCGTAAAGCAGTTGCAGCACT
GGAGAAAAACCCGTGCAGCCGTGGGCTTTGATAGTTTACGGTATGATGAT
CAGATTGCAAAAATTAGCCTGGTTGGTGCAGGTATGAAAACCAATCCGG
GTGTGACCGCAACCTTTTTTGAAGCATTAAGCAATGCAGGCGTTAATAT
TGAACTGATTAGCACCAGTGAAATTCGTATCAGCGTTGTGACCCGCGCA
GATGATGTTAATGAAGCCGTTCAGGCAGTTCATAGCGCATTTGGTCTGG
ATAGCGAAACCGATGAAGCAGTGGTTTATGGCGGCACAGGTCGTTAA S-LysC polypeptide sequence
SEQ ID NO: 29
MGLVVQKYGGSSVADAEGIKRVAKRIVEAKKNGNQVVAVVSAMGDTTDE
LIDLAEQVSPIPAGRELDMLLTAGERISMALLAMAIKNLGHEAQSFTGS
QAGVITDSVHNKARIIDVTPGRIRTSVDEGNVAIVAGFQGVSQDSKDIT
TLGRGGSDTTAVALAAALDADVCEIYTDVDGVFTADPRVVPKAKKIDWI
SFEDMLELAASGSKVLLHRCVEYARRYNIPIHVRSSFSGLQGTWVSSEP
IKQGEKHVEQALISGVAHDTSEAKVTVVGVPDKPGEAAAIFRAIADAQV
NIDMVVQNVSAASTGLTDISFTLPKSEGRKAIDALEKNRPGIGFDSLRY
DDQIGKISLVGAGMKSNPGVTADFFTALSDAGVNIELISTSEIRISVVT
RKDDVNEAVRAVHTAFGLDSDSDEAVVYGGTGR asd nucleic acid sequence
SEQ ID NO: 30
ATGAAAAATGTTGGTTTTATCGGCTGGCGCGGTATGGTCGGCTCCGTTC
TCATGCAACGCATGGTTGAAGAGCGCGACTTCGACGCCATTCGCCCTGT
CTTCTTTTCTACTTCTCAGCTTGGCCAGGCTGCGCCGTCTTTTGGCGGA
ACCACTGGCACACTTCAGGATGCCTTTGATCTGGAGGCGCTAAAGGCCC
TCGATATCATTGTGACCTGTCAGGGCGGCGATTATACCAACGAAATCTA
TCCAAAGCTTCGTGAAAGCGGATGGCAAGGTTACTGGATTGACGCAGCA
TCGTCTCTGCGCATGAAAGATGACGCCATCATCATTCTTGACCCCGTCA
ATCAGGACGTCATTACCGACGGATTAAATAATGGCATCAGGACTTTTGT
TGGCGGTAACTGTACCGTAAGCCTGATGTTGATGTCGTTGGGTGGTTTA
TTCGCCAATGATCTTGTTGATTGGGTGTCCGTTGCAACCTACCAGGCCG
CTTCCGGCGGTGGTGCGCGACATATGCGTGAGTTATTAACCCAGATGGG
CCATCTGTATGGCCATGTGGCAGATGAACTCGCGACCCCGTCCTCTGCT
ATTCTCGATATCGAACGCAAAGTCACAACCTTAACCCGTAGCGGTGAGC
TGCCGGTGGATAACTTTGGCGTGCCGCTGGCGGGTAGCCTGATTCCGTG
GATCGACAAACAGCTCGATAACGGTCAGAGCCGCGAAGAGTGGAAAGGG
CAGGCGGAAACCAACAAGATCCTCAACACATCTTCCGTAATTCCGGTAG
ATGGTTTATGTGTGCGTGTCGGGGCATTGCGCTGCCACAGCCAGGCATT
CACTATTAAATTGAAAAAGATGTGTCTATTCCGACCGTGGAAGAACTG
CTGGCTGCGCACAATCCGTGGGCGAAAGTCGTTCCGAACGATCGGGAAA
TCACTATGCGTGAGCTAACCCCAGCTGCCGTTACCGGCACGCTGACCAC
GCCGGTAGGCCGCCTGCGTAAGCTGAATATGGGACCAGAGTTCCTGTCA
GCCTTTACCGTGGGCGACCAGCTGCTGTGGGGGGCCGCGGAGCCGCTGC
GTCGGATGCTTCGTCAACTGGCGTAA Asd polypeptide sequence
SEQ ID NO: 31
MKNVGFIGWRGMVGSVLMQRMVEERDFDAIRPVFFSSTQLGQAAPSFGG
TTGTLQDAFDLEALKALDIIVTCQGGDYTNEIYPKLRESGWQGYWIDAA
SSLRMKDDAIIILDPVNQDVITDGLNNGIRTFVGGNCTVSLMLMSLGGL
FANDLVDWVSVATYQAASGGGARHMRELLTQMGHLYGHVADELATPSSA
ILDIERKVTTLTRSGELPVDNFGVPLAGSLIPWIDKQLDNGQSREEWKG
QAETNKILNTSSVIPVDGLCVRVGALRCHSQAFTIKLKKDVSIPTVEEL
LAAHNPWAKVVPNDREITMRELTPAAVTGTLTTPVGRLRKLNMGPEFLS
AFTVGDQ dapB nucleic acid sequence
SEQ ID NO: 32
ATGCATGATGCAAACATCCGCGTTGCCATCGCGGGAGCCGGGGGGCGTA
TGGGCCGCCAGTTGATTCAGGCGGCGCTGGCATTAGAGGGCGTGCAGTT
GGGCGCTGCGCTGGAGCGTGAAGGATCTTCTTTACTGGGCAGCGACGCC
GGTGAGCTGGCCGGAGCCGGGAAAACAGGCGTTACCGTGCAAAGCAGCC
TCGATGCGGTAAAAGATGATTTTGATGTGTTTATCGATTTTACCCGTCC
GGAAGGTACGCTGAACCATCTCGCTTTTTGTCGCCAGCATGGCAAAGGG
ATGGTGATCGGCACTACGGGGTTTGACGAAGCCGGTAAACAAGCAATTC
GTGACGCCGCTGCCGATATTGCGATTGTCTTTGCTGCCAATTTTAGCGT
TGGCGTTAACGTCATGCTTAAGCTGCTGGAGAAAGCAGCCAAAGTGATG
GGTGACTACACCGATATCGAAATTATTGAAGCACATCATAGACATAAAG
TTGATGCGCCGTCAGGCACCGCACTGGCAATGGGAGAGGCGATCGCCCA
CGCCCTTGATAAAGATCTGAAAGATTGCGCGGTCTACAGTCGTGAAGGC
CACACCGGTGAACGTGTGCCTGGCACCATTGGTTTTGCCACCGTGCGTG
CAGGTGACATCGTTGGTGAACATACCGCGATGTTTGCCGATATTGGCGA
GCGTCTGGAGATCACCCATAAGGCGTCCAGCCGTATGACATTTGCTAAC
GGCGCGGTAAGATCGGCTTTGTGGTTGAGTGGTAAGGAAAGCGGTCTTT
TTGATATGCGAGATGTACTTGATCTCAATAATTTGTAA DapB polypeptide sequence
SEQ ID NO: 33
MHDANIRVAIAGAGGRMGRQLIQAALALEGVQLGAALEREGSSLLGSDA
GELAGAGKTGVTVQSSLDAVKDDFDVFIDFTRPEGTLNHLAFCRQHGKG
MVIGTTGFDEAGKQAIRDAAADIAIVFAANFSVGVNVMLKLLEKAAKVM
GDYTDIEITEABERBKVDAPSGTALAMGEAIAHALDKDLKDCAVYSREG
HTGERVPGTIGFATVRAGDIVGEHTAMFADIGERLEITHKASSRMTFAN
GAVRSALWLSGKESGLFDMRDVLDLNNL dapD nucleic acid sequence
SEQ ID NO: 34
ATGCAGCAGTTACAGAACATTATTGAAACCGCTTTTGAACGCCGTGCCG
AGATCACGCCAGCCAATGCAGACACCGTTACCCGCGAAGCGGTAAATCA
GGTGATCGCCCTGCTGGATTCCGGCGCACTGCGTGTAGCGGAAAAAATT
GACGGTCAGTGGGTGACGCATCAGTGGTTGAAAAAAGCGGTGCTGCTCT
CTTTTCGTATTAATGATAATCAGGTGATCGAAGGGGCAGAAAGCCGCTA
CTTCGACAAAGTGCCGATGAAATTCGCCGACTACGACGAAGCACGTTTC
CAGAAAGAAGGCTTCCGCGTTGTGCCACCAGCGGCGGTACGTCAGGGTG
CGTTTATTGCCCGTAACACCGTGCTGATGCCGTCTTACGTCAACATCGG
CGCATATGTTGATGAAGGCACCATGGTTGATACCTGGGCGACCGTCGGT
TCTTGTGCGCAGATTGGTAAAAACGTCCACCTTTCCGGTGGCGTGGGCA
TCGGCGGCGTGCTGGAACCGCTGCAGGCTAACCCAACCATCATTGAAGA
TAATTGCTTCATCGGCGCGCGCTCTGAAGTGGTTGAAGGGGTGATTGTC
GAAGAAGGTTCCGTCATTTCCATGGGCGTATACATTGGTCAGAGCACCC
GTATTTACGACCGTGAAACCGGCGAAATCCACTACGGTCGCGTTCCGGC
GGGGTCTGTGGTTGTTTCAGGTAATCTGCCGTCAAAAGATGGCAAATAC
AGCCTCTACTGTGCGGTTATCGTTAAGAAAGTTGACGCGAAAACTCGCG
GCAAAGTCGGCATTAACGAACTGCTGCGTACCATCGACTAA DapD polypeptide sequence
SEQ ID NO: 35
MQQLQNIIETAFERRAEITPANADTVTREAVNQVIALLDSGALRVAEKI
DGQWVTHQWLKKAVLLSFRINDNQVIEGAESRYFDKVPMKFADYDEARF
QKEGFRVVPPAAVRQGAFIARNTVLMPSYVNIGAYVDEGTMVDTWATVG
SCAQIGKNVHLSGGVGIGGVLEPLQANPTIIEDNCFIGARSEVVEGVIV

EEGSVISMGVYIGQSTRIYDRETGEIHYGRVPAGSVVVSGNLPSKDGKY

SLYCAVIVKKVDAKTRGKVGINELLRTID aspC nucleic acid sequence
SEQ ID NO: 36

ATGTTTGAGAACATTACCGCCGCTCCTGCCGACCCGATTCTGGGCCTGG

CCGATCTGTTTCGTGCCGATGAACGTCCCGGCAAAATTAACCTCGGGAT

TGGTGTCTATAAAGATGAGACGGGCAAAACCCCGGTACTGACCAGCGTG

AAAAAGGCTGAACAGTATCTGCTCGAAAATGAAACCACCAAAAATTACC

TCGGCATTGACGGCATCCCTGAATTTGGTCGCTGCACTCAGGAACTGCT

GTTTGGTAAAGGTAGCGCCCTGATCAATGACAAACGTGCTCGCACGGCA

CAGACTCCGGGGGGCACTGGCGCACTACGCGTGGCTGCCGATTTCCTGG

CAAAAAATACCAGCGTTAAGCGTGTGTGGGTGAGCAACCCAAGCTGGCC

GAACCATAAGAGCGTCTTTAACTCTGCAGGTCTGGAAGTTCGTGAATAC

GCTTATTATGATGCGGAAAATCACACTCTTGACTTCGATGCACTGATTA

ACAGCCTGAATGAAGCTCAGGCTGGCGACGTAGTGCTGTTCCATGGCTG

CTGCCATAACCCAACCGGTATCGACCCTACGCTGGAACAATGGCAAACA

CTGGCACAACTCTCCGTTGAGAAAGGCTGGTTACCGCTGTTTGACTTCG

CTTACCAGGGTTTTGCCCGTGGTCTGGAAGAAGATGCTGAAGGACTGCG

CGCTTTCGCGGCTATGCATAAAGAGCTGATTGTTGCCAGTTCCTACTCT

AAAAACTTTGGCCTGTACAACGAGCGTGTTGGCGCTTGTACTCTGGTTG

CTGCCGACAGTGAAACCGTTGATCGCGCATTCAGCCAAATGAAAGCGGC

GATTCGCGCTAACTACTCTAACCCACCAGCACACGGCGCTTCTGTTGTT

GCCACCATCCTGAGCAACGATGCGTTACGTGCGATTTGGGAACAAGAGC

TGACTGATATGCGCCAGCGTATTCAGCGTATGCGTCAGTTGTTCGTCAA

TACGCTGCAGGAAAAGGCGCAAACCGCGACTTCAGCTTTATCATCAAA

CAGAACGGCATGTTCTCCTTCAGTGGCCTGACAAAAGAACAAGTGCTGC

GTCTGCGCGAAGAGTTTGGCGTATATGCGGTTGCTTCTGGTCGCGTAAA

TGTGGCCGGGATGACACCAGATAACATGGCTCCGCTGTGCGAAGCGATT

GTGGCAGTGCTGTAA

AspC polypeptide sequence
SEQ ID NO: 37

MFENITAAPADPILGLADLFRADERPGKINLGIGVYKDETGKTPVLTSV

KKAEQYLLENETTKNYLGIDGIPEFGRCTQELLFGKGSALINDKRARTA

QTPGGTGALRVAADFLAKNTSVKRVWVSNPSWPNHKSVFNSAGLEVREY

AYYDAENHTLDFDALINSLNEAQAGDVVLFHGCCHNPTGIDPTLEQWQT

LAQLSVEKGWLPLFDFAYQGFARGLEEDAEGLRAFAAMHKELIVASSYS

KNFGLYNERVGACTLVAADSETVDRAFSQMKAAIRANYSNPPAHGASVV

ATILSNDALRAIWEQELTDMRQRIQRMRQLFVNTLQEKGANRDFSFIIK

QNGMFSFSGLTKEQVLRLREEFGVYAVASGRVNVAGMTPDNMAPLCEAI

VAVL

YbjE polypeptide sequence
SEQ ID NO: 38

MFSGLLIILVPLIVGYLIPLRQQAALKVINQLLSWMVYLILFFMGISLA

FLDNLASNLLAILHYSAVSITVILLCNIAALMWLERGLPWRNHHQQEKL

PSRIAMALESLKLCGVVVIGFAIGLSGLAFLQHATEASEYTLILLLFLV

GIQLRNNGMTLKQIVLNRRGMIVAVVVVVSSLIGGLINAFILDLPINTA

LAMASGFGWYSLSGILLTESFGPVIGSAAFFNDLARELIAIMLIPGLIR

RSRSTALGLCGATSMDFTLPVLQRTGGLDMVPAAIVHGFILSLLVPILI

AFFSA.

---

What is claimed is:

1. A genetically modified host cell comprising a heterologous nucleic acid encoding an OMP porin polypeptide, wherein the host cell overexpresses the OMP porin polypeptide and has increased production of an amino acid lysine and cadaverine, and wherein the OMP porin polypeptide is an OmpA, OmpC, OmpF, OmpX, OmpE, OmpG, or OmpW porin polypeptide set forth as SEQ ID NO: 4, 6, 8, 10, 12, 14, or 16 respectively; or wherein the OMP porin polypeptide is a conservatively modified porin polypeptide variant of SEQ ID NO: 4, 6, 8, 10, 12, 14, or 16 that encodes the mature OMP porin polypeptide.

2. The genetically modified host cell of claim 1, wherein the heterologous nucleic acid encoding the OMP porin polypeptide is encoded by an expression vector introduced into the cell, wherein the expression vector comprises the heterologous nucleic acid operably linked to a promoter; and/or
   wherein the OMP porin polypeptide is endogenous to the host cell; and/or
   wherein the heterologous nucleic acid is integrated into the host chromosome; and/or
   wherein the host cell overexpresses a lysine decarboxylase; and/or
   wherein the host cell overexpresses one or more lysine biosynthesis polypeptides; and/or
   wherein the host cell overexpresses a TetA polypeptide.

3. The genetically modified host cell of claim 1, wherein the host cell is of the genus *Escherichia, Hafnia,* or *Corynebacterium*; and/or wherein the host cell is *Escherichia coli, Hafnia alvei,* or *Corynebacterium glutamicum*; and/or wherein the host cell is *Escherichia coli* or *Hafnia alvei*.

4. The genetically modified host cell of claim 3, wherein the Omp porin polypeptide is an OmpA, OmpC, OmpF, or OmpW polypeptide.

5. The genetically modified host cell of claim 4, wherein the host cell overexpresses a lysine decarboxylase polypeptide; and/or wherein the host cell overexpresses a LysC, DapA, LysA, Asd, DapB, AspC, or TetA polypeptide.

6. A method of producing an amino acid, the method comprising culturing a host cell of claim 1 under conditions in which the OMP porin polypeptide is overexpressed.

* * * * *